US008685937B2

(12) United States Patent
Giangrande et al.

(10) Patent No.: US 8,685,937 B2
(45) Date of Patent: Apr. 1, 2014

(54) NUCLEIC ACID APTAMERS

(75) Inventors: Paloma H. Giangrande, Iowa City, IA (US); James O. McNamara, Iowa City, IA (US); Anton P. McCaffrey, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 103 days.

(21) Appl. No.: 13/057,443

(22) PCT Filed: Aug. 6, 2009

(86) PCT No.: PCT/US2009/053023
§ 371 (c)(1),
(2), (4) Date: Oct. 6, 2011

(87) PCT Pub. No.: WO2010/019446
PCT Pub. Date: Feb. 18, 2010

(65) Prior Publication Data
US 2012/0014875 A1 Jan. 19, 2012

Related U.S. Application Data

(60) Provisional application No. 61/087,652, filed on Aug. 9, 2008, provisional application No. 61/155,288, filed on Feb. 25, 2009.

(51) Int. Cl.
*A61K 31/70* (2006.01)
*C07H 21/04* (2006.01)
*C07H 21/02* (2006.01)
*C12Q 1/68* (2006.01)

(52) U.S. Cl.
USPC ...... 514/44 A; 514/44 R; 536/23.1; 536/24.1; 536/24.5; 435/375; 435/377

(58) Field of Classification Search
None
See application file for complete search history.

(56) References Cited

U.S. PATENT DOCUMENTS

| 4,683,195 | A | 7/1987 | Mullis |
| 4,683,202 | A | 7/1987 | Mullis |
| 4,800,159 | A | 1/1989 | Mullis |
| 4,965,188 | A | 10/1990 | Mullis |
| 5,667,969 | A | 9/1997 | Sullenger et al. |
| 5,854,038 | A | 12/1998 | Sullenger et al. |
| 5,869,254 | A | 2/1999 | Sullenger et al. |
| 6,897,016 | B1 | 5/2005 | Sullenger et al. |
| 7,045,293 | B2 | 5/2006 | Sullenger et al. |
| 7,300,922 | B2 | 11/2007 | Sullenger et al. |
| 7,312,325 | B2 | 12/2007 | Sullenger et al. |
| 2002/0119473 | A1* | 8/2002 | Lupold et al. ............ 435/6 |
| 2003/0036517 | A1 | 2/2003 | Sullenger et al. |
| 2003/0083294 | A1 | 5/2003 | Sullenger et al. |
| 2003/0175703 | A1 | 9/2003 | Sullenger et al. |
| 2004/0171058 | A1 | 9/2004 | Sullenger et al. |
| 2005/0158780 | A1 | 7/2005 | Lupold |
| 2006/0105975 | A1 | 5/2006 | Pendergrast |
| 2006/0246123 | A1 | 11/2006 | Gilboa et al. |
| 2007/0041901 | A1 | 2/2007 | Diener |
| 2007/0122385 | A1 | 5/2007 | Carette |
| 2008/0026947 | A1 | 1/2008 | Gmeiner |
| 2008/0051339 | A1 | 2/2008 | Sullenger et al. |
| 2008/0176766 | A1 | 7/2008 | Brown |
| 2008/0182809 | A1 | 7/2008 | Sullenger et al. |
| 2008/0200413 | A1 | 8/2008 | Sullenger et al. |
| 2008/0207546 | A1 | 8/2008 | Sullenger et al. |
| 2008/0221053 | A1 | 9/2008 | Sullenger et al. |
| 2008/0234941 | A1* | 9/2008 | Jackson et al. ............ 702/19 |
| 2009/0215874 | A1 | 8/2009 | Sullenger et al. |
| 2010/0076060 | A1 | 3/2010 | Sullenger et al. |
| 2010/0234450 | A1 | 9/2010 | Schultz |
| 2010/0267802 | A1* | 10/2010 | Sullenger ............ 514/44 A |
| 2010/0324113 | A1 | 12/2010 | Sullenger |
| 2011/0052697 | A1* | 3/2011 | Farokhzad et al. ........ 424/486 |

FOREIGN PATENT DOCUMENTS

| WO | WO 2007/035518 A2 | 3/2007 |
| WO | WO 2007/143086 A2 | 12/2007 |
| WO | WO 2008/048685 A2 | 4/2008 |
| WO | WO 2010/019446 A1 | 2/2010 |

OTHER PUBLICATIONS

Aigner, "Gene silencing through RNA interference (RNAi) in vivo: strategies based on the direct application of siRNAs", *J Biotechnol.* 124(1), 12-25 (2006).
Bagalkot et al., "siRNA-aptamer chimeras on nanoparticles: preserving targeting functionality for effective gene silencing", *ACS Nano*, vol. 5 (10), 8131-8139 (2011).
Bozza et al., "Characterization of the secondary structure and stability of an RNA aptamer that binds vascular endothelial growth factor", *Biochemistry* 45(24), 7639-7643 (2006).
Chan et al., "Phase 1b randomized study of antidote-controlled modulation of factor IXa activity in patients with stable coronary artery disease", *Circulation* 117(22), 2865-2874 (2008).
Chiu et al., "siRNA function in RNAi: a chemical modification analysis", *RNA* 9(9), 1034-1048 (2003).
Chu et al., "Aptamer Mediated siRNA Delivery", *Nucleic Acids Research*, vol. 34, No. 10, 6 pages (2006).

(Continued)

*Primary Examiner* — Sean McGarry
(74) *Attorney, Agent, or Firm* — Viksnins Harris & Padys PLLP

(57) ABSTRACT

The present invention relates to optimized aptamers and methods of using these aptamers.

15 Claims, 15 Drawing Sheets

(56) References Cited

OTHER PUBLICATIONS

Chu et al., "Using Aptamers to Identify and Enter Cells", *Curr Opin Mol Ther.* 9(2), 137-144 (2007), Review. Erratum in: *Curr Opin Mol Ther.* 9(3), 305, (2007).
Czauderna et al., "Structural variations and stabilizing modifications of synthetic siRNAs in mammalian cells", *Nucleic Acids Res.* 31(11), 2705-2716 (2003).
Drake et al., "Assessing tumor growth and distribution in a model of prostate cancer metastasis using bioluminescence imaging", *Clin Exp Metastasis* 22(8), 674-684 (2005).
Dyke et al., "First-in-human experience of an antidote-controlled anticoagulant using RNA aptamer technology: a phase 1a pharmacodynamic evaluation of a drug-antidote pair for the controlled regulation of factor IXa activity", *Circulation* 114(23), 2490-2497 (2006).
Gilbert et al., "First-in-human evaluation of anti von Willebrand factor therapeutic aptamer ARC1779 in healthy volunteers", *Circulation* 116(23), 2678-2686 (2007).
Girvan et al., "AGRO100 inhibits activation of nuclear factor-kappaB (NF kappaB) by forming a complex with NF-kappaB essential modulator (NEMO) and nucleolin", *Mol Cancer Ther.* 5(7), 1790-1799 (2006).
Guo et al., "Specific Delivery of Therapeutic RNAs to Cancer Cells via the Dimerization Mechanism of phi29 Motor pRNA", *Hum. Gene Therapy*, 16, 1097-1109 (2005).
Heidel et al., "Administration in non-human primates of escalating intravenous doses of targeted nanoparticles containing ribonucleotide reductase subunit M2 siRNA", *Proc Natl Acad Sci USA.* 104(14), 5715-5721 (2007).
Howard et al., "RNA interference in vitro and in vivo using a novel chitosan/siRNA nanoparticle system". *Mol Ther.* 14(4), 476-484 (2006).
Hu-Lieskovan et al., "Sequence-specific knockdown of EWS-FLI1 by targeted, nonviral delivery of small interfering RNA inhibits tumor growth in a murine model of metastatic Ewing's sarcoma", *Cancer Res.* 65(19), 8984-8992 (2005).
Katz et al., "Macugen (pegaptanib sodium), a novel ocular therapeutic that targets vascular endothelial growth factor (VEGF)", *Int Ophthalmol Clin.* 46(4), 141-154 (2006).
Keck et al., "Rational Design Leads to More Potent RNA Interference Against Hepatitis B Virus: Factors Effecting Silencing Efficiency", *Mol Ther.*, vol. 17 (3), 538-547 (2009).
Khvorova et al., "Functional siRNAs and miRNAs exhibit strand bias", *Cell* 115(2), 209-216 (2003).
Kim et al., "Prostate cancer cell death produced by the co-delivery of Bcl-xL shRNA and doxorubicin using an aptamer-conjugated polyplex", *Biomaterials*, 31, 4592-4599 (2010).
Kumar et al., "Transvascular delivery of small interfering RNA to the central nervous system", *Nature* 448, 39-43 (2007).
Layzer et al., "In vivo activity of nuclease-resistant siRNAs", *RNA* 10(5), 766-771(2004).
Lupold et al., "Identification and characterization of nuclease-stabilized RNA molecules that bind human prostate cancer cells via the prostate-specific membrane antigen", *Cancer Res.* 62(14), 4029-4033 (2002).
Ma et al., "Structural basis for overhang-specific small interfering RNA recognition by the PAZ domain", *Nature* 429, 318-322 (2004).
Manoharan, "RNA Interference and Chemically Modified Small Interfering RNAs", *Current Opinion in Chemical Biology*, 8, 570-579 (2004).
McNamara et al., "Cell type-specific delivery of siRNAs with aptamer-siRNA chimeras", *Nat Biotechnol.* 24(8), 1005-1015 (2006).
Meade et al., "Exogenous siRNA delivery using peptide transduction domains/cell penetrating peptides", *Adv Drug Deliv Rev.* 59(2-3), 134-140 (2007).
Neff et al., "An aptamer-siRNA chimera suppresses HIV-1 viral loads and protects from helper CD4(+) T cell decline in humanized mice", *Sci Transl Med.*, vol. 3(66), 1-10 (2011).

Ni et al., "Prostate-targeted radiosensitization via aptamer-shRNA chimeras in human tumor xenografts", *J Clin Invest.*, vol. 121 (6), 2383-2390 (2011).
Pall et al., "Improved northern blot method for enhanced detection of small RNA", *Nat Protoc.* 3(6), 1077-1084 (2008).
Pastor et al., "Induction of tumour immunity by targeted inhibition of nonsense-mediated mRNA decay", *Nature*, 465, 227-230 (2010).
Patent Cooperation Treaty, International Searching Authority, Search Report and Written Opinion for PCT/US09/53023, 15 pages, Nov. 5, 2009.
Peer et al., "Selective gene silencing in activated leukocytes by targeting siRNAs to the integrin lymphocyte function-associated antigen-1", *Proc Natl Acad Sci USA.* 104(10), 4095-4100 (2007).
Pillé et al., "Intravenous delivery of anti-RhoA small interfering RNA loaded in nanoparticles of chitosan in mice: safety and efficacy in xenografted aggressive breast cancer", *Hum Gene Ther.* 17(10), 1019-1026 (2006).
Reagan-Shaw et al., "Silencing of polo-like kinase (Plk) 1 via siRNA causes induction of apoptosis and impairment of mitosis machinery in human prostate cancer cells: implications for the treatment of prostate cancer", *FASEB J.* 19(6), 611-613 (2005).
Reagan-Shaw et al., "Polo-like Kinase (Plk) 1 as a Target for Prostate Cncer Mangement", *IUPMB Life*, 57(10), 677-682 (2005).
Reynolds et al., "Rational siRNA design for RNA interference", *Nat Biotechnol.* 22(3), 326-330 (2004).
Rose et al., "Functional polarity is introduced by Dicer processing of short substrate RNAs", *Nucleic Acids Res.* 33(13), 4140-4156 (2005).
Rozema et al., "Dynamic PolyConjugates for targeted in vivo delivery of siRNA to hepatocytes", *Proc Natl Acad Sci USA.* 104(32), 12982-12987 (2007).
Sano et al., "Effect of asymmetric terminal structures of short RNA duplexes on the RNA interference activity and strand selection", *Nucleic Acids Res.* 36(18), 5812-5821 (2008).
Schwarz et al., "Asymmetry in the assembly of the RNAi enzyme complex", *Cell* 115(2), 199-208 (2003).
Song et al., "Antibody mediated in vivo delivery of small interfering RNAs via cell-surface receptors", *Nat Biotechnol.* 23(6), 709-717 (2005).
Soundararajan et al., "The nucleolin targeting aptamer AS1411 destabilizes Bcl-2 messenger RNA in human breast cancer cells", *Cancer Res.* 68(7), 2358-2365 (2008).
Soutschek et al., "Therapeutic silencing of an endogenous gene by systemic administration of modified siRNAs", *Nature* 432, 173-178 (2004).
Strebhardt et al., "Targeting polo-like kinase 1 for cancer therapy", *Nat. Rev. Cancer*, 6(4), 321-330 (2006).
Takei et al., "A small interfering RNA targeting vascular endothelial growth factor as cancer therapeutics", *Cancer Res.* 64(10), 3365-3370 (2004).
Takeshita et al., "Therapeutic potential of RNA interference against cancer", *Cancer Sci.* 97(8), 689-696 (2006).
Thiel et al., "Intracellular delivery of RNA-based therapeutics using aptamers", *Ther Deliv.*, 1(6), (2010).
Thiel et al., "Delivery of chemo-sensitizing siRNAs to HER2+−breast cancer cells using RNA aptamers", *Nucleic Acids Res.* 40(13), 6319-6337 (2012).
Veronese et al., "The impact of PEGylation on biological therapies", *BioDrugs.* 22(5), 315-329 (2008).
Wheeler et al., "Inhibition of HIV transmission in human cervicovaginal explants and humanized mice using CD4 aptamer-siRNA chimeras", J Clin Invest. (6), 2401-2412 (2011).
Wolfrum et al., "Mechanisms and optimization of in vivo delivery of lipophilic siRNAs", *Nat Biotechnol.* 25(10), 1149-1157 (2007).
Zhou et al., "Novel dual inhibitory function aptamer-siRNA delivery system for HIV-1 therapy", *Mol Ther.* 16(8), 1481-1489 (2008).
Zhou et al., "The therapeutic potential of cell-internalizing aptamers", *Curr Top Med Chem.* 9(12), 1144-1157 (2009).
Zhou et al., "Aptamer-targeted cell-specific RNA interference", *Silence*, 1(4), 1-10 (2010).

(56) References Cited

OTHER PUBLICATIONS

Zhou et al., "Development of cell-type specific anti-HIV gp120 aptamers for siRNA delivery", *J Vis Exp.* (52) e2954, 11 pages (2011).

Zhou et al., "Aptamer-targeted RNAi for HIV-1 therapy", *Methods Mol Biol.* 721, 355-371 (2011).

Zhou et al., "Functional In Vivo Delivery of Multiplexed Anti-HIV-1 siRNAs via a Chemically Synthesized Aptamer With a Sticky Bridge", *Mol Ther.* Nov. 20, 2012.doi:10.1038/mt.2012.226. [Epub ahead of print] PubMed PMID: 23164935.

Zhou et al., "Therapeutic Potential of Aptamer-siRNA Conjugates for Treatment of HIV-1", *BioDrugs,* 26(6), 393-400 (2012).

Zhu et al., "Inhibition of HIV-1 protease expression in T cells owing to DNA aptamer-mediated specific delivery of siRNA", *Eur J Med Chem.* 56, 396-3999 (2012).

* cited by examiner

| TREATMENT | CONCENTRATION | % CASPASE 3 POSITIVE CELLS (AVE OF 3 EXPERIMENTS) |
|---|---|---|
| UNTREATED | - | 17% |
| CISPLATIN | 2 nM | 90% |
| A10-Plk1 | 400 nM | 52% |
| A10-Plk1 | 4 nM | 27% |
| BLUNT | 4 nM | 22% |
| OVH | 4 nM | 64% |
| G-U WOBBLE | 4 nM | 72% |
| SWAP | 4 nM | 75% |
| STEM LOOP | 4 nM | 85% |
| Plk1 siRNA | 4 nM | 13% |

FIG. 5D

NUCLEIC ACID APTAMERS

RELATED APPLICATION

This application claims priority under 35 U.S.C. 119(e) to provisional application U.S. Ser. No. 61/087,652, filed Aug. 9, 2008 and provisional application U.S. Ser. No. 61/155,288, filed Feb. 25, 2009, which applications are incorporated hereby by reference.

BACKGROUND OF THE INVENTION

Worldwide, cancer affects approximately 10 million people each year. Approximately 22 million people are living with cancer and almost 7 million people die worldwide from cancer each year. The most common cancers include cancers of the lung, breast, colon/rectum, stomach, liver, prostate, cervix, esophagus, and bladder. The elderly tend to be the highest population for new incidence, as more than 75% of all new cancer cases are diagnosed in people over the age of 60. With the aging population, incidence is expected to increase each year. Prostate cancer is the most common cancer in men and the second leading cause of cancer death in men, behind lung cancer. Approximately 80% of prostate cancers are diagnosed in men over 65 years of age, and, due to the lack of symptoms, 75% of first-time patients over 65 are diagnosed with Stage C or D, the two most advanced stages of prostate cancer. Worldwide, more than 680,000 men are diagnosed annually. Prostate cancer characteristically spreads to the bone.

RNA interference (RNAi) is a cellular mechanism by which 21-23 nt RNA duplexes trigger the degradation of cognate mRNAs. Researchers have been pursuing potential therapeutic applications of RNAi once it was demonstrated that exogenous, short interfering RNAs (siRNAs) can silence gene expression via this pathway in mammalian cells. RNAi is attractive for therapeutics because of its stringent target gene specificity, the relatively low immunogenicity of siRNAs, and the simplicity of design and testing of siRNAs.

Double-stranded RNA (dsRNA) can induce sequence-specific posttranscriptional gene silencing in many organisms by a process known as RNA interference (RNAi). However, in mammalian cells, dsRNA that is 30 base pairs or longer can induce sequence-nonspecific responses that trigger a shutdown of protein synthesis. RNA fragments are the sequence-specific mediators of RNAi. Interference of gene expression by these RNA interference (RNAi) molecules is now recognized as a naturally occurring strategy for silencing genes in the cells of many organisms.

One technical hurdle for RNAi-based clinical applications that still remains is the delivery of siRNAs across the plasma membrane of cells in vivo. A number of solutions for this problem have been described. However, most of the approaches described to date have the disadvantage of delivering siRNAs to cells non-specifically, without regard to the cell type.

For in vivo use, the therapeutic siRNA reagents need to target particular cell types (e.g., cancer cells), thereby limiting side-effects that result from non-specific delivery as well as reducing the quantity of siRNA necessary for treatment.

SUMMARY OF THE INVENTION

Accordingly, in certain embodiments, the present invention provides nucleic acid molecules not more than 45 nucleotides in length that include the nucleic acid sequence 5'-$n_1n_2n_3$CGGAUCAGC$n_4n_5n_6$GUUUA-3' (SEQ ID NO:1), wherein each $n_x$ can be present or absent, wherein when present each $n_x$ represents any nucleotide. In certain embodiments, each of the $n_x$ nucleotides can be present or absent. In certain embodiments, the nucleic acid molecule includes a sufficient number of $n_x$ nucleotides so as to form the first, second and/or third stem structures. In certain embodiments the nucleic acid molecule is not more than 45 nucleotides in length, e.g., from 15-45 nucleotides in length, e.g., 39 nucleotides in length.

In certain embodiments nucleotides, $n_1n_2n_3$ and $n_4n_5n_6$ are present and hybridize to form a stem structure.

In certain embodiments, the nucleic acid molecule includes the nucleic acid sequence 5'-AUGCGGAUCAGC-CAUGUUUA-3' (SEQ ID NO:2).

In certain embodiments, the nucleic acid molecule includes the nucleic acid sequence 5'-$n_a n_b n_c n_d n_1 n_2 n_3$CGGAUCAGC$n_4 n_5 n_6$GUUUA$n_e n_f n_g n_h$-3' (SEQ ID NO:3).

In certain embodiments, nucleotides $n_1n_2n_3$ and $n_4n_5n_6$ are present and hybridize to form a first stem structure and nucleotides $n_a n_b n_c n_d$ and $n_e n_f n_g n_h$ are present and hybridize to form a second stem structure.

In certain embodiments, the nucleic acid molecule includes the nucleic acid sequence 5'-GACGAUGCG-GAUCAGCCAUGUUUACGUC-3' (SEQ ID NO:4).

In certain embodiments, the nucleic acid molecule includes the nucleic acid sequence 5'-$n_{10}n_{11}n_{12}n_{13}n_{14}n_a n_b n_c n_d n_1 n_2 n_3$CGGAUCAGC$n_4 n_5 n_6$GUUUA$n_e n_f n_g n_h n_{15} n_{16} n_{17} n_{18} n_{19} n_{20} n_{21}$-3' (SEQ ID NO:11). In certain embodiments, $n_{21}$ is U. In certain embodiments, $n_{21}$ is absent.

In certain embodiments, nucleotides $n_1n_2n_3$ and $n_4n_5n_6$ are present and hybridize to form a first stem structure, nucleotides $n_a n_b n_c n_d$ and $n_e n_f n_g n_h$ are present and hybridize to form a second stem structure, and nucleotides $n_{10}n_{11}n_{12}n_{13}n_{14}$ and $n_{15}n_{16}n_{17}n_{18}n_{19}$ are present and hybridize to form a third stem structure.

In certain embodiments, the nucleic acid molecule includes the nucleic acid sequence 5'-GGGAGGAC-GAUGCGGAUCAGCCAUGUUUACGUCACUCCU-3' (SEQ ID NO:5).

In certain embodiments, the nucleic acid molecule consists essentially of the nucleic acid sequence 5'-GGGAGGAC-GAUGCGGAUCAGCCAUGUUUACGUCACUCCU-3' (SEQ ID NO:5).

In certain embodiments, the nucleic acid molecule consists of the nucleic acid sequence 5'-GGGAGGACGAUGCG-GAUCAGCCAUGUUUACGUCACUCCU-3' (SEQ ID NO:5).

Certain embodiments of the invention provide nucleic acid molecules, or the complements thereof, wherein the nucleic acid molecule includes the nucleic acid sequence 5'-GGGCGGCUUUGCCAAGUGUUU-3' (SEQ ID NO:6) or 5'-GGGCGGCUUUGCCAAGUGCUU-3' (SEQ ID NO:7) or 5'-GGGCGGCUUUGCCAAGUGU-3' (SEQ ID NO:8) or 5'-GCACUUGGCAAAGCCGCCCUU-3' (SEQ ID NO:10).

In certain embodiments, the nucleic acid molecule further includes a PEG molecule. In certain embodiments, the PEG molecule has an average molecular weight of about 10 to 100 kDa in size. In certain embodiments, the PEG molecule has an average molecular weight of about 10 to 40 kDa in size. In certain embodiments, the PEG molecule is PEG-20.

Certain embodiments of the invention provide a duplex of a first and second nucleic acid molecule as described herein.

In certain embodiments, the duplex further includes a loop structure linking the nucleic acid molecules of the duplex so as to form a stem and loop structure.

In certain embodiments of the duplex, the first nucleic acid molecule includes the nucleic acid sequence 5'-GGGCG-GCUUUGCCAAGUGUUU-3' (SEQ ID NO:6) and the second nucleic acid molecule includes the nucleic acid sequence 5'-GCACUUGGCAAAGCCGCCC-3' (SEQ ID NO:9).

In certain embodiments of the duplex, the first nucleic acid molecule includes SEQ ID NO:8 and the second nucleic acid molecule includes SEQ ID NO:10.

Certain embodiments of the invention provide conjugates including a nucleic acid molecule (e.g., a siRNA molecule) or the duplex of the invention linked to the A10 aptamer (5'-GGGAGGACGAUGCGGAUCAGCCAUGU-UUACGUCACUCCUUGUCAA UCCUCAUCGGCA-GACGACUCGCCCGA-3' SEQ ID NO:12)

Certain embodiments of the invention provide conjugates including a nucleic acid molecule of the invention (e.g., an aptamer) linked to a therapeutic or diagnostic molecule.

In certain embodiments, "linked" includes directly linking (covalently or non-covalently binding) the nucleic acid molecule of the invention (e.g., an aptamer) to a therapeutic or diagnostic molecule.

In certain embodiments, "linked" includes linking the nucleic acid molecule of the invention (e.g., an aptamer) to a therapeutic or diagnostic molecule using a linker, e.g., a nucleotide linker, e.g., the nucleotide sequence "AA" or "TT" or "UU".

In certain embodiments, the nucleic acid molecule of the invention (e.g., an aptamer) is linked to a diagnostic molecule.

In certain embodiments, the nucleic acid molecule of the invention (e.g., an aptamer) is linked to a therapeutic molecule.

In certain embodiments, the therapeutic molecule is an RNAi molecule, such as a siRNA molecule, e.g., a siRNA molecule targeted to polo-like kinase 1 (PLK1). While certain exemplary siRNA sequences have been utilized herein, the invention is also directed to the use of other siRNA sequences, for example, siRNA sequences that target genes involved in cancer.

In certain embodiments, the therapeutic molecule is a nucleic acid molecule duplex.

In certain embodiments, the therapeutic molecule is a microRNA (miRNA).

Certain embodiments of the invention provide a nucleic acid molecule encoding a molecule, duplex or conjugate of the invention.

Certain embodiments of the invention provide an expression cassette including at least one nucleic acid molecule of the invention.

In certain embodiments, the expression cassette further includes a promoter, such as a regulatable promoter or a constitutive promoter. Examples of suitable promoters include a CMV, RSV, pol II or pol III promoter. The expression cassette may further contain a polyadenylation signal (such as a synthetic minimal polyadenylation signal) and/or a marker gene. Examples of marker genes include visual markers such as GFP, or functional markers, such as antibiotic resistance genes.

Certain embodiments of the invention provide a vector, e.g., a viral vector, including at least one (e.g., 1 or 2) expression cassette of the invention. Examples of appropriate vectors include adenoviral, lentiviral, adeno-associated viral (AAV), poliovirus, HSV, or murine Maloney-based viral vectors. In one embodiment, the vector is an adenoviral vector. In certain embodiments, a vector may contain two expression cassettes, a first expression cassette containing a nucleic acid encoding the first strand of the RNA duplex and a second expression cassette containing a nucleic acid encoding the second strand of the RNA duplex.

Certain embodiments of the invention provide an isolated or non-human cell including the PMSA receptor and a molecule, duplex or conjugate of the invention.

Certain embodiments of the invention provide methods for delivering a therapeutic or diagnostic molecule to a cell having a PMSA receptor, including contacting the cell with a conjugate of the invention.

Certain embodiments of the invention provide a pharmaceutical composition including a molecule, duplex or conjugate of the invention and a pharmaceutically acceptable carrier.

Certain embodiments of the invention provide a method for treating a patient having cancer including administering a molecule, duplex or conjugate of the invention to the patient.

Certain embodiments of the invention provide a method for determining whether a patient has cancer (i.e., diagnosing a patient) including administering a conjugate of the invention to the patient and determining whether the patient has cancer. For example, because certain conjugates of the invention are targeted to the PMSA receptor and include a diagnostic molecule, detection of a relatively higher level of the conjugate can be used to diagnose a patient as having prostate cancer.

Certain embodiments of the invention provide a molecule, duplex or conjugate of the invention for use in therapy.

Certain embodiments of the invention provide the use of a molecule, duplex or conjugate of the invention for treating cancer.

Certain embodiments of the invention provide a molecule, duplex or conjugate of the invention for use in the prophylactic or therapeutic treatment of cancer.

In certain embodiments, the cancer is a solid sarcoma or carcinoma.

In certain embodiments, the cancer is prostate cancer.

The present invention relates to a specific delivery of siRNAs and one that, at least in one embodiment, only uses properties of RNA. The delivery method of the instant invention exploits the structural potential of nucleic acids (e.g., RNA) to target siRNAs to a particular cell-surface receptor and thus to a specific cell type. In one embodiment, the invention provides a method and compositions to specifically deliver nucleic acids that comprise both a targeting moiety (e.g., an aptamer) and an RNA-silencing moiety (e.g., an siRNA) that is recognized and processed by Dicer in a manner similar to the processing of microRNAs. Aptamers and siRNAs have low immunogenicity. They can easily be synthesized in large quantities at a relatively low cost and are amendable to a variety of chemical modifications that confer both resistance to degradation and improved pharmacokinetics in vivo. The smaller size of aptamers compared with that of antibodies (<15 kDa versus 150 kDa) facilitates their in vivo delivery by promoting better tissue penetration.

In certain embodiments of the invention, RNAi molecules are employed to inhibit expression of a target gene. By "inhibit expression" is meant to reduce, diminish or suppress expression of a target gene. Expression of a target gene may be inhibited via "gene silencing." Gene silencing refers to the suppression of gene expression, e.g., transgene, heterologous gene and/or endogenous gene expression, which may be mediated through processes that affect transcription and/or through processes that affect post-transcriptional mechanisms. In some embodiments, gene silencing occurs when an RNAi molecule initiates the degradation of the mRNA transcribed from a gene of interest in a sequence-specific manner via RNA interference, thereby preventing translation of the gene's product.

As used herein the term "encoded by" is used in a broad sense, similar to the term "comprising" in patent terminology. For example, the statement "the first strand of RNA is encoded by SEQ ID NO:1" means that the first strand of RNA sequence corresponds to the RNA sequence transcribed from the DNA sequence indicated in SEQ ID NO:1, but may also contain additional nucleotides at either the 3' end or at the 5' end of the RNA molecule.

The reference to siRNAs herein is meant to include short hairpin RNAs (shRNAs) and other small RNAs that can or are capable of modulating the expression of a target gene, for example via RNA interference. Such small RNAs include without limitation, shRNAs and miroRNAs (miRNAs).

The two strands of RNA in the siRNA may be completely complementary, or one or the other of the strands may have an "overhang region" (i.e., a portion of the RNA that does not bind with the second strand). Such an overhang region may be from 1 to 10 nucleotides in length.

The present invention provides a method of preventing PLK1 accumulation in a mammal in need thereof, e.g., by introducing the vector encoding a miRNA in an amount sufficient to suppress accumulation of PLK1. The PLK1 protein can be inhibited by at least 10%, 20%, 30%, 40%, 50%, 60%, 70%, 80%, 90%, 95%, or 99%.

This invention relates to compounds, compositions, and methods useful for inhibiting PLK1 gene expression using short interfering nucleic acid (siRNA) molecules. This invention also relates to compounds, compositions, and methods useful for modulating the expression and activity of PLK1 by RNA interference (RNAi) using small nucleic acid molecules. In particular, the instant invention features small nucleic acid molecules, such as short interfering nucleic acid (siNA), short interfering RNA (siRNA), double-stranded RNA (dsRNA), micro-RNA (miRNA), and short hairpin RNA (shRNA) molecules and methods used to modulate the expression of PLK1 genes. A siRNA of the instant invention can be chemically synthesized, expressed from a vector or enzymatically synthesized.

The present invention provides a mammalian cell containing an isolated first strand of RNA of 15 to 30 nucleotides in length, and an isolated second strand of RNA of 15 to 30 nucleotides in length, wherein the first strand contains a sequence that is complementary to for example at least 15 nucleotides of RNA encoded by a targeted gene of interest (for example the PLK1 gene), wherein for example at least 12 nucleotides of the first and second strands are complementary to each other and form a small interfering RNA (siRNA) duplex for example under physiological conditions, and wherein the siRNA silences (for example via RNA interference) only one allele of the targeted gene (for example the mutant allele of PLK1 gene) in the cell. The duplex of the siRNA may be between 15 and 30 base pairs in length. The two strands of RNA in the siRNA may be completely complementary, or one or the other of the strands may have an "overhang region" or a "bulge region" (i.e., a portion of the RNA that does not bind with the second strand or where a portion of the RNA sequence is not complementary to the sequence of the other strand). These overhangs may be at the 3' end or at the 5' region, or at both 3' and 5' ends. Such overhang regions may be from 1 to 10 (e.g., 1, 2, 3, 4, 5, 6, 7, 8, 9, 10) or more nucleotides in length. The bulge regions may be at the ends or in the internal regions of the siRNA duplex. Such bulge regions may be from 1-5 (e.g., 1, 2, 3, 4, 5) or more nucleotides long. Such bulge regions may be the bulge regions characteristic of miRNAs.

In the present invention, an expression cassette may contain a nucleic acid encoding at least one strand of the RNA duplex described above. Such an expression cassette may further contain a promoter. The expression cassette may be contained in a vector. These cassettes and vectors may be contained in a cell, such as a mammalian cell. A non-human mammal may contain the cassette or vector. The vector may contain two expression cassettes, the first expression cassette containing a nucleic acid encoding the first strand of the RNA duplex, and a second expression cassette containing a nucleic acid encoding the second strand of the RNA duplex.

The present invention further provides a method of substantially silencing a target gene of interest or targeted allele for the gene of interest in order to provide a therapeutic effect. As used herein the term "substantially silencing" or "substantially silenced" refers to decreasing, reducing, or inhibiting the expression of the target gene or target allele by at least about 5%, 10%, 15%, 20%, 25%, 30%, 35%, 40%, 45%, 50%, 55%, 60%, 65%, 70%, 75%, 80%, 85% to 100%. As used herein the term "therapeutic effect" refers to a change in the associated abnormalities of the disease state, including pathological and behavioral deficits; a change in the time to progression of the disease state; a reduction, lessening, or alteration of a symptom of the disease; or an improvement in the quality of life of the person afflicted with the disease. Therapeutic effect can be measured quantitatively by a physician or qualitatively by a patient afflicted with the disease state targeted by the siRNA. In certain embodiments wherein both the mutant and wild type allele are substantially silenced, the term therapeutic effect defines a condition in which silencing of the wild type allele's expression does not have a deleterious or harmful effect on normal functions such that the patient would not have a therapeutic effect.

In one embodiment, the expression vectors are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is flanked (5' and 3') with functional sequences, such as sequences encoding an aptamer and/or siRNA.

In one embodiment, the selected nucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, pol II promoters, pol III promoters, synthetic promoters, hybrid promoters, and the like. In addition, sequences derived from nonviral genes, such as the murine metallothionein gene, will also find use herein. Such promoter sequences are commercially available from, e.g., Stratagene® (San Diego, Calif.).

In one embodiment, pharmaceutical compositions will comprise sufficient genetic material to produce a therapeutically effective amount of the siRNA of interest, i.e., an amount sufficient to reduce or ameliorate symptoms of the disease state in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol.

Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in REMINGTON'S PHARMACEUTICAL SCIENCES (Mack Pub. Co., N.J. 1991).

BRIEF DESCRIPTION OF DRAWINGS

FIG. 1A. Thin line: sense strand of siRNA duplex. Thick line: anti-sense (silencing/guide) strand of siRNA duplex. FIG. 1B. depicts A10-Plk1 (duplex of SEQ ID NO: 15 and SEQ ID NO: 10), BLUNT (duplex of SEQ ID NO: 16 and SEQ ID NO: 10), OVH (duplex of SEQ ID NO: 17 and SEQ ID NO: 10), G-U (duplex of SEQ ID NO: 18 and SEQ ID NO: 10), Swap (duplex of SEQ ID NO: 19 and SEQ ID NO: 7), G-U/Swap (duplex of SEQ ID NO: 19 and SEQ ID NO: 6) and Stem Loop (SEQ ID NO: 21). Guide/silencing strand of siRNA duplex and Passenger strand are indicated.

FIG. 2A. PSMA-positive LNCaP cells and PSMA-negative PC-3 cells were incubated with either the full length PSMA aptamer A10-Plk1 (71nt) or truncated versions of the PSMA aptamer A10-3 (57nt), A10-3.2 (39nt). $^{32}$P-labeled bound/internalized RNAs were determined by Liquid Scintillation Counter (LSC) and/or filter binding assay. FIG. 2B. Relative affinity of A10 PSMA aptamer and truncated A10 aptamers to cells expressing PSMA. Varying amounts (0 to 2 nM) of end-labeled A10, A10-3, and A10-3.2 were incubated with fixed LNCaP cells. Bound/internalized counts were determined by filter binding assay. FIG. 2C. First generation chimera (A10-Plk1) and optimized chimeras were incubated with either PSMA-negative PC-3 cells or 2 PSMA-positive prostate cancer cell lines (LNCaP and 22Rv1 clone 1.7). Cells were processed as in part A. Bound counts were determined with LSC.

FIG. 3A. Comparison of silencing efficiency of BLUNT, OVH, G-U Wobble, Swap and Stem-Loop chimeras to that of first-generation chimera (A10-Plk1). FIG. 3A (Inset) % Plk1 expression of G-U Wobble, Swap and Stem-Loop≤1.0 and are depicted on an adjusted Y-axis. Experiments were performed several times (n=3). FIG. 3B. 22Rv1 (1.7) PSMA-positive prostate cancer cells were treated with either 400 nM or 4 nM of each of the optimized RNA chimeras in the absence of transfection reagent. Cells were processed for qRT-PCR 24-48 h following treatments.

FIG. 4A. In vitro Dicer processing. The $^{32}$P-labeled PSMA-Plk1 chimeras were incubated with recombinant human Dicer enzyme for either 1 hr or 2 hr. The Dicer cleavage products or uncleaved (No Dicer), were visualized following 20% non-denaturing PAGE. FIG. 4B Assessment of Strand Bias:

loading of siRNA silencing strand into RNA induced silencing complex (RISC). Small fragment northern blot of RNA isolated from LNCaP cells transfected with 200 pmols of each of the optimized aptamer-siRNA chimera constructs. Loading of the siRNA silencing strand into RISC protects the siRNA strand from degradation (this can be detected with a specific probe using a modified Northern blot assay). The strand that is not loaded is rapidly degraded. U6 RNA was used as a loading control. UNT, untransfected; Duplex, Plk1 siRNA duplex; A10-Plk1, first generation chimera. BLUNT, OVH, G-U, SWAP and Stem Loop chimeras are described in FIGS. 1A and 1B. Probe controls show hybridization efficiencies of the sense and anti-sense probes.

Figure 5A:
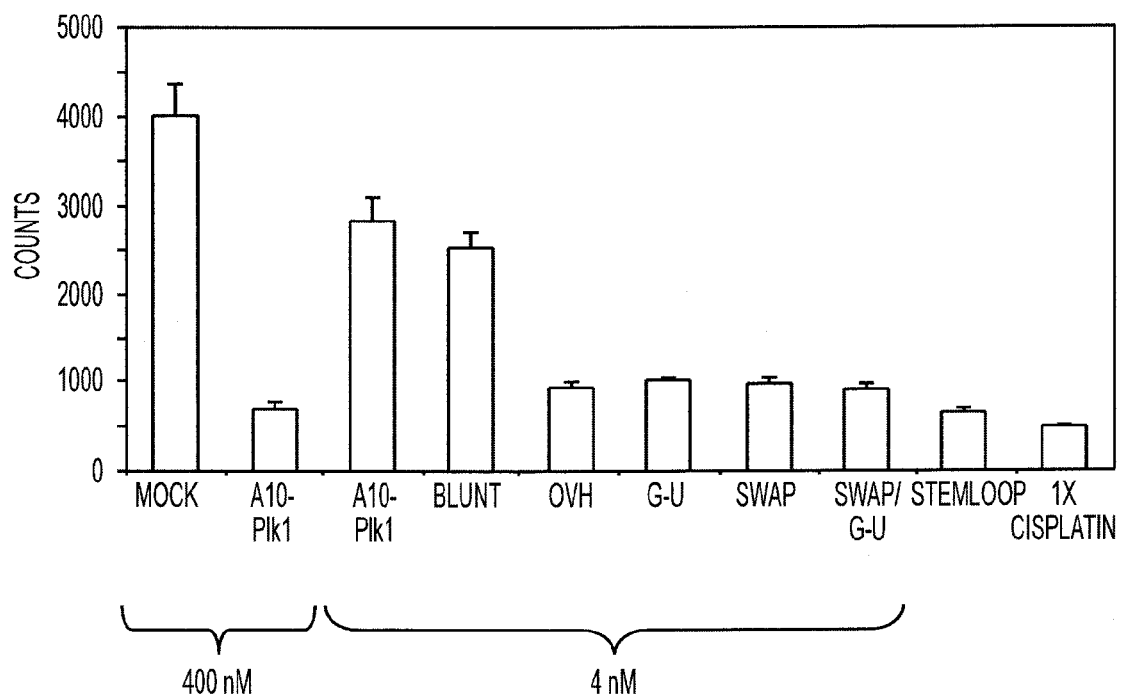
Figure 5B:
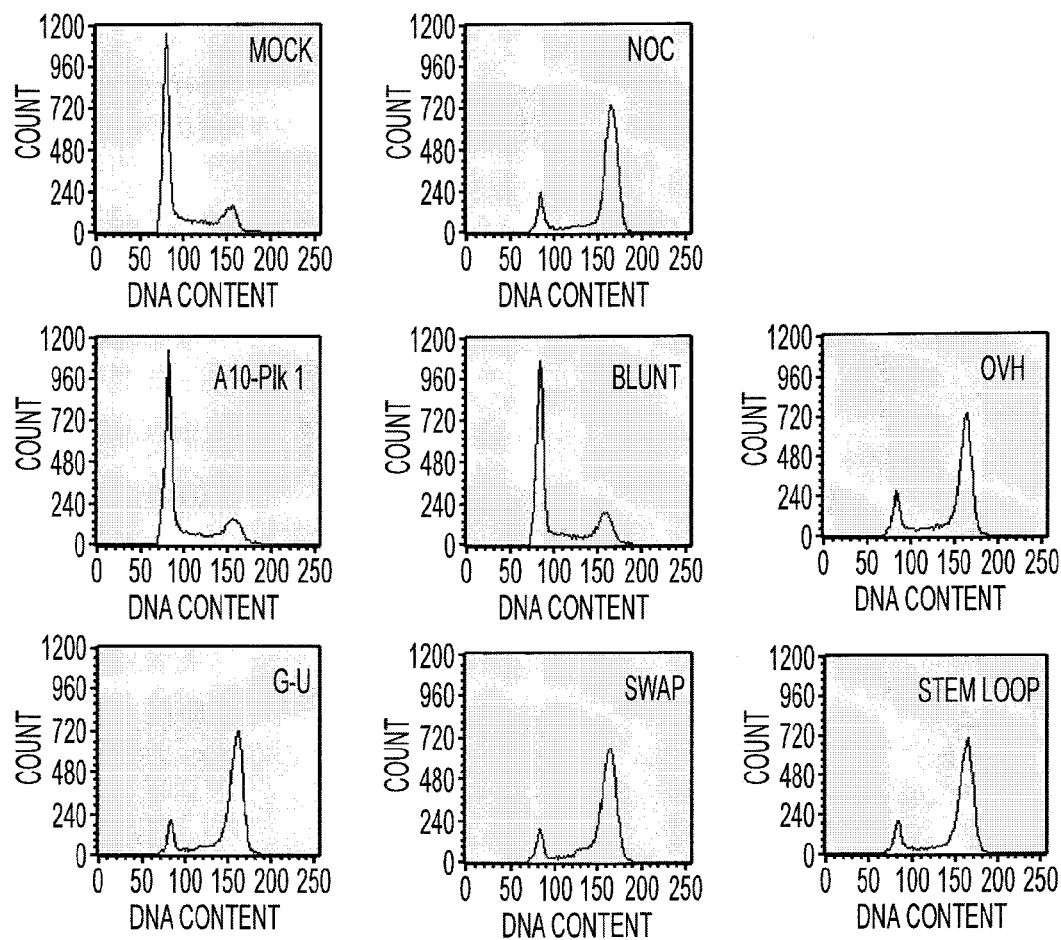
Figure 5C:
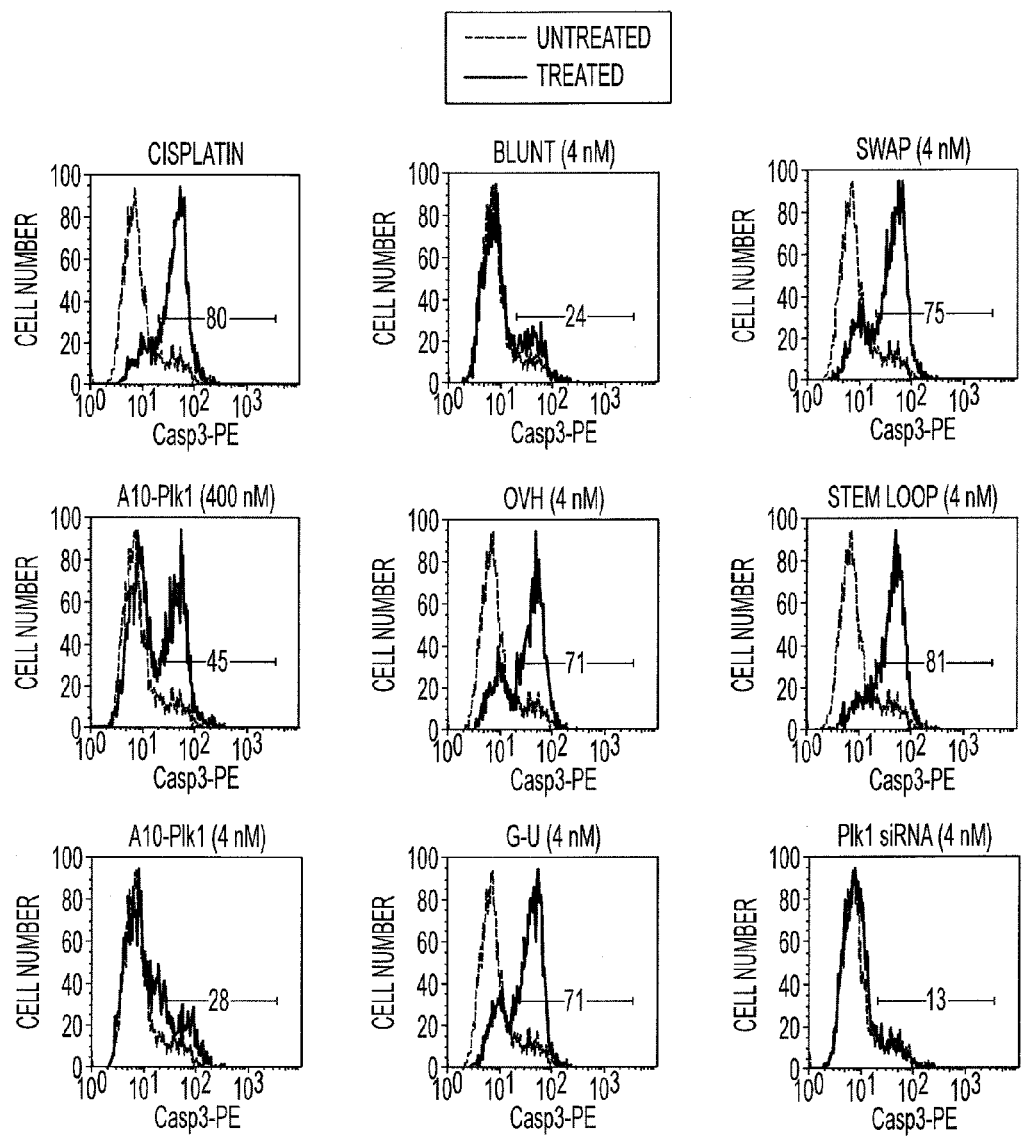

FIGS. 5A-5D. Effect of PSMA-Plk1 chimeras on prostate cancer cell growth. FIG. 5A. 22Rv1(1.7) PSMA-positive prostate cancer cells were treated with either 400 nM or 4 nM of A10-Plk1 or 4 nM of each of the optimized chimeras. $^3$H-thymidine was added to the media 24 h post treatment and cells were incubated in the presence of RNAs and $^3$H-thymidine for another 24 h. The next day cells were lysed with 0.5N NaOH and incorporated counts determined by liquid scintillation counter (LSC). Cisplatin was used as a positive control for this assay. FIG. 5B. Cell cycle profile of 22Rv1(1.7) cells transfected with 4 nM of each of the optimized chimeras. DNA content of treated cells was determined by flow cytometry 48 h post transfection after staining cells with Propidium Iodide. Nocodazole (Noc) treatment was used as a positive control for this assay to arrest cells in mitosis. FIG. 5C. Effect of Optimized PSMA chimeras on prostate cancer cell viability. 22Rv1(1.7) PSMA-positive prostate cancer cells were treated over the course of 5 days (Day 1 and Day 3) with either 400 or 4 nM of each chimera. Cells were collected on Day 5, stained with an antibody against active caspase 3, and processed for flow cytometry. Cisplatin was used as a positive control for this assay. UNT, untransfected; Plk1 siRNA duplex, A10-Plk1, first generation chimera; BLUNT, truncated version of first generation chimera; OVH, truncated version of first generation chimera containing 2nt overhangs at the 3' end; G-U, same as OVH chimera but with addition of a G-U wobble at the 5' end of antisense strand; SWAP, same as OVH but with sense and anti-sense strands swapped; Stem Loop, a hairpin RNA composed of the PSMA aptamer (loop) and a Plk1 siRNA (stem) (see FIGS. 1A and 1B). FIG. 5D. Effect of PSMA-Plk1 chimeras on prostate cancer cell viability. 22Rv1(1.7) PSMA-positive prostate cancer cells were incubated with either 400 nM or 4 nM of BLUNT chimera or 4 nM of each optimized chimera in the absence of transfection reagents. Media containing fresh RNAs was replaced every other day for the course of the experiment. Cells were collected on Day 6, stained with an antibody specific for active caspase 3, and processed for flow cytometry. Cisplatin was used as a positive control for apoptosis in this assay. Data was averaged from 2 independent experiments.

Figure 6A:
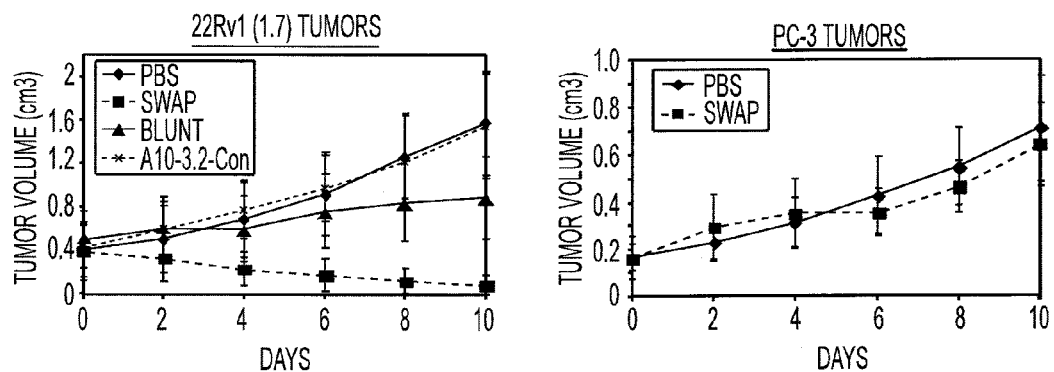
Figure 6B:
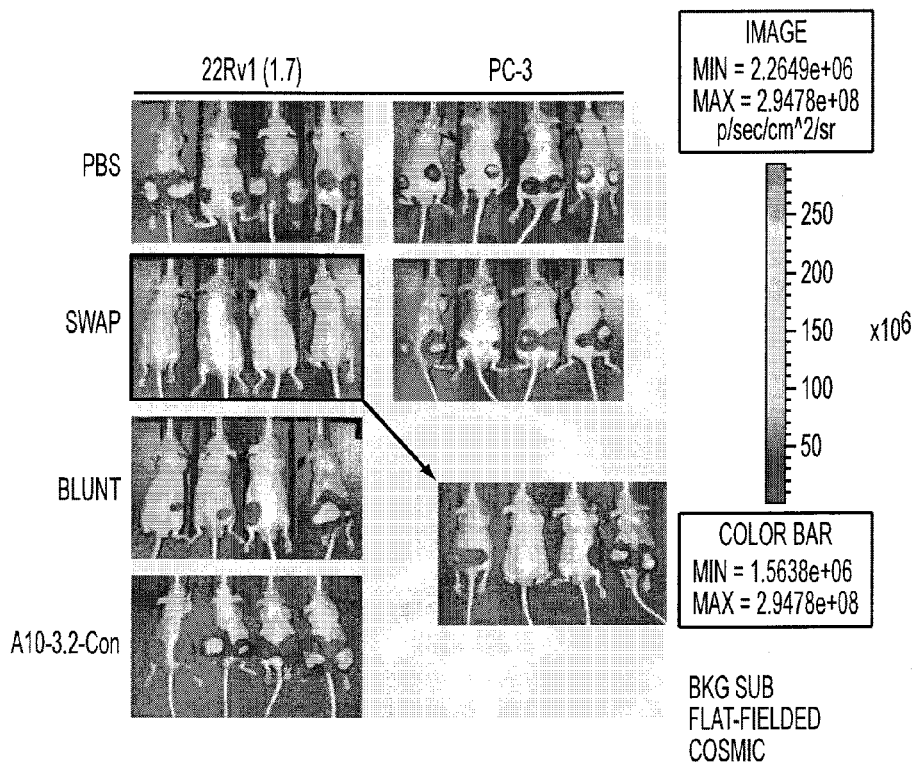
Figure 6C:
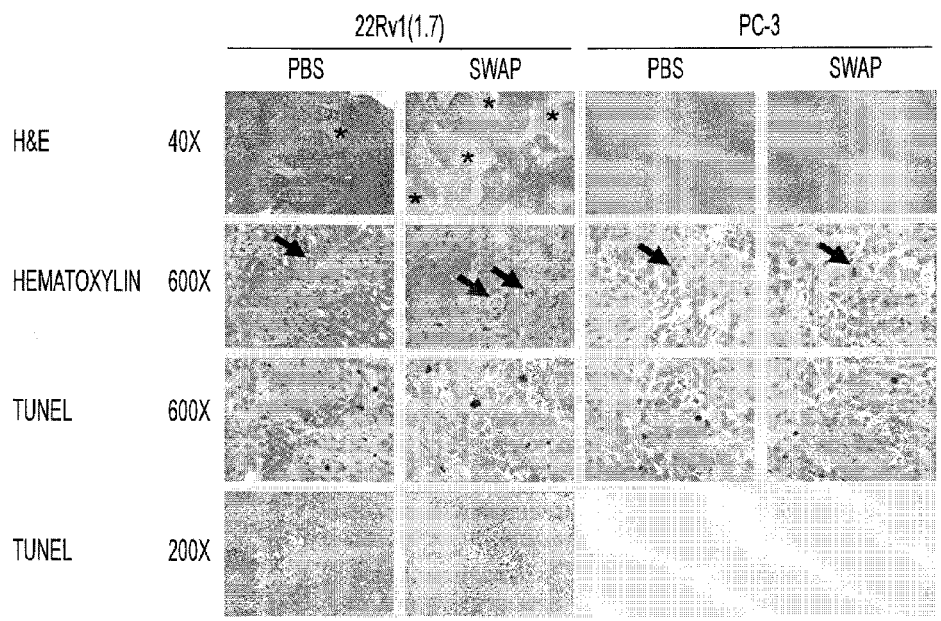
Figure 6D:
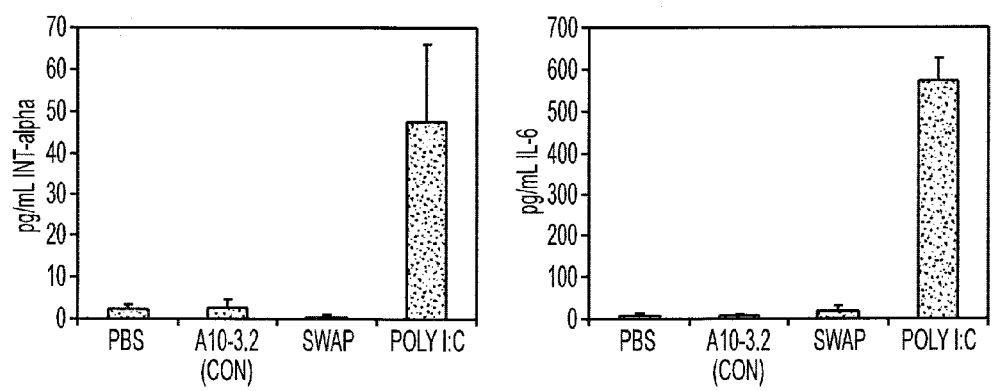
Figure 6E:
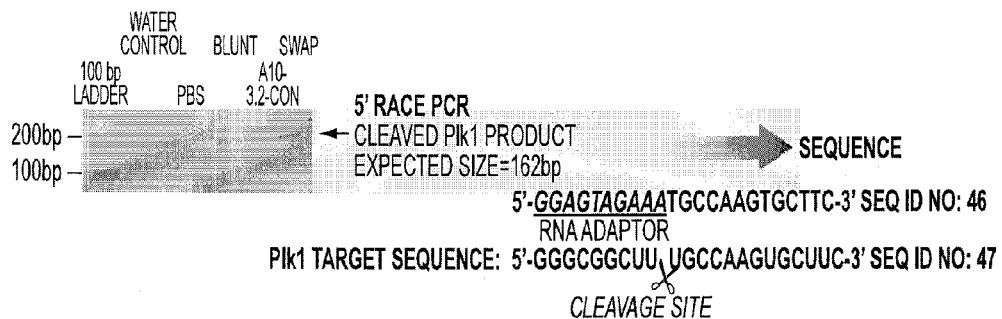
Figure 6F:
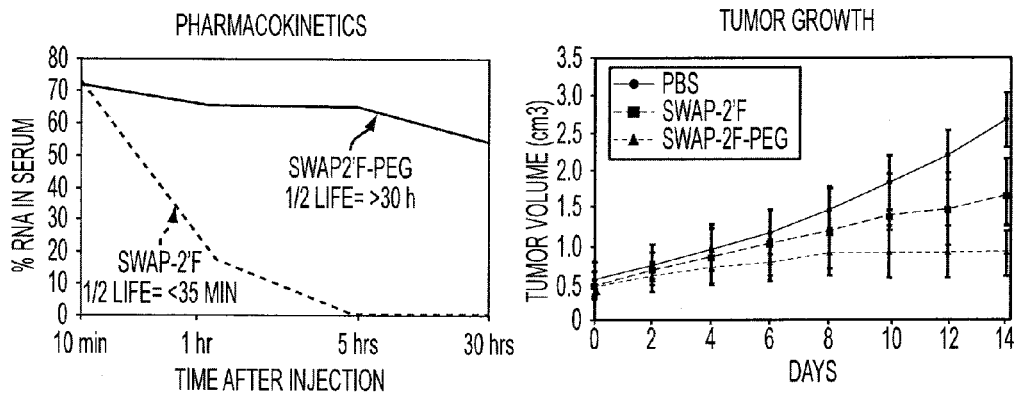
Figure 6G:
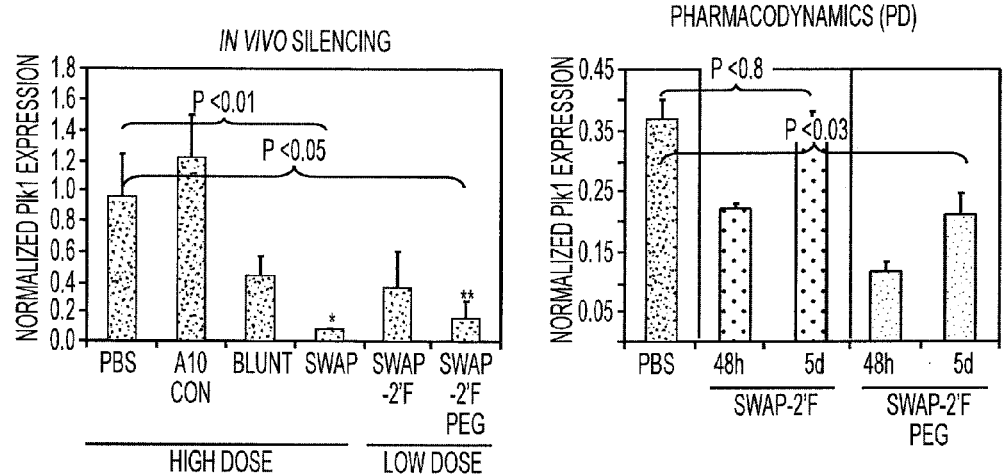

FIGS. 6A-6G. In vivo efficacy of optimized PSMA chimera in a xenograft model of prostate cancer. FIG. 6A. $1 \times 10^6$ luciferase expressing (PSMA-positive or PSMA-negative) prostate cancer cells were injected into the flanks of nude (nu/nu) mice two weeks prior to treatment with optimized chimeras. Treatment with the optimized chimeras was begun when tumors reached ~0.4 cm$^3$ in volume. 1nmol of either, BLUNT (Δ), SWAP (■), or a mutant control non-silencing chimera (A10-3.2-Con) (X) was administered intra-peritoneally (i.p.) in a mouse xenograft model of prostate cancer bearing 22Rv1(1.7) PSMA-positive prostate cancer cells. As a control for specificity, a mouse xenograft model of prostate cancer bearing PSMA-negative prostate cancer cells (PC-3) was also treated with the SWAP chimera (■). A total of 10 treatments were administered for each treatment group. Treatment occurred every day for 10 consecutive days. Tumors were measured with calipers every other day for the course of the experiment. Saline (PBS) treated animals were used as a control (♦). Animals were sacrificed 2 days after the last treatment. n≥10 tumors per treatment group. FIG. 6B. Bioluminescence imaging (BLI) of 22Rv1(1.7) (PSMA-positive) and PC3 (PSMA-negative) prostate tumors following treatment with optimized chimeras (Day 10). Examples show tumor growth in 4 representative animals from each treatment group. Insert indicated by arrow represents BLI images of ~30% of 22Rv1 tumors bearing mice treated with the SWAP chimera that still had palpable tumors (17 out of 48 total tumors) by Day 10. All sites represent tumor growth 25 days post-injection of tumor cells. Log scale heat map (right) of photon flux applies to all panels. FIG. 6C. Histology of 22Rv1 (1.7) and PC-3 tumors treated with the various optimized chimeras. Coalescing lakes of caseous necrosis (asterisks) were readily detected in SWAP treated 22Rv1(1.7) tumors, but uncommonly seen in PBS treated tumors (H&E, 40×). Mitotic figures (arrows) were often detected in tumors from all treatment groups including occasional large bizarre mitoses in SWAP treated 22Rv1(1.7) tumors (Hematoxylin, 600×). TUNEL staining was detected in scattered cells throughout the tumor section of each group (TUNEL staining, 600×) and at the interface of viable tissue and necrotic foci (TUNEL staining, 200×). Representative sections from the PBS and SWAP treatment groups are shown. FIG. 6D. Assessment of potential chimera-dependent immunostimulatory effects. Serum from mice treated with saline (PBS), A10-3.2-Con, SWAP, or polyinosinic:polycytidylic acid (poly I:C) was screened for levels of cytokines interferon-a (INT-a) and interleukin-6 (IL-6) using enzyme-linked immunosorbent assays (ELISAs). FIG. 6E. 5'-Rapid amplification of cDNA ends (5'-RACE) PCR analysis to assess siRNA mediated cleavage of Plk1 mRNA in tumors treated with the various PSMA-Plk1 chimeras. FIG. 6F. Pharmacokinetic profile and efficacy of the SWAP chimera with polyethylene glycol (PEG). FIG. 6G. In vivo silencing assessed by quantitative RT-PCR.

Figure 7:
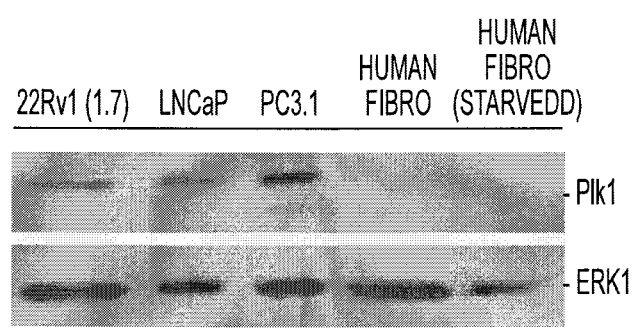

FIG. 7. Expression of Plk1 in prostate cancer cells. Three prostate cancer cell lines 22Rv1(1.7), LNCaP, and PC-3 cells were grown to confluence in a 60 mm dish and lysed with RIPA buffer containing protease inhibitors. Lysates were resolved on a PAGE gel, transferred to a PVDF membrane, and blotted for human Plk1 with a specific antibody. Normal human fibroblasts (fibro) were used as a control for this assay. Human fibroblasts were either starved for 48 h with media containing 0.2% serum or grown asynchronously. In normal cells Plk1 expression peaks during mitosis and is at its lowest during quiescence whereas cancer cells have intrinsically high levels of Plk1 expression. ERK1 was used as a loading control.

Figure 8A:
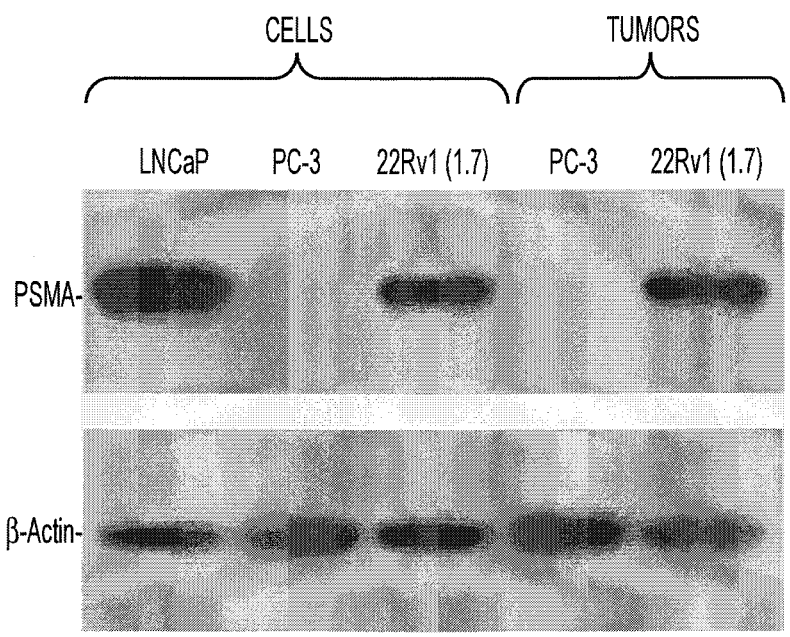
Figure 8B:
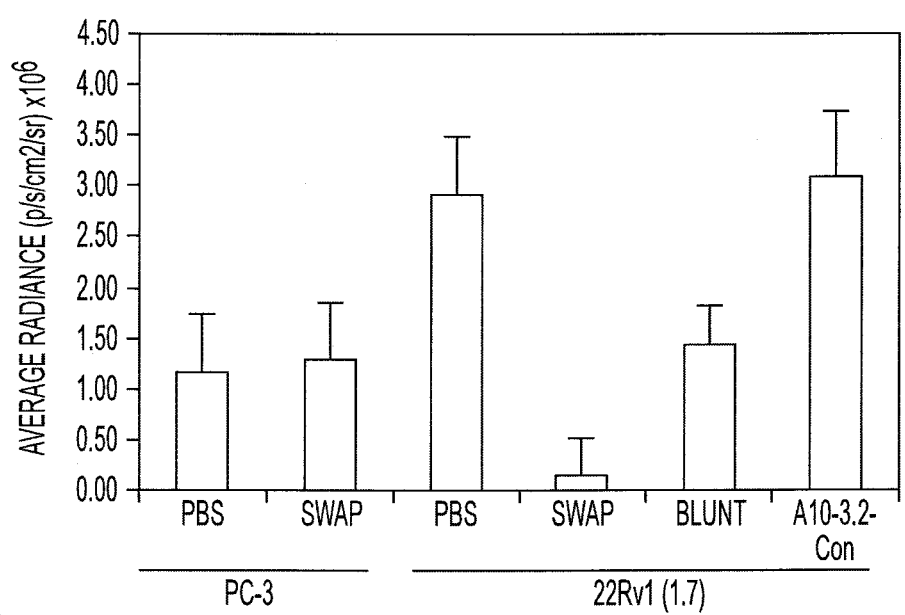

FIGS. 8A-8B. Assessment of PSMA expression and tumor volume measurements following treatment with PSMA-Plk1 chimeras using BLI. FIG. 8A. Protein lysates of prostate cancer cell lines 22Rv1(1.7), LNCaP, and PC-3 and prostate tumors derived from these cells were resolved on an SDS-PAGE gel, transferred to a PVDF membrane, and probed for human PSMA with a specific antibody and β-Actin as a loading control. FIG. 8B. Tumor volume measurements using Living Image® Software v2.50 (Xenogen). PSMA-positive (22Rv1) or PSMA-negative (PC-3) prostate cancer cells were injected into the flanks of nude (nu/nu) mice two weeks prior to treatment with optimized chimeras. After tumors reached ~~0.4 cm$^3$ in volume animals were injected (i.p.) daily for 10 days with saline (PBS) or 1nmol of the RNA chimeras (BLUNT, SWAP, or A10-3.2-Con). On Day 10 of treatment BLI images of the treated animals were obtained. Tumor volume was determined by placing a circular region of interest (ROI) around each tumor site and total flux quantified using Living Image® Software v2.50 (Xenogen) with the units being photons/sec/cm$^2$/sr. Average tumor volumes were plotted for each treatment group. Animals were sacrificed 2 days after the last treatment. n≥10 tumors per treatment group.

Figure 9B:
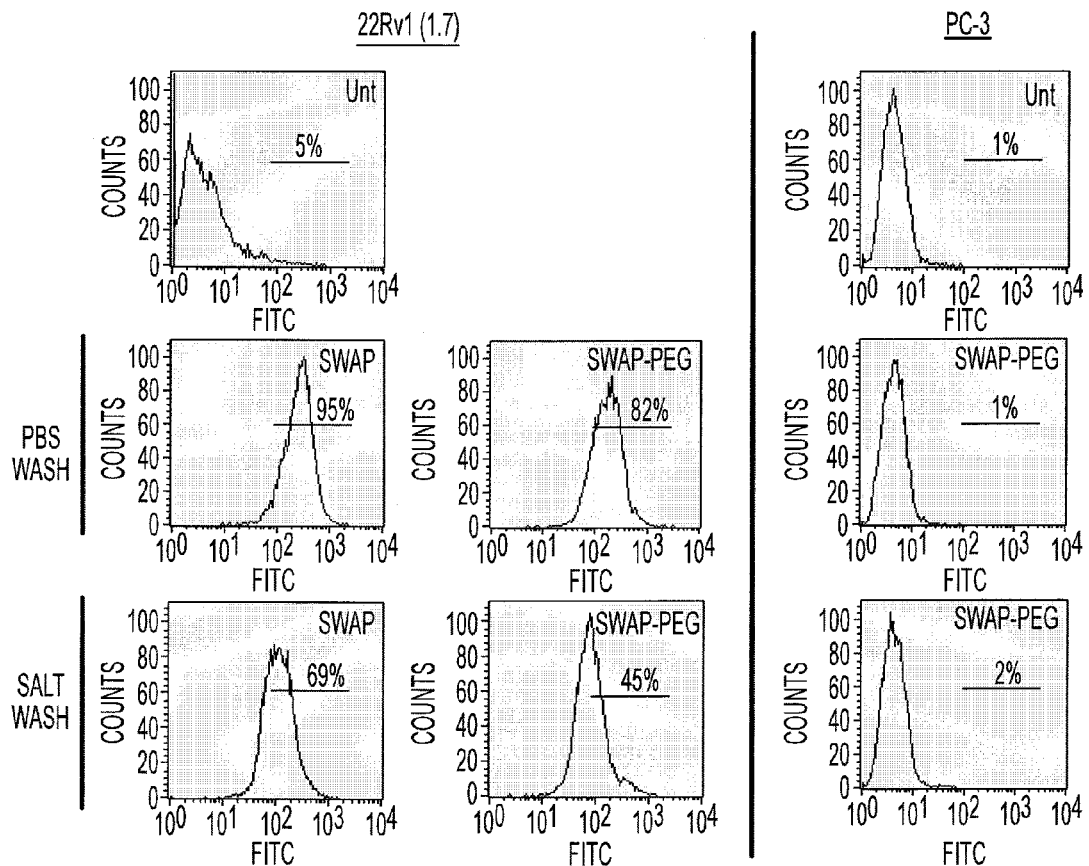

FIGS. 9A-9B. Targeted specificity and efficacy of PEGylated SWAP chimera (SWAP-PEG). FIG. 9A. PEG-modified SWAP chimera (SWAP-PEG) selectively internalizes into PSMA-positive cells. 22Rv1(1.7) PSMA-positive and PC-3 PSMA-negative prostate cancer cells were incubated at 37° C. with fluorescently labeled RNA chimeras. Cells were washed with PBS alone or PBS plus 0.5M NaCl (Salt wash) to remove surface bound RNAs. The amount of fluorescently labeled RNAs that bound and/or internalized into cells was quantitated using flow cytometry. FIG. 9B. PEG-modified SWAP chimera effectively silences PLK1 mRNA expression following internalization into PSMA-positive prostate cancer cells. 22Rv1(1.7) and PC-3 cells were incubated with media containing 100 nM of either the SWAP, SWAP-2'F or SWAP-2'F-PEG chimeras for 48 h. Cells were then processed for total RNA and quantitative RT-PCR was performed to assess Plk1 mRNA levels in treated cells. Plk1 mRNA levels were normalized against GAPDH.

DETAILED DESCRIPTION OF THE INVENTION

Modulation of gene expression by endogenous, noncoding RNAs is increasingly appreciated as a mechanism playing a role in eukaryotic development, maintenance of chromatin structure and genomic integrity. Recently, techniques have been developed to trigger RNA interference (RNAi) against specific targets in mammalian cells by introducing exogenously produced or intracellularly expressed siRNAs. These methods have proven to be quick, inexpensive and effective for knockdown experiments in vitro and in vivo. The ability to accomplish selective gene silencing has led to the hypothesis that siRNAs might be employed to suppress gene expression for therapeutic benefit.

Disclosed herein is a strategy that results in substantial silencing of targeted genes via RNAi. Use of this strategy results in markedly diminished in vitro and in vivo expression of targeted genes. This strategy is useful in reducing expression of targeted genes in order to model biological processes or to provide therapy for human diseases. For example, this strategy can be applied to a the treatment of cancer. As used herein the term "substantial silencing" means that the mRNA of the targeted gene is inhibited and/or degraded by the presence of the introduced siRNA, such that expression of the targeted gene is reduced by about 10% to 100% as compared to the level of expression seen when the siRNA is not present. Generally, when a gene is substantially silenced, it will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, 98%, 99% or even 100% reduction expression as compared to when the siRNA is not present. As used herein the term "substantially normal activity" means the level of expression of a gene when an siRNA has not been introduced to a cell.

An embodiment of the invention described herein is an optimized RNA-based therapeutic reagent for the treatment of prostate and possibly other solid sarcomas and carcinomas. This reagent consists of two basic components, an RNA aptamer (a structural, synthetic RNA) coupled to a small molecule. The aptamer portion of the reagent serves as a targeting moiety by binding specifically to a cell surface receptor (e.g., prostate specific membrane antigen; PSMA) expressed on cancer cells (e.g., prostate cancer cells).

Aptamer Portion

Aptamers are single stranded oligonucleotides that can naturally fold into different 3-dimensional structures, which have the capability of binding specifically to biosurfaces, a target compound or a moiety. The term "conformational change" refers to the process by which a nucleic acid, such as an aptamer, adopts a different secondary or tertiary structure. The term "fold" may be substituted for conformational change.

Aptamers have advantages over more traditional affinity molecules such as antibodies in that they are very stable, can be easily synthesized, and can be chemically manipulated with relative ease. Aptamer synthesis is potentially far cheaper and reproducible than antibody-based diagnostic tests. Aptamers are produced by solid phase chemical synthesis, an accurate and reproducible process with consistency among production batches. An aptamer can be produced in large quantities by polymerase chain reaction (PCR) and once the sequence is known, can be assembled from individual naturally occurring nucleotides and/or synthetic nucleotides. Aptamers are stable to long-term storage at room temperature, and, if denatured, aptamers can easily be renatured, a feature not shared by antibodies. Furthermore, aptamers have the potential to measure concentrations of ligand in orders of magnitude lower (parts per trillion or even quadrillion) than those antibody-based diagnostic tests. These characteristics of aptamers make them attractive for diagnostic applications.

Aptamers are typically oligonucleotides that may be single stranded oligodeoxynucleotides, oligoribonucleotides, or modified oligodeoxynucleotide or oligoribonucleotides. The term "modified" encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl-; 2-O-alkyl; 2-O-allyl; 2'-S-alkyl; 2'-S-allyl; 2'-fluoro-; 2'-halo or 2-azidoribose, carbocyclic sugar analogues a-anomeric sugars; epimeric sugars such as arabinose, xyloses or lyxoses, pyranose sugars, furanose sugars, and sedoheptulose.

Modified nucleotides are known in the art and include, by example and not by way of limitation, alkylated purines and/or pyrimidines; acylated purines and/or pyrimidines; or other heterocycles. These classes of pyrimidines and purines are known in the art and include, pseudoisocytosine; N4,N4-ethanocytosine; 8-hydroxy-N6-methyladenine; 4-acetylcytosine, 5-(carboxyhydroxylmethyl)uracil; 5-fluorouracil; 5-bromouracil; 5-carboxymethylaminomethyl-2-thiouracil; 5-carboxymethylaminomethyl uracil; dihydrouracil; inosine; N6-isopentyl-adenine; 1-methyladenine; 1-methylpseudouracil; 1-methylguanine; 2,2-dimethylguanine; 2-methyladenine;

2-methylguanine; 3-methylcytosine; 5-methylcytosine; N6-methyladenine; 7-methylguanine; 5-methylaminomethyl uracil; 5-methoxy amino methyl-2-thiouracil; β-D-mannosylqueosine; 5-methoxycarbonylmethyluracil; 5-methoxyuracil; 2-methylthio-N6-isopentenyladenine; uracil-5-oxyacetic acid methyl ester; psueouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6,-diaminopurine; methylpsuedouracil; 1-methylguanine; 1-methylcytosine.

The aptamers of the invention are synthesized using conventional phosphodiester linked nucleotides and synthesized using standard solid or solution phase synthesis techniques which are known in the art. Linkages between nucleotides may use alternative linking molecules. For example, linking groups of the formula P(O)S, (thioate); P(S)S, (dithioate); P(O)NR'2; P(O)R; P(O)OR6; CO; or CONR'2 wherein R is H (or a salt) or alkyl (1-12C) and R6 is alkyl (1-9C) is joined to adjacent nucleotides through —O— or —S—.

In certain embodiments of the present invention, the aptamer portion binds to Prostate-Specific Mediated Antigen (PSMA). In the literature, a PSMA aptamer of 71 nucleotides (A10-Plk1) was described (Lupold et al., Cancer Res. 62(14): 4029-33 (2002)). Surprisingly, the inventors were able to shorten the A10-Plk1 aptamer down to 39 nucleotides (A10-3.2), and still have effective binding activity. In certain embodiments, additional modifications are made to the aptamer portion. Additional modifications to the aptamer portion include 2'O-methyl modification of the pyrimidines. In other embodiments, all of the nucleotides in the aptamer are 2'O-methyl modified. Alternatively, the pyrimidines, or all the nucleotides, may be modified with 2'fluoros (both pyrimidines and purines). Additional modifications to the nucleotides in the aptamer include large molecular weight conjugates like pegylation, lipid-based modifications (e.g., cholesterol) or nanoparticles (e.g., PEI or chitosan) to improve the pharmacokinetic/dynamic profile of the chimera.

Prostate-specific membrane antigen (PSMA) is expressed extracellularly on prostate cancer cells (and other solid tumors, such as renal cancer cells) and the endothelial cells of new blood vessels that supply most other solid tumors. However, it has also been shown to be present at low levels in the brain, kidneys (brush border of proximal tubes) and liver. One advantage of targeting PSMA is that it is a transmembrane protein, and is not secreted. The truncated PSMA aptamer can be used as a tool to target prostate cancer as well as the vasculature of all solid sarcomas and carcinomas. It has been previously shown that PSMA expression is elevated in malignant prostate disease as well as tumor vasculature.

In certain embodiments, modifications are introduced into the stem sequence in the aptamer. Different nucleotides can be used as long as the structure of the stem is retained.

Small Molecule Portion

The aptamers of the present invention can be operably linked to one or more small molecule entities. In certain embodiments, the entity is a fluorescent tag, affinity tag, a protein, a solid substrate, a cell surface, or a cellular component. In certain embodiments, the cellular component is a cell wall or cell membrane. In certain embodiments, the solid substrate is a component of silica, cellulose, cellulose acetate, nitrocellulose, nylon, polyester, polyethersulfone, polyolefin, or polyvinylidene fluoride, or combinations thereof. In certain embodiments, the solid substrate is a filter, magnetic bead, metal oxide, latex particle, microtiter plates, polystyrene bead, or CD-ROM.

In certain embodiments, the aptamer is linked to the entity by means of a linker. In certain embodiments, the linker is a binding pair. In certain embodiments, the "binding pair" refers to two molecules which interact with each other through any of a variety of molecular forces including, for example, ionic, covalent, hydrophobic, van der Waals, and hydrogen bonding, so that the pair have the property of binding specifically to each other. Specific binding means that the binding pair members exhibit binding to each other under conditions where they do not bind to another molecule. Examples of binding pairs are biotin-avidin, hormone-receptor, receptor-ligand, enzyme-substrate, IgG-protein A, antigen-antibody, and the like. In certain embodiments, a first member of the binding pair comprises avidin or streptavidin and a second member of the binding pair comprises biotin. In certain embodiments, the aptamer is linked to the entity by means of a covalent bond.

The entity, for example, may additionally or alternatively, be a detection means. A number of "molecular beacons" (such as fluorescence compounds) can be attached to aptamers to provide a means for signaling the presence of and quantifying a target chemical or biological agent. Other exemplary detection labels that could be attached to the aptamers include biotin, any fluorescent dye, amine modification, horseradish peroxidase, alkaline phosphatase, etc.

In certain embodiments, the aptamer is operably linked to a detection means and to a solid substrate. For example, the aptamer may be linked to a fluorescent dye and to a magnetic bead.

The small molecule portion of the ligand can be siRNA sequences, miRNAs, small molecule inhibitors, chelators for housing radionuclides (for diagnostic/imaging applications as well as development of targeted radiotherapies), nanoparticles containing all of the above plus DNA vectors and/or mRNA sequences, depending on the use of the ligand as a diagnostic agent or as a therapeutic agent. In certain embodiments, the small molecule is an RNAi molecule, such as an siRNA or an miRNA. The RNAi portion, upon delivery to the targeted cells, induces the depletion of cancer cell survival factors, leading to the death of the cancer cells. In certain embodiments, the siRNA portion binds to polo-like kinase 1 (Plk1) within the cell, inhibiting the gene's activity. After the aptamer binds PSMA expressed on the surface of the cell, the complex, A10-3.2-Plk1 is taken into the cell by endocytosis. The molecule is then cleaved by Dicer, an endonuclease, and is incorporated into the RNA-Induced Silencing Complex (RISC) where it mediates Plk1 degradation.

A first generation of this reagent was previously described in the literature (McNamara et al., Nat Biotechnol. 24(8): 1005-15 (2006)). In certain embodiments, the invention encompasses a truncated RNA aptamer, which when compared to the original, longer RNA, is significantly less expensive to produce and an siRNA portion that has been optimized for activity. This optimized reagent surprisingly has a 100-fold greater activity than the first generation reagent when tested in cell culture. These advances result in a cancer therapeutic that is effective at significantly lower doses than the first generation reagent, thus reducing treatment costs as well as the likelihood for toxic side-effects.

Linking Molecules

Chemistries that can be used to link molecules to the aptamer are known in the art, such as disulfide linkages, amino linkages, covalent linkages, etc. Additional linkages and modifications can be found on the world-wide-web at trilinkbiotech.com/products/oligo/oligo_modifications.asp.

Detection and Amplification Methods

The present invention provides methods for detecting PSMA in a sample or in vivo. For example, one can contact a sample with an aptamer as described herein or the composition as described herein to form bound PSMA, and detecting the presence or the quantity of bound PSMA. Alternatively, aptamers or compositions can be administered in vivo to a patient (e.g. injected in situ into a tumor). In certain embodiments, the bound PSMA is detected by means of PCR, nuclear magnetic resonance, fluorescent capillary electrophoresis, lateral flow devices, colorimetry, chemiluminescence, fluorescence, southsester blots, microarrays, or ELISA.

In one embodiment of the present invention, the method also involves contacting the sample with at least one aptamer to form a hybridized nucleic acid and detecting the hybridized nucleic acid. In one embodiment, the detection is by amplification. "Amplifying" utilizes methods such as the polymerase chain reaction (PCR), ligation amplification (or ligase chain reaction, LCR), strand displacement amplification, nucleic acid sequence-based amplification, and amplification methods based on the use of Q-beta replicase. These methods are well known and widely practiced in the art. Reagents and hardware for conducting PCR are commercially available. In one embodiment of the present invention, at least one type of aptamer is immobilized on a solid surface.

The methods of the present invention can be used to detect the presence of PSMA in a sample.

According to the methods of the present invention, the amplification of PSMA present in a sample may be carried out by any means known to the art. Examples of suitable amplification techniques include, but are not limited to, polymerase chain reaction (including, for RNA amplification, reverse-transcriptase polymerase chain reaction), ligase chain reaction, strand displacement amplification, transcription-based amplification, self-sustained sequence replication (or "3SR"), the Qβ replicase system, nucleic acid sequence-based amplification (or "NASBA"), the repair chain reaction (or "RCR"), and boomerang DNA amplification (or "BDA").

The bases incorporated into the amplification product may be natural or modified bases (modified before or after amplification), and the bases may be selected to optimize subsequent electrochemical detection steps.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized that is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques. Where the nucleic acid to be amplified is RNA, amplification may be carried out by initial conversion to DNA by reverse transcriptase in accordance with known techniques.

Strand displacement amplification (SDA) may be carried out in accordance with known techniques. For example, SDA may be carried out with a single amplification primer or a pair of amplification primers, with exponential amplification being achieved with the latter. In general, SDA amplification primers comprise, in the 5' to 3' direction, a flanking sequence (the DNA sequence of which is noncritical), a restriction site for the restriction enzyme employed in the reaction, and an oligonucleotide sequence (e.g., an oligonucleotide probe of the present invention) that hybridizes to the target sequence to be amplified and/or detected. The flanking sequence, which serves to facilitate binding of the restriction enzyme to the recognition site and provides a DNA polymerase priming site after the restriction site has been nicked, is about 15 to 20 nucleotides in length in one embodiment. The restriction site is functional in the SDA reaction. The oligonucleotide probe portion is about 13 to 15 nucleotides in length in one embodiment of the invention.

Ligase chain reaction (LCR) is also carried out in accordance with known techniques. In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

Diagnostic techniques that are useful in the methods of the invention include, but are not limited to direct DNA sequencing, pulsed-field gel electrophoresis (PFGE) analysis, allele-specific oligonucleotide (ASO), dot blot analysis and denaturing gradient gel electrophoresis, and are well known to the artisan.

The sample may be contacted with the aptamer in any suitable manner known to those skilled in the art. For example, the sample may be solubilized in solution, and contacted with the aptamer by solubilizing the aptamer in solution with the sample under conditions that permit binding. Suitable conditions are well known to those skilled in the art. Alternatively, the sample may be solubilized in solution with the aptamer immobilized on a solid support, whereby the sample may be contacted with the aptamer by immersing the solid support having the aptamer immobilized thereon in the solution containing the sample.

General Terminology

"Synthetic" aptamers are those prepared by chemical synthesis. The aptamers may also be produced by recombinant nucleic acid methods. "Recombinant nucleic molecule" is a combination of nucleic sequences that are joined together using recombinant nucleic technology and procedures used to join together nucleic sequences known in the art.

The term "chimeric" refers to a gene or DNA that contains 1) DNA sequences, including regulatory and coding sequences that are not found together in nature or 2) sequences encoding parts of proteins not naturally adjoined, or 3) parts of promoters that are not naturally adjoined. Accordingly, a chimeric gene may include regulatory sequences and coding sequences that are derived from different sources, or include regulatory sequences and coding sequences derived from the same source, but arranged in a manner different from that found in nature.

As used herein, the term "nucleic acid" and "polynucleotide" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides.

Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

A "nucleic acid fragment" is a portion of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" may also be used interchangeably with gene, cDNA, DNA and RNA encoded by a gene, e.g., genomic DNA, and even synthetic DNA sequences. The term also includes sequences that include any of the known base analogs of DNA and RNA.

By "fragment" or "portion" is meant a full length or less than full length of the nucleotide sequence.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have in at least one embodiment 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

The term "gene" is used broadly to refer to any segment of nucleic acid associated with a biological function. Genes include coding sequences and/or the regulatory sequences required for their expression. For example, gene refers to a nucleic acid fragment that expresses mRNA, functional RNA, or a specific protein, including its regulatory sequences. Genes also include nonexpressed DNA segments that, for example, form recognition sequences for other proteins.

Genes can be obtained from a variety of sources, including cloning from a source of interest or synthesizing from known or predicted sequence information, and may include sequences designed to have desired parameters. In addition, a "gene" or a "recombinant gene" refers to a nucleic acid molecule comprising an open reading frame and including at least one exon and (optionally) an intron sequence. The term "intron" refers to a DNA sequence present in a given gene which is not translated into protein and is generally found between exons.

"Naturally occurring," "native" or "wild type" is used to describe an object that can be found in nature as distinct from being artificially produced. For example, a nucleotide sequence present in an organism (including a virus), which can be isolated from a source in nature and which has not been intentionally modified in the laboratory, is naturally occurring. Furthermore, "wild-type" refers to the normal gene, or organism found in nature without any known mutation.

"Homology" refers to the percent identity between two polynucleotides or two polypeptide sequences. Two DNA or polypeptide sequences are "homologous" to each other when the sequences exhibit at least about 75% to 85% (including 75%, 76%, 77%, 78%, 79%, 80%, 81%, 82%, 83%, 84%, and 85%), at least about 90%, or at least about 95% to 99% (including 95%, 96%, 97%, 98%, 99%) contiguous sequence identity over a defined length of the sequences.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences.

Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Software for performing BLAST analyses is publicly available through the National Center for Biotechnology Information (see the World Wide Web at ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When using BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the World Wide Web at ncbi.nlm.nih.gov. Alignment may also be performed manually by visual inspection.

For purposes of the present invention, comparison of nucleotide sequences for determination of percent sequence identity to the sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by a BLAST program.

(c) As used herein, "sequence identity" or "identity" in the context of two nucleic acid sequences makes reference to a specified percentage of residues in the two sequences that are the same when aligned for maximum correspondence over a specified comparison window, as measured by sequence comparison algorithms or by visual inspection. When percentage of sequence identity is used in reference to proteins, it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%; at least 80%, 81%, 82%, 83%, 84%, 85%, 86%, 87%, 88%, or 89%; at least 90%, 91%, 92%, 93%, or 94%; or even at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code.

(e)(ii) For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched nucleic acid. Specificity is typically the function of post-hybridization washes, the critical factors being the ionic strength and temperature of the final wash solution. For DNA-DNA hybrids, the $T_m$ can be approximated from the equation of Meinkoth and Wahl: $T_m$ 81.5° C.+16.6 (log M)+0.41 (% GC)−0.61 (% form)−500/L. M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide In general, a signal to noise ratio of 2× (or higher) than that observed for an unrelated probe in the particular hybridization assay indicates detection of a specific hybridization.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

"Operably-linked" nucleic acids refers to the association of nucleic acid sequences on single nucleic acid fragment so that the function of one is affected by the other, e.g., an arrangement of elements wherein the components so described are configured so as to perform their usual function. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. Control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

The terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. For example, "isolated nucleic acid" may be a DNA molecule containing less than 31 sequential nucleotides that is transcribed into an RNAi molecule. Such an isolated RNAi molecule may, for example, form a hairpin structure with a duplex 21 base pairs in length that is complementary or hybridizes to a sequence in a gene of interest, and remains stably bound under stringent conditions (as defined by methods well known in the art, e.g., in Sambrook and Russell, 2001). Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

In addition to a DNA sequence encoding a siRNA, the nucleic acid molecules of the invention include double-stranded interfering RNA molecules, which are also useful to inhibit expression of a target gene.

As used herein, the term "recombinant nucleic acid," e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome that has not been transformed with exogenous DNA. An example of preselected DNA "derived" from a source would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. Therefore, "recombinant DNA" includes completely synthetic DNA sequences, semi-synthetic DNA sequences, DNA sequences isolated from biological sources, and DNA sequences derived from RNA, as well as mixtures thereof.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

The terms "protein," "peptide" and "polypeptide" are used interchangeably herein. As used herein, the terms "a" or "an" are used to mean "one or more."

To accomplish intracellular expression of the therapeutic RNAi molecules, an RNA molecule is constructed containing two complementary strands or a hairpin sequence (such as a 21-bp hairpin) representing sequences directed against the gene of interest. The RNAi molecule, or a nucleic acid encoding the RNAi molecule, is introduced to the target cell, such as a diseased brain cell. The RNAi molecule reduces target mRNA and protein expression.

The construct encoding the therapeutic RNAi molecule is configured such that the one or more strands of the RNAi molecules are encoded by a nucleic acid that is immediately contiguous to a promoter. In one example, the promoter is a pol II promoter. If a pol II promoter is used in a particular construct, it is selected from readily available pol II promoters known in the art, depending on whether regulatable, inducible, tissue or cell-specific expression of the siRNA is desired. The construct is introduced into the target cell, allowing for diminished target-gene expression in the cell.

The present invention provides an expression cassette containing an isolated nucleic acid sequence encoding an RNAi molecule targeted against a gene of interest. The RNAi molecule may form a hairpin structure that contains a duplex structure and a loop structure. The loop structure may be the aptamer portion. The duplex is less than 30 nucleotides in length, such as from 19 to 25 nucleotides. The RNAi molecule may further contain an overhang region. Such an overhang may be a 3' overhang region or a 5' overhang region. The overhang region may be, for example, from 1 to 6 nucleotides in length. The expression cassette may further contain a pol II promoter, as described herein. Examples of pol II promoters include regulatable promoters and constitutive promoters. For example, the promoter may be a CMV or RSV promoter. The expression cassette may further contain a polyadenylation signal, such as a synthetic minimal polyadenylation signal. The nucleic acid sequence may further contain a marker gene or stuffer sequences. The expression cassette may be contained in a viral vector. An appropriate viral vector for use in the present invention may be an adenoviral, lentiviral, adeno-associated viral (AAV), poliovirus, herpes simplex virus (HSV) or murine Maloney-based viral vector. The gene of interest may be a gene associated with a condition amenable to siRNA therapy. Examples of such conditions include neurodegenerative diseases, such as a trinucleotide-repeat disease (e.g., polyglutamine repeat disease). Examples of these diseases include Huntington's disease or several spinocerebellar ataxias. Alternatively, the gene of interest may encode a ligand for a chemokine involved in the migration of a cancer cell, or a chemokine receptor.

The present invention also provides an expression cassette containing an isolated nucleic acid sequence encoding a first segment, a second segment located immediately 3' of the first segment, and a third segment located immediately 3' of the second segment, wherein the first and third segments are each less than 30 base pairs in length and each more than 10 base pairs in length, and wherein the sequence of the third segment is the complement of the sequence of the first segment, and wherein the isolated nucleic acid sequence functions as an RNAi molecule targeted against a gene of interest. The expression cassette may be contained in a vector, such as a viral vector.

The present invention provides a method of reducing the expression of a gene product in a cell by contacting a cell with an expression cassette described above. It also provides a method of treating a patient by administering to the patient a composition of the expression cassette described above.

The present invention further provides a method of reducing the expression of a gene product in a cell by contacting a cell with an expression cassette containing an isolated nucleic acid sequence encoding a first segment, a second segment located immediately 3' of the first segment, and a third segment located immediately 3' of the second segment, wherein the first and third segments are each less than 30 base pairs in length and each more than 10 base pairs in length, and wherein the sequence of the third segment is the complement of the sequence of the first segment, and wherein the isolated nucleic acid sequence functions as an RNAi molecule targeted against a gene of interest.

The present method also provides a method of treating a patient, by administering to the patient a composition containing an expression cassette, wherein the expression cassette contains an isolated nucleic acid sequence encoding a first segment, a second segment located immediately 3' of the first segment, and a third segment located immediately 3' of the second segment, wherein the first and third segments are each less than 30 bases in length and each more than 10 bases in length, and wherein the sequence of the third segment is the complement of the sequence of the first segment, and wherein the isolated nucleic acid sequence functions as an RNAi molecule targeted against a gene of interest.

An RNAi molecule may be a "small interfering RNA" or "short interfering RNA" or "siRNA" or "short hairpin RNA" or "shRNA" or "microRNA" or "miRNA." An RNAi molecule an RNA duplex of nucleotides that is targeted to a nucleic acid sequence of interest. As used herein, the term "RNAi molecule" is a generic term that encompasses the subset of shRNAs. A "RNA duplex" refers to the structure formed by the complementary pairing between two regions of a RNA molecule. RNAi molecule is "targeted" to a gene in that the nucleotide sequence of the duplex portion of the RNAi molecule is complementary to a nucleotide sequence of the targeted gene. In certain embodiments, the RNAi molecules are targeted to the sequence encoding Plk1. In some embodiments, the length of the duplex of RNAi molecules is less than 30 base pairs. In some embodiments, the duplex can be 29, 28, 27, 26, 25, 24, 23, 22, 21, 20, 19, 18, 17, 16, 15, 14, 13, 12, 11 or 10 base pairs in length. In some embodiments, the length of the duplex is 19 to 25 base pairs in length. In certain embodiment, the length of the duplex is 19 or 21 base pairs in length. The RNA duplex portion of the RNAi molecule can be part of a hairpin structure. In addition to the duplex portion, the hairpin structure may contain a loop portion positioned between the two sequences that form the duplex. In certain embodiments, the loop is 9 nucleotides in length. The hairpin structure can also contain 3' or 5' overhang portions. In some embodiments, the overhang is a 3' or a 5' overhang 0, 1, 2, 3, 4 or 5 nucleotides in length.

A "small interfering" or "short interfering RNA" or siRNA is a RNA duplex of nucleotides that is targeted to a gene interest. A "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length. The "sense" and "antisense" sequences can be attached to the aptamer portion to form aptamer chimeras. As used herein, the term RNAi molecule is meant to be equivalent to other terms used to describe nucleic acid molecules that are capable of mediating sequence specific RNAi, for example, double-stranded RNA (dsRNA), micro-RNA (miRNA), short hairpin RNA (shRNA), short interfering oligonucleotide, short interfering nucleic acid, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetic silencing. In a non-limiting example, modulation of gene expression by siRNA molecules of the invention can result from siRNA mediated cleavage of RNA (either coding or non-coding RNA) via RISC, or alternately, translational inhibition as is known in the art.

The RNAi molecule can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

The RNAi molecule can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

"Knock-down," "knock-down technology" refers to a technique of gene silencing in which the expression of a target gene is reduced as compared to the gene expression prior to the introduction of the RNAi molecule, which can lead to the inhibition of production of the target gene product. The term "reduced" is used herein to indicate that the target gene expression is lowered by 1-100%. In other words, the amount of RNA available for translation into a polypeptide or protein is minimized. For example, the amount of protein may be reduced by 10, 20, 30, 40, 50, 60, 70, 80, 90, 95, or 99%. In some embodiments, the expression is reduced by about 90% (i.e., only about 10% of the amount of protein is observed a cell as compared to a cell where RNAi molecules have not been administered). Knock-down of gene expression can be directed, for example, by the use of dsRNAs, siRNAs or miRNAs.

"RNA interference (RNAi)" is the process of sequence-specific, post-transcriptional gene silencing initiated by an RNAi molecule. During RNAi, RNAi molecules induce degradation of target mRNA with consequent sequence-specific inhibition of gene expression. RNAi involving the use of RNAi molecules has been successfully applied to knockdown the expression of specific genes in plants, *D. melanogaster, C. elegans*, trypanosomes, planaria, hydra, and several vertebrate species including the mouse.

According to a method of the present invention, the expression of PLK1 can be modified via RNAi. For example, the accumulation of PLK1 can be suppressed in a cell. The term "suppressing" refers to the diminution, reduction or elimination in the number or amount of transcripts present in a particular cell. For example, the accumulation of mRNA encoding PLK1 can be suppressed in a cell by RNA interference (RNAi), e.g., the gene is silenced by sequence-specific double-stranded RNA (dsRNA), which is also called short interfering RNA (siRNA). These siRNAs can be two separate RNA molecules that have hybridized together, or they may be a single hairpin wherein two portions of a RNA molecule have hybridized together to form a duplex.

The terms "protein," "peptide" and "polypeptide" are used interchangeably herein.

"Recombinant DNA molecule" is a combination of DNA sequences that are joined together using recombinant DNA technology and procedures used to join together DNA sequences as described, for example, in Sambrook and Russell (2001).

The terms "heterologous gene," "heterologous DNA sequence," "exogenous DNA sequence," "heterologous RNA sequence," "exogenous RNA sequence" or "heterologous nucleic acid" each refer to a sequence that either originates from a source foreign to the particular host cell, or is from the same source but is modified from its original or native form.

Thus, a heterologous gene in a host cell includes a gene that is endogenous to the particular host cell but has been modified through, for example, the use of DNA shuffling. The terms also include non-naturally occurring multiple copies of a naturally occurring DNA or RNA sequence. Thus, the terms refer to a DNA or RNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA or RNA sequence is a sequence that is naturally associated with a host cell into which it is introduced.

"Genome" refers to the complete genetic material of an organism.

A "vector" is defined to include, inter alia, any viral vector, as well as any plasmid, cosmid, phage or binary vector in double or single stranded linear or circular form that may or may not be self transmissible or mobilizable, and that can transform prokaryotic or eukaryotic host either by integration into the cellular genome or exist extrachromosomally (e.g., autonomous replicating plasmid with an origin of replication).

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. The coding region usually codes for a functional RNA of interest, for example an RNAi molecule. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence. It may constitute an "uninterrupted coding sequence", i.e., lacking an intron, such as in a cDNA, or it may include one or more introns bounded by appropriate splice junctions. An "intron" is a sequence of RNA that is contained in the primary transcript but is removed through cleavage and re-ligation of the RNA within the cell to create the mature mRNA that can be translated into a protein.

The terms "initiation codon" and "termination codon" refer to a unit of three adjacent nucleotides (a 'codon') in a coding sequence that specifies initiation and chain termination, respectively, of protein synthesis (mRNA translation).

"Functional RNA" refers to sense RNA, antisense RNA, ribozyme RNA, siRNA, or other RNA that may not be translated but yet has an effect on at least one cellular process.

The term "RNA transcript" or "transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" are nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, regulatable promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency.

"3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

"Promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Examples of promoters that may be used in the present invention include the mouse U6 RNA promoters, synthetic human H1RNA promoters, SV40, CMV, RSV, RNA polymerase II and RNA polymerase III promoters.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. For example, in the case of siRNA constructs, expression may refer to the transcription of the siRNA only. In addition, expression refers to the transcription and stable accumulation of sense (mRNA) or functional RNA. Expression may also refer to the production of protein.

"Altered levels" refers to the level of expression in transgenic cells or organisms that differs from that of normal or untransformed cells or organisms.

"Overexpression" refers to the level of expression in transgenic cells or organisms that exceeds levels of expression in normal or untransformed cells or organisms.

"Antisense inhibition" refers to the production of antisense RNA transcripts capable of suppressing the expression of protein from an endogenous gene or a transgene.

"Transcription stop fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule. An example of a cis-acting sequence on the replicon is the viral replication origin.

The terms "trans-acting sequence" and "trans-acting element" refer to DNA or RNA sequences whose function does not require them to be on the same molecule.

"Chromosomally-integrated" refers to the integration of a foreign gene or nucleic acid construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The term "transformation" refers to the transfer of a nucleic acid fragment into the genome of a host cell, resulting in genetically stable inheritance. A "host cell" is a cell that has been transformed, or is capable of transformation, by an exogenous nucleic acid molecule. Host cells containing the transformed nucleic acid fragments are referred to as "transgenic" cells.

"Transformed," "transduced," "transgenic" and "recombinant" refer to a host cell into which a heterologous nucleic acid molecule has been introduced. As used herein the term "transfection" refers to the delivery of DNA into eukaryotic (e.g., mammalian) cells. The term "transformation" is used herein to refer to delivery of DNA into prokaryotic (e.g., E. coli) cells. The term "transduction" is used herein to refer to infecting cells with viral particles. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

As used herein, the term "derived" or "directed to" with respect to a nucleotide molecule means that the molecule has complementary sequence identity to a particular molecule of interest.

"Treating" as used herein refers to ameliorating at least one symptom of, curing and/or preventing the development of a disease or a condition.

Expression Cassettes of the Invention

To prepare expression cassettes, the recombinant DNA sequence or segment may be circular or linear, double-stranded or single-stranded.

Generally, the DNA sequence or segment is in the form of chimeric DNA, such as plasmid DNA or a vector that can also contain coding regions flanked by control sequences that promote the expression of the recombinant DNA present in the resultant transformed cell.

Aside from recombinant DNA sequences that serve as transcription units for an RNA transcript, or portions thereof, a portion of the recombinant DNA may be untranscribed, serving a regulatory or a structural function. For example, the recombinant DNA may have a promoter that is active in mammalian cells.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the siRNA, or the like. Such elements may be included in the DNA as desired to obtain the optimal performance of the siRNA in the cell.

Control sequences are DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

Operably linked nucleic acids are nucleic acids placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked DNA sequences are DNA sequences that are linked are contiguous. However, enhancers do not have to be contiguous. Linking is accomplished by ligation at convenient restriction sites. If such sites do not exist, the synthetic oligonucleotide adaptors or linkers are used in accord with conventional practice.

The recombinant DNA to be introduced into the cells may contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. For example, reporter genes include the chloramphenicol acetyl transferase gene (cat) from Tn9 of *E. coli* and the luciferase gene from firefly *Photinus pyralis*. Expression of the reporter gene is assayed at a suitable time after the DNA has been introduced into the recipient cells.

The general methods for constructing recombinant DNA that can transfect target cells are well known to those skilled in the art, and the same compositions and methods of construction may be utilized to produce the DNA useful herein.

The recombinant DNA can be readily introduced into the host cells, e.g., mammalian, bacterial, yeast or insect cells by transfection with an expression vector composed of DNA encoding the siRNA by any procedure useful for the introduction into a particular cell, e.g., physical or biological methods, to yield a cell having the recombinant DNA stably integrated into its genome or existing as a episomal element, so that the DNA molecules, or sequences of the present invention are expressed by the host cell. Preferably, the DNA is introduced into host cells via a vector. The host cell is preferably of eukaryotic origin, e.g., plant, mammalian, insect, yeast or fungal sources, but host cells of non-eukaryotic origin may also be employed.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. For mammalian gene therapy, as described herein below, it is desirable to use an efficient means of inserting a copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like.

As discussed above, a "transfected" or "transduced" host cell or cell line is one in which the genome has been altered or augmented by the presence of at least one heterologous or recombinant nucleic acid sequence. The host cells of the present invention are typically produced by transfection with a DNA sequence in a plasmid expression vector, a viral expression vector, or as an isolated linear DNA sequence. The transfected DNA can become a chromosomally integrated recombinant DNA sequence, which is composed of sequence encoding the siRNA.

To confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the preselected DNA segment is being expressed. Expression may be evaluated by specifically identifying the peptide products of the introduced recombinant DNA sequences or evaluating the phenotypic changes brought about by the expression of the introduced recombinant DNA segment in the host cell.

According to one embodiment, the cells are transfected or transduced or otherwise genetically modified in vivo. The cells from the mammalian recipient are transduced or transfected in vivo with a vector containing exogenous nucleic acid material for expressing a heterologous (e.g., recombinant) gene encoding a therapeutic agent and the therapeutic agent is delivered in situ.

Methods for Introducing the Expression Cassettes of the Invention into Cells

The condition amenable to gene inhibition therapy may be a prophylactic process, i.e., a process for preventing disease or an undesired medical condition. Thus, the instant invention embraces a system for delivering siRNA that has a prophylactic function (i.e., a prophylactic agent) to the mammalian recipient.

The inhibitory nucleic acid material (e.g., an expression cassette encoding siRNA directed to a gene of interest) can be introduced into the cell ex vivo or in vivo by genetic transfer methods, such as transfection or transduction, to provide a genetically modified cell. Various expression vectors (i.e., vehicles for facilitating delivery of exogenous nucleic acid into a target cell) are known to one of ordinary skill in the art.

As used herein, "transfection of cells" refers to the acquisition by a cell of new nucleic acid material by incorporation of added DNA. Thus, transfection refers to the insertion of nucleic acid into a cell using physical or chemical methods. Several transfection techniques are known to those of ordinary skill in the art including calcium phosphate DNA co-precipitation, DEAE-dextran, electroporation, cationic liposome-mediated transfection, tungsten particle-facilitated microparticle bombardment, and strontium phosphate DNA co-precipitation.

In contrast, "transduction of cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous nucleic acid material contained within the retrovirus is incorporated into the genome of the transduced cell. A cell that has been transduced with a chimeric DNA virus (e.g., an adenovirus carrying a cDNA encoding a therapeutic agent), will not have the exogenous nucleic acid material incorporated into its genome but will be capable of expressing the exogenous nucleic acid material that is retained extrachromosomally within the cell.

The exogenous nucleic acid material can include the nucleic acid encoding the siRNA together with a promoter to control transcription. The promoter characteristically has a specific nucleotide sequence necessary to initiate transcription. The exogenous nucleic acid material may further include additional sequences (i.e., enhancers) required to obtain the desired gene transcription activity. For the purpose of this discussion an "enhancer" is simply any non-translated DNA sequence that works with the coding sequence (in cis) to change the basal transcription level dictated by the promoter. The exogenous nucleic acid material may be introduced into the cell genome immediately downstream from the promoter so that the promoter and coding sequence are operatively linked so as to permit transcription of the coding sequence. An expression vector can include an exogenous promoter element to control transcription of the inserted exogenous gene. Such exogenous promoters include both constitutive and regulatable promoters.

Naturally-occurring constitutive promoters control the expression of essential cell functions. As a result, a nucleic acid sequence under the control of a constitutive promoter is expressed under all conditions of cell growth. Constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the beta-actin promoter, and other constitutive promoters known to those of skill in the art. In addition, many viral promoters function constitutively in eukaryotic cells. These include: the early and late promoters of SV40; the long terminal repeats (LTRs) of Moloney Leukemia Virus and other retroviruses; and the thymidine kinase promoter of Herpes Simplex Virus, among many others.

Nucleic acid sequences that are under the control of regulatable promoters are expressed only or to a greater or lesser degree in the presence of an inducing or repressing agent, (e.g., transcription under control of the metallothionein promoter is greatly increased in presence of certain metal ions). Regulatable promoters include responsive elements (REs) that stimulate transcription when their inducing factors are bound. For example, there are REs for serum factors, steroid hormones, retinoic acid, cyclic AMP, and tetracycline and doxycycline. Promoters containing a particular RE can be chosen in order to obtain an regulatable response and in some cases, the RE itself may be attached to a different promoter, thereby conferring regulatability to the encoded nucleic acid sequence. Thus, by selecting the appropriate promoter (constitutive versus regulatable; strong versus weak), it is possible to control both the existence and level of expression of a nucleic acid sequence in the genetically modified cell. If the nucleic acid sequence is under the control of an regulatable promoter, delivery of the therapeutic agent in situ is triggered by exposing the genetically modified cell in situ to conditions for permitting transcription of the nucleic acid sequence, e.g., by intraperitoneal injection of specific inducers of the regulatable promoters which control transcription of the agent. For example, in situ expression of a nucleic acid sequence under the control of the metallothionein promoter in genetically modified cells is enhanced by contacting the genetically modified cells with a solution containing the appropriate (i.e., inducing) metal ions in situ.

Accordingly, the amount of siRNA generated in situ is regulated by controlling such factors as the nature of the promoter used to direct transcription of the nucleic acid sequence, (i.e., whether the promoter is constitutive or regulatable, strong or weak) and the number of copies of the exogenous nucleic acid sequence encoding a siRNA sequence that are in the cell.

In one embodiment of the present invention, an expression cassette may contain a pol II promoter that is operably linked to a nucleic acid sequence encoding a siRNA. Thus, the pol II promoter, i.e., a RNA polymerase II dependent promoter, initiates the transcription of the siRNA. In another embodiment, the pol II promoter is regulatable.

A pol II promoter may be used in its entirety, or a portion or fragment of the promoter sequence may be used in which the portion maintains the promoter activity. As discussed herein, pol II promoters are known to a skilled person in the art and include the promoter of any protein-encoding gene, e.g., an endogenously regulated gene or a constitutively expressed gene. For example, the promoters of genes regulated by cellular physiological events, e.g., heat shock, oxygen levels and/or carbon monoxide levels, e.g., in hypoxia, may be used in the expression cassettes of the invention. In addition, the promoter of any gene regulated by the presence of a pharmacological agent, e.g., tetracycline and derivatives thereof, as well as heavy metal ions and hormones may be employed in the expression cassettes of the invention. In an embodiment of the invention, the pol II promoter can be the CMV promoter or the RSV promoter. In another embodiment, the pol II promoter is the CMV promoter.

As discussed above, a pol II promoter of the invention may be one naturally associated with an endogenously regulated gene or sequence, as may be obtained by isolating the 5' non-coding sequences located upstream of the coding segment and/or exon. The pol II promoter of the expression cassette can be, for example, the same pol II promoter driving expression of the targeted gene of interest. Alternatively, the nucleic acid sequence encoding the RNAi molecule may be placed under the control of a recombinant or heterologous pol II promoter, which refers to a promoter that is not normally associated with the targeted gene's natural environment. Such promoters include promoters isolated from any eukaryotic cell, and promoters not "naturally occurring," i.e., containing different elements of different transcriptional regulatory regions, and/or mutations that alter expression. In addition to producing nucleic acid sequences of promoters synthetically, sequences may be produced using recombinant cloning and/or nucleic acid amplification technology, including PCR, in connection with the compositions disclosed herein.

In one embodiment, a pol II promoter that effectively directs the expression of the siRNA in the cell type, organelle, and organism chosen for expression will be employed. Those of ordinary skill in the art of molecular biology generally know the use of promoters for protein expression. The promoters employed may be constitutive, tissue-specific, inducible, and/or useful under the appropriate conditions to direct high level expression of the introduced DNA segment, such as is advantageous in the large-scale production of recombinant proteins and/or peptides. The identity of tissue-specific promoters, as well as assays to characterize their activity, is well known to those of ordinary skill in the art.

In addition to at least one promoter and at least one heterologous nucleic acid sequence encoding the siRNA, the expression vector may include a selection gene, for example, a neomycin resistance gene, for facilitating selection of cells that have been transfected or transduced with the expression vector.

Cells can also be transfected with two or more expression vectors, at least one vector containing the nucleic acid sequence(s) encoding the siRNA(s), the other vector containing a selection gene. The selection of a suitable promoter, enhancer, selection gene and/or signal sequence is deemed to be within the scope of one of ordinary skill in the art without undue experimentation.

The following discussion is directed to various utilities of the instant invention. For example, the instant invention has utility as an expression system suitable for silencing the expression of gene(s) of interest.

The instant invention also provides methods for genetically modifying cells of a mammalian recipient in vivo. According to one embodiment, the method comprises introducing an expression vector for expressing a siRNA sequence in cells of the mammalian recipient in situ by, for example, injecting the vector into the recipient.

Thus, as will be apparent to one of ordinary skill in the art, a variety of suitable viral expression vectors are available for transferring exogenous nucleic acid material into cells. The selection of an appropriate expression vector to express a therapeutic agent for a particular condition amenable to gene silencing therapy and the optimization of the conditions for insertion of the selected expression vector into the cell, are within the scope of one of ordinary skill in the art without the need for undue experimentation.

In another embodiment, the expression vector is in the form of a plasmid, which is transferred into the target cells by one of a variety of methods: physical (e.g., microinjection, electroporation, scrape loading, microparticle bombardment) or by cellular uptake as a chemical complex (e.g., calcium or strontium co-precipitation, complexation with lipid, complexation with ligand). Several commercial products are available for cationic liposome complexation including Lipofectin™ (Gibco-BRL, Gaithersburg, Md.) and Transfectam™ (ProMega, Madison, Wis.). However, the efficiency of transfection by these methods is highly dependent on the nature of the target cell and accordingly, the conditions for optimal transfection of nucleic acids into cells using the above-mentioned procedures must be optimized. Such optimization is within the scope of one of ordinary skill in the art without the need for undue experimentation.

Diseases and Conditions Amendable to the Methods of the Invention

In the certain embodiments of the present invention, a mammalian recipient to an expression cassette of the invention has a condition that is amenable to gene silencing therapy. As used herein, "gene silencing therapy" refers to administration to the recipient exogenous nucleic acid material encoding a therapeutic siRNA and subsequent expression of the administered nucleic acid material in situ. Thus, the phrase "condition amenable to siRNA therapy" embraces conditions such as genetic diseases (i.e., a disease condition that is attributable to one or more gene defects), acquired pathologies (i.e., a pathological condition that is not attributable to an inborn defect), cancers, neurodegenerative diseases, e.g., trinucleotide repeat disorders, and prophylactic processes (i.e., prevention of a disease or of an undesired medical condition). A gene "associated with a condition" is a gene that is either the cause, or is part of the cause, of the condition to be treated. Examples of such genes include genes associated with a neurodegenerative disease (e.g., a trinucleotide-repeat disease such as a disease associated with polyglutamine repeats, Huntington's disease, and several spinocerebellar ataxias), and genes encoding ligands for chemokines involved in the migration of a cancer cells, or chemokine receptor. Also siRNA expressed from viral vectors may be used for in vivo antiviral therapy using the vector systems described.

Accordingly, as used herein, the term "therapeutic siRNA" refers to any siRNA that has a beneficial effect on the recipient. Thus, "therapeutic siRNA" embraces both therapeutic and prophylactic siRNA.

Differences between alleles that are amenable to targeting by siRNA include disease-causing mutations as well as polymorphisms that are not themselves mutations, but may be linked to a mutation or associated with a predisposition to a disease state.

A condition amenable to gene silencing therapy can be a genetic disorder or an acquired pathology that is manifested by abnormal cell proliferation, e.g., cancer. According to this embodiment, the instant invention is useful for silencing a gene involved in neoplastic activity. The present invention can also be used to inhibit overexpression of one or several genes. The present invention can be used to treat neuroblastoma, medulloblastoma, or glioblastoma.

Dosages, Formulations and Routes of Administration of the Agents of the Invention The agents of the invention are preferably administered so as to result in a reduction in at least one symptom associated with a disease. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems, which are well known to the art.

Administration of the aptamer chimera may be accomplished through the administration of the nucleic acid molecule. Pharmaceutical formulations, dosages and routes of administration for nucleic acids are generally known in the art.

The present invention envisions treating a disease, for example, cancer, in a mammal by the administration of an agent, e.g., a nucleic acid composition, an expression vector, or a viral particle of the invention. Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms having the therapeutic agent(s) of the invention, which, as discussed below, may optionally be formulated for sustained release (for example using microencapsulation), can be administered by a variety of routes including parenteral, including by intravenous and intramuscular routes, as well as by direct injection into the diseased tissue. For example, the therapeutic agent may be directly injected into the cancer. In another example, the therapeutic agent may be introduced intramuscularly for viruses that traffic back to affected neurons from muscle, such as AAV, lentivirus and adenovirus. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules, as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0, saline solutions, and water.

EXAMPLE 1

Optimization and Systemic Administration of Aptamer-siRNA Chimeras Targeting PSMA-Expressing Prostate Cancers Advanced prostate cancer (PC) is a multifactor disease with minimal options for treatment. Current therapies rely on non-specific treatments (e.g., chemotherapies and ionizing radiation), which result in low efficacy and high toxicity to normal tissues. Gene-specific mRNA "knockdown" with synthetic small interfering RNAs (siRNAs) is a potential therapeutic modality for advanced prostate cancer with a number of advantages over alternatives including target specificity, ease of production and the fact that siRNAs can be designed to silence virtually any gene in the human genome. In addition, recent advancements in understanding of the molecular mechanisms of RNA interference (RNAi) enable the rational optimization of the potency, specificity and in vivo activity of siRNAs. However, despite this important progress, delivery of siRNAs to the appropriate target cells in vivo remains a major hurdle for their broad clinical application.

Most siRNA-targeted approaches described to date involve complexation of siRNAs with charged peptides (Kumar et al., *Nature* 448(7149):39-43 (2007), Aigner A., *J Biotechnol.* 124(1):12-25 (2006); Meade et al., *Adv Drug Deliv Rev.* 59(2-3):134-40 (2007)), proteins (e.g., antibodies) (Song et al., *Nat Biotechnol.* 23(6):709-17 (2005); Peer et al., *Proc Natl Acad Sci USA.* 104(10):4095-100 (2007)), or polymers (Rozema et al., *Proc Natl Acad Sci USA.* 104(32):12982-7 (2007); Hu-Lieskovan et al., *Cancer Res.* 65(19):8984-92 (2005); Heidel et al., *Proc Natl Acad Sci USA.* 104(14):5715-21 (2007); Takei et al., *Cancer Res.* 64(10):3365-70 (2004); Takeshita et al., *Cancer Sci.* 97(8):689-96 (2006); Howard et al., *Mol Ther.* 14(4):476-84 (2006); Pillé et al., *Hum Gene Ther.* 17(10): 1019-26 (2006)). While these siRNA-based reagents are proving effective at silencing the targeted genes when administered systemically in experimental animals, their complex formulation complicates large-scale production and regulatory approval. An additional challenge in many cases is that the materials making up the complexes either exhibit toxicity in vivo or have uncertain safety profiles. As a result of these challenges, applications involving the direct local delivery (e.g., eye and lung) of naked or nuclease-resistant (e.g., 2' fluoro modified) siRNA duplexes (Chiu et al., *RNA* 9(9): 1034-48 (2003); Layzer et al., *RNA* 10(5):766-71(2004)) have been the first to be evaluated in clinical trials.

The inventors previously developed a simple RNA-only approach for delivering cytotoxic siRNAs targeting prostate cancer-specific pro-survival genes (Plk1 and Bcl2) directly to prostate cancer cells via an RNA aptamer (McNamara et al., *Nat Biotechnol.* 24(8):1005-15 (2006)). The aptamer portion of these reagents binds the prostate-specific membrane antigen (PSMA) (McNamara et al., *Nat Biotechnol.* 24(8):1005-15 (2006); Lupold et al., *Cancer Res.* 62(14):4029-33 (2002)), undergoes cell internalization, and delivers its siRNA cargo to the intracellular RNAi machinery. This action results in silencing of the siRNA target gene and pronounced cancer cell death in vitro. When injected intratumorally, the PSMA-targeting chimera significantly decreased tumor volume in a xenograph mouse model of prostate cancer (Mc-Namara et al., *Nat Biotechnol.* 24(8):1005-15 (2006)). It is important to note that this reagent only induced apoptosis in tumors expressing PSMA, while having no adverse effect on PSMA negative tumors or normal cells. Of note, the aptamer-conjugate approach can in principle be used to target any tissue or cell-type as long as a tissue-specific receptor (capable of cell internalization) is known and an aptamer to this receptor can be developed. Additional variables that will determine the success of this approach in different settings are the rate of receptor internalization and the ability of the aptamer to reach the cytoplasm upon internalization.

Although the PSMA aptamer/Plk1-siRNA chimera inhibited tumor growth when administered intratumorally (Mc-Namara et al., *Nat Biotechnol.* 24(8):1005-15 (2006)), systemic administration will be necessary for treatment of advanced prostate cancer, thus presenting a variety of additional challenges for the development of this approach. In particular, systemic administration requires greater therapeutic doses (thereby increasing the cost of treatment), and carries a greater risk for harmful side effects due to greater therapeutic exposure of non-targeted tissues. Improvements that would minimize the necessary dose of the chimera would reduce both the cost of treatment as well as the risk for harmful side effects. Towards this end, the inventors have modified several aspects of the first-generation PSMA-Plk1 chimera. The inventors enhanced the activity and target-specificity of the siRNA portion of the chimera. The inventors also extended the chimera's circulating half-life in vivo, through addition of a 20 kDa poly-ethylene glycol (PEG) moiety, without loss of function.

In addition, to enable mass-production through chemical synthesis, the inventors have truncated the RNA chimera from 96 nucleotides (nt) to 64 nt while retaining its activity. It is important to note that the inventors now show that when delivered systemically (via intra-peritoneal injections, i.p.) to mice bearing PSMA-positive prostate cancer tumors, the "optimized" chimera leads to silencing of the siRNA target gene in vivo and substantial regression of tumor growth. When compared to the first generation chimera, this "optimized" chimeric RNA leads to reduced tumor burden in mice at much lower doses.

In summary, the inventors describe substantial improvements in the in vivo efficacy of the first generation PSMA-Plk1 chimera. Because therapeutics consisting of the same materials used in this chimera (2'-fluoro-modified and PEG-conjugated RNA) have been extensively tested in humans and approved for therapeutic use, this reagent will be well-tolerated in human patients. This is the first description of a targeted one-component siRNA-based therapeutic approach with potential applicability to many diseases that may benefit from targeted gene-specific silencing.

Results

Second Generation "Optimized" PSMA-Plk1 Chimeras

Figure 1A:
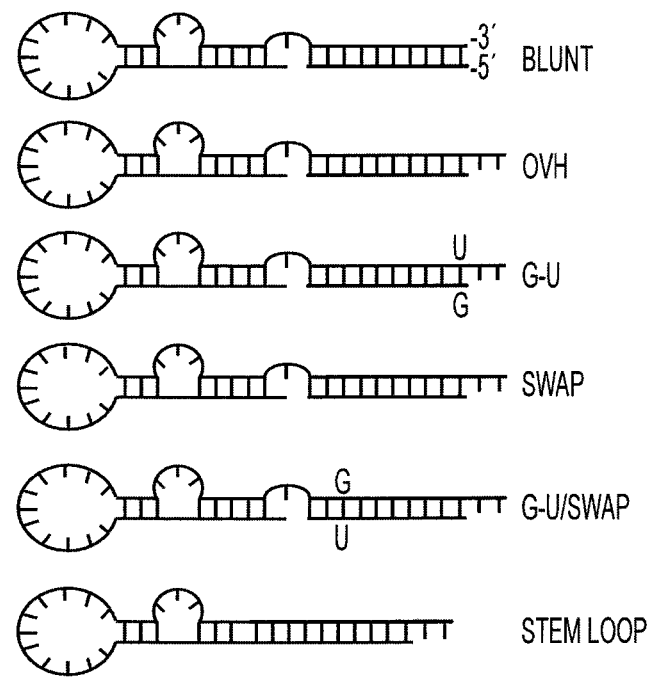
FIGS. 1A-1B. Schematic of Optimized PSMA-Plk1 Chimeras. The first-generation chimera (A10-Plk1) was previously described in McNamara et al., Nat Biotechnol. 24(8): 1005-15 (2006). "BLUNT" is the new truncated version of A10-Plk1. The aptamer portion of the chimera has been truncated from 71nt down to 39nt. OVH: overhang chimera is similar to BLUNT chimera with 2nt (UU)-overhangs at the 3' end of the siRNA duplex; G-U: G-U wobble chimera is identical to the OVH chimera but contains a wobble base pair at the 5' end of the antisense siRNA strand (silencing/guide strand); SWAP: sense and anti-sense strands of siRNA duplex are reversed; G-U/SWAP: the G-U base was introduced in the context of the SWAP chimera; Stem Loop:, hairpin chimera where the siRNA duplex (stem) is continuous with the aptamer (loop).
Figure 1B:
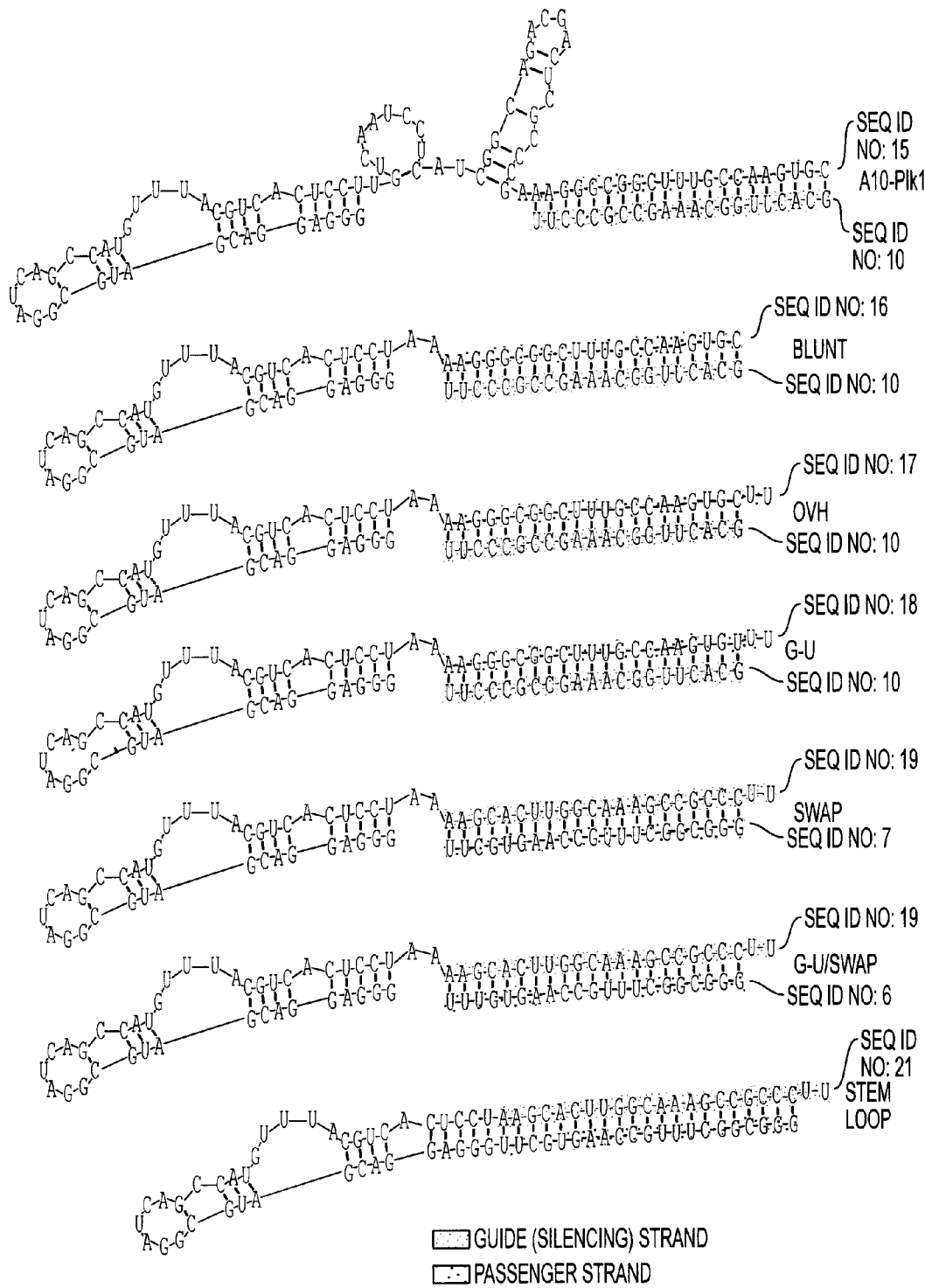

Schematics of the 'second-generation' PSMA-Plk1 chimeras are shown in FIGS. 1A and 1B. Second generation PSMA-Plk1 chimeras were designed to 1) facilitate chemical synthesis, 2) enhance silencing activity and specificity, and 3) enable modifications to optimize in vivo kinetics. To facilitate chemical synthesis, the aptamer portion of the chimera, which mediates binding to PSMA, was reduced to 39 nucleotides (nt) (A10-3.2). All second-generation chimeras were designed in the context of the truncated aptamer, where the longer RNA strand is modified with 2' fluoro pyrimidines and the shorter RNA strand is unmodified. An exception is the Stem Loop chimera which is fully modified. The first-generation chimera (A10-Plk1) was previously described in McNamara et al., 2006 (FIG. 1B). The truncated version of the A10-Plk1 is referred to as the BLUNT chimera (FIG. 1B). In this chimera, the Plk1 siRNA is a blunt duplex. In an attempt to increase the silencing activity and specificity of the PSMA-Plk1 chimera, chimeras were engineered with various modifications in the siRNA portion.

A chimera with 2nt (UU)-overhangs at the 3' end of the siRNA duplex (OVH chimera) was designed to favor recognition by the RNAse enzyme Dicer. A wobble base pair was engineered by introducing a mutation (C→U) in the sense strand (G-U wobble chimera). This was done in an attempt to increase silencing specificity by favoring loading of the guide strand into the RNA induced silencing complex (RISC) (Schwarz et al., *Cell* 115(2):199-208 (2003); Khvorova et al., *Cell* 115(2):209-16 (2003); Keck et al., *Mol. Ther.* 2008 (e-published ahead of print)). It has been reported that chemical modifications of the 5' terminus of the siRNA guide strand can result in loss of silencing (Czauderna et al., *Nucleic Acids Res.* 31(11):2705-16 (2003)). As a way to accommodate terminal modifications, without disrupting the silencing activity of the chimera, the sense (passenger) and anti-sense (guide/silencing) strands of siRNA duplex (SWAP chimera) were swapped. Swapping of the sense and antisense strands in the design of the SWAP chimera also takes advantage of strand loading bias introduced by the interaction of the 3' overhang with the PAZ domains of Ago2 and/or Dicer. This design favors loading of the guide strand (in this case top strand containing 3' overhangs) into RISC (Rose et al., *Nuc. Acids Res* 33:4140-4156 (2005); Sano et al., *Nuc. Acids Res.* 36:5812-5821 (2008)). The G-U/SWAP chimera is identical to the SWAP chimera with a wobble base pair at the 5' end of the guide strand. Finally, a Stem Loop hairpin chimera, where the siRNA duplex (stem) is continuous with the aptamer (loop), was designed to mimic endogenous microRNAs.

Binding of Optimized PSMA Chimeras to PSMA-Positive Cells

Figure 2A:
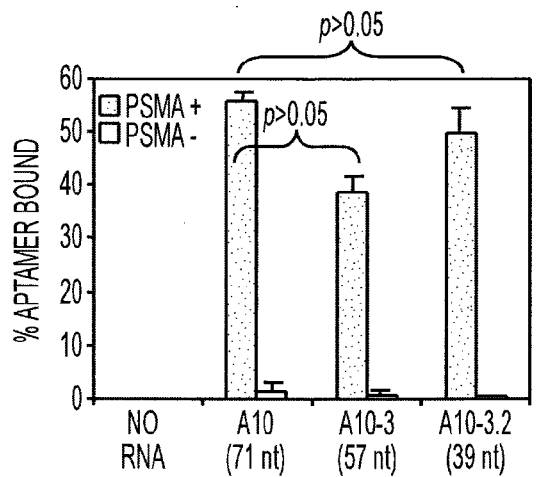
FIGS. 2A-2C. Binding of truncated versions of PSMA A10-Plk1 aptamer and optimized chimeras to cells expressing PSMA. RNAs were end labeled with $^{32}$P.
Figure 2B:
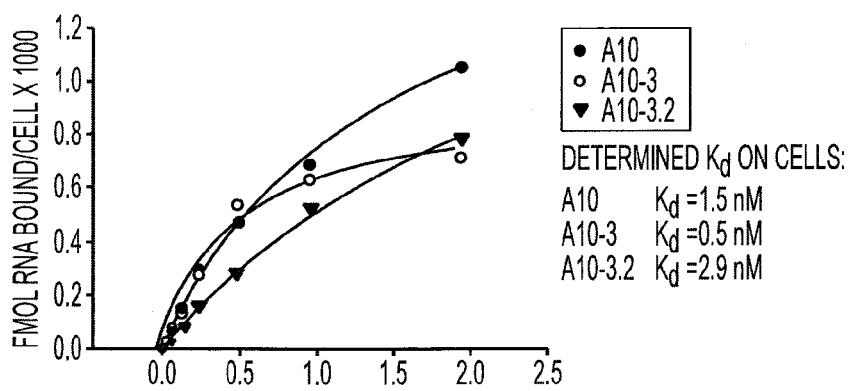

First, the ability of the truncated PSMA aptamer to bind the surface of prostate cancer cells expressing PSMA (LNCaP and 22Rv1 clone 1.7) was tested. A PSMA-negative prostate cancer cell line (PC-3) was used as a control for specificity. The surface expression of PSMA was verified using flow cytometry (data not shown). To determine whether the truncated PSMA aptamer can bind the surface of cells expressing PSMA, $^{32}$P-labeled A10-Plk1 (original PSMA aptamer; 71nt) (Lupold et al., *Cancer Res.* 62(14):4029-33 (2002)), A10-3 (57nt) (Lupold et al., *Cancer Res.* 62(14):4029-33 (2002)), and A10-3.2 (39nt) were incubated with either LNCaP or PC-3 cells (FIG. 2A). Binding of A10-Plk1, A10-3, and A10-3.2 was specific for cells expressing PSMA and was dependent on a region within A10-3.2 as this truncated RNA retained specific binding to PSMA-expressing cells. In addition, the truncated PSMA aptamer was found to bind to the surface of LNCaP cells with comparable affinity to the full-length A10-Plk1 RNA (FIG. 2B).

Figure 2C:
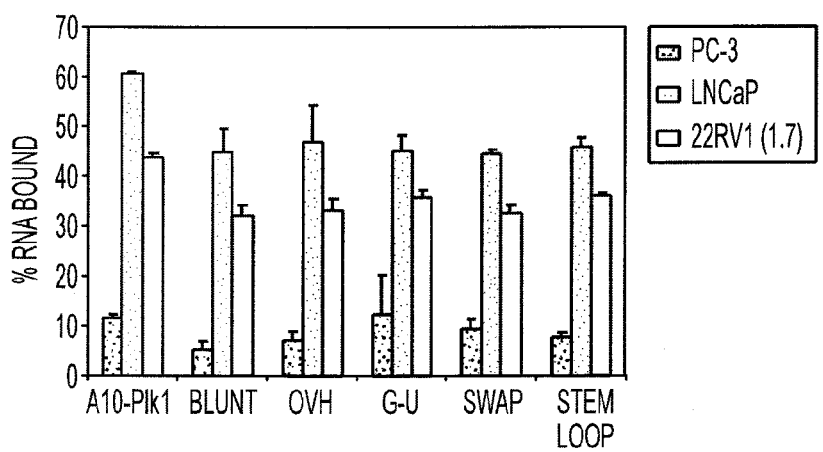

Next, the inventors tested the ability of A10-3.2, in the context of the second-generation chimeras, to bind to PSMA-expressing cells (FIG. 2C). $^{32}$P-labeled chimeras (A10-Plk1, BLUNT, OVH, G-U, SWAP, Stem Loop) were incubated with either PSMA-positive PC cells (LNCaP or 22Rv1 clone 1.7) or PSMA-negative PC cells (PC-3). All chimeras retained binding to PSMA-expressing PC cells. These experiments confirm that modifications made to the first generation chimera do not affect binding or target specificity.

Effect of Modifications on PSMA Chimera Silencing and RNAi Processing

Figure 3A:
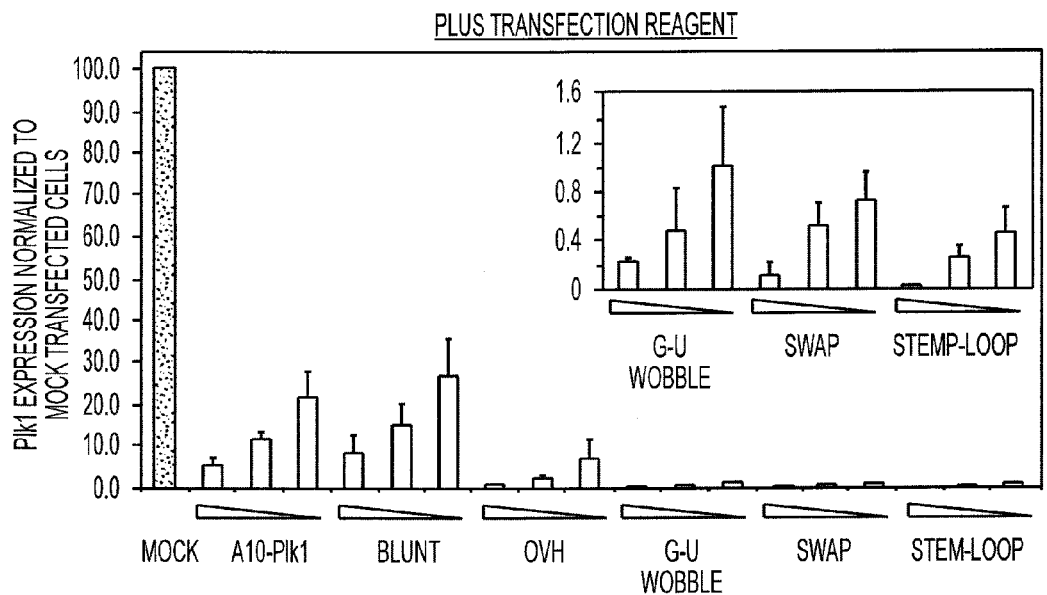
FIGS. 3A-3B. Silencing ability of PSMA chimeras. 22Rv1 (1.7) PSMA-positive prostate cancer cells were transfected with 400, 40, or 4nM of each chimera. Cells were processed for quantitative RT-PCR 24 h following transfection. % Plk1 expression was normalized to that of mock transfected (MOCK) cells.
Figure 3B:
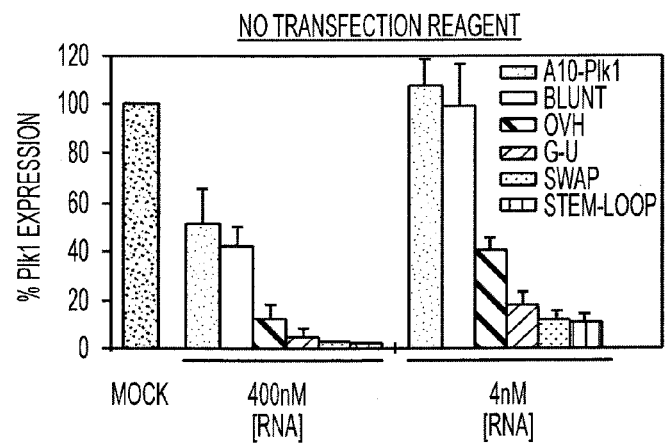

To determine whether the second-generation chimeras can silence target gene expression and whether the modified chimeras have enhanced silencing activity compared to the first-generation chimera, the inventors tested for gene-specific silencing using quantitative RT-PCR (qRT-PCR) (FIGS. 3A-3B). PSMA-expressing cells (22Rv1 clone 1.7) were transiently transfected with increasing amounts (4, 40, 400 nM) of A10-Plk1 or of the second-generation chimeras (BLUNT, OVH, G-U, SWAP, and Stem Loop) using a cationic lipid reagent (FIG. 3A). As a control for qRT-PCR, cells were transfected with a control non-silencing siRNA (Mock). Because it has not been previously reported that 22Rv1 prostate cancer cells overexpress Plk1, expression of the cancer cell-survival gene Plk1 in 22Rv1 PC cells was confirmed using immunoblotting (FIG. 7). The inventors also verified that elevated expression of Plk1 was specific to cancer cells as normal cells (human fibroblasts or normal prostate epithelial cells (data not shown)) have little-to-no Plk1 protein (FIG. 7). Expression of the cancer cell-survival gene Plk1 in 22Rv1 PC cells compared to normal cells (human fibroblasts or normal prostate epithelial cells) was confirmed using immunoblotting (FIG. 7). As expected, the modifications introduced within the siRNA portion of the chimera, enhanced chimera silencing (compare silencing activities of OVH, G-U, SWAP, and Stem Loop chimeras to BLUNT and A10-Plk1). The most active of the second-generation chimeras were the SWAP and the Stem Loop chimeras, which resulted in >99% silencing at concentrations as low as 4 nM.

Next, the ability of the second-generation chimeras to silence target gene expression in the absence of transfection reagent was verified (FIG. 3B). PSMA-expressing 22Rv1 (clone 1.7) PC cells were incubated with media containing either the first-generation chimera or the various second-generation chimeras. Silencing was confirmed by qRT-PCR 4 days following treatment. The modifications made to the siRNA portion of the chimeras substantially enhanced the chimeras' silencing potential (50% vs. >85% for A10-Plk1 and second-generation chimeras respectively) without affecting binding to PSMA on the surface of cells or internalization of the receptor/chimera complex. Importantly, no effect was observed on PSMA-negative PC cells (data not shown). These experiments indicate that the second-generation chimeras are as effective as the A10-Plk1 chimera at concentrations as low as 4 nM and have silencing activities 50-100 times greater than that of the first-generation chimera (A10-Plk1).

Figure 4A:
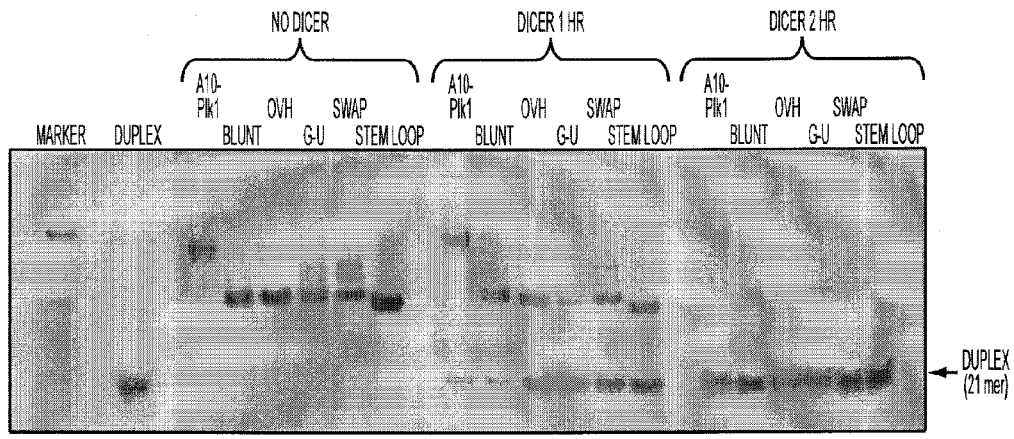
FIGS. 4A-4B. Analysis of Chimera Processing by the RNAi machinery.

Previously, the inventors showed that human Dicer can process the A10-Plk1 chimera. The inventors next assessed whether Dicer can process the siRNA portion of the chimeras in the context of the A10-3.2 PSMA aptamer (FIG. 4A). Either the sense or antisense strands of the Plk1 siRNA were end-labeled with γ-$^{32}$P-CTP and annealed to the corresponding aptamer strand to generate the duplex RNAs. For the Stem Loop chimera, the Stem Loop RNA was end-labeled with γ-$^{32}$P-CTP. The chimeras were incubated with recombinant human Dicer for 1 h and 2 h and the cleavage products were analyzed by non-denaturing gel electrophoresis. Incubation with Dicer resulted in $^{32}$P-labeled cleaved products corresponding to the size of the duplex Plk1 siRNA (21 mer). These data suggest that the RNA chimeras are Dicer substrates. Importantly, as previously reported by Zhou et al., the size of the $^{32}$P-labeled cleaved products (~21 mer) also indicates from which side Dicer enters the chimera and cleaves (Mol Therapy 16:1481-1489 (2008)). These results suggest that Dicer enters from the 3'-end of the chimera and cleaves ~21nt upstream.

Figure 4B:
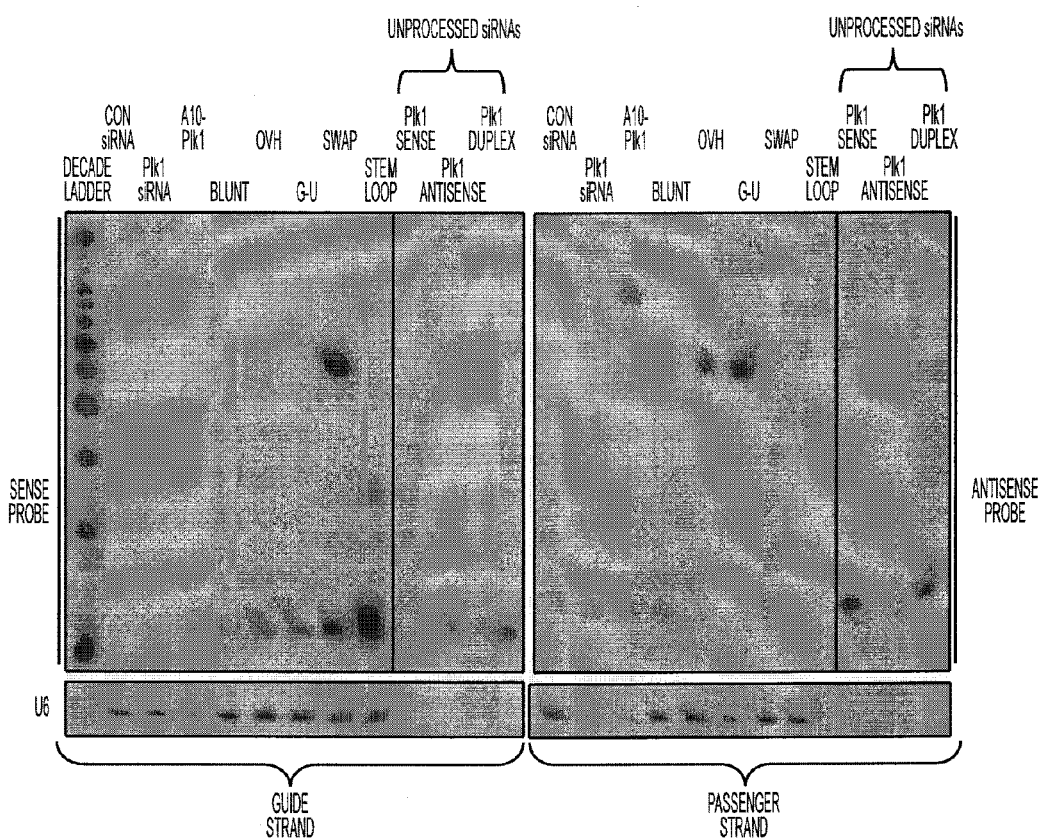

Next, the inventors tested whether modifications made to the siRNA portion of the second-generation chimeras affect loading of the correct siRNA-silencing strand into RISC (FIG. 4B). Indeed, loading of the correct strand into the RNAi machinery translates into siRNAs with increased activity and reduced off-target effects (Reynolds et al., Nat Biotechnol. 22(3):326-30 (2004)). Silencing activity and specificity was assessed by small fragment northern (or strand-bias assay) (Czauderna et al., Nucleic Acids Res. 31(11):2705-16 (2003)). This assay allows a quantitative measure of the 'guide' strand of the siRNA duplex that is preferably incorporated into RISC and therefore protected from nuclease degradation. The strand that is not incorporated into RISC is rapidly degraded. By this measure, modifications made to the first-generation chimera substantially enhanced loading of the correct strand into RISC. While the addition of 2nt (UU)-overhangs at the 3' end of the siRNA duplex alone enhanced loading of the correct strand into RISC (compare BLUNT to OVH chimera), incorporation of a wobble base at the 5' end of the guide strand, which optimizes the thermodynamic profile of the duplex, did not affect correct strand loading. It was important to note that swapping the sense strand with the anti-sense (silencing/guide) strand resulted in a substantial increase in loading of the guide strand into RISC (compare OVH to SWAP chimera) (FIG. 4B). An even greater effect on strand loading (~20-fold increase) was observed with the Stem Loop chimera, which has the same sense/anti-sense configuration of the SWAP chimera (FIG. 4B). Together, these data indicate that the modifications made to the siRNA portion of the PSMA-Plk1 chimeras enhance silencing activity and specificity by promoting optimal RNAi processing.

Effect of PSMA-Plk1 Chimeras on Prostate Cancer Cell Growth and Survival

Depletion of Plk1 in cancer cells leads to a G2/M arrest (mitotic block) resulting in a reduction in cell proliferation and subsequent cancer cell death due to a phenomenon known as mitotic crisis (Reagan-Shaw et al., FASEB J. 19(6):611-3 (2005)). To determine whether treatment with the various PSMA chimeras results in reduced cellular proliferation, 22Rv1 PSMA-positive PC cells were transiently transfected with 4 nM of each of the RNAs using a cationic lipid reagent and cell proliferation was measured by $^3$H-thymidine incorporation (FIG. 5A). Mock treated cells (treated with control non-silencing siRNA) were used to determine normal rate of cellular proliferation prior to treatment. Cisplatin (positive control) was used to inhibit cell proliferation and induce cell death. As previously observed, silencing of Plk1 by the A10-Plk1 chimera (at 400 nM concentration) resulted in substantial inhibition of cell proliferation (McNamara et al., Nat Biotechnol. 24(8):1005-15 (2006)). Lowering the concentration of A10-Plk1 to 4 nM drastically reduced the effect on cellular proliferation by ~6-fold. In contrast, when transfected into 22Rv1 cells, the second-generation chimeras were capable of robust inhibition of cellular proliferation (compare OVH, G-U, SWAP, SWAP/G-U, and Stem Loop to BLUNT or A10-Plk1) even at concentrations as low as 4 nM (FIG. 5A). This correlated with cells arresting in the G2/M phase of the cell cycle as measured by propidium iodide (PI) staining of DNA content by flow cytometry (FIG. 5B). Nocodazole, a microtubule-depolymerizing drug, was used as a positive control to arrest cells in G2/M.

Next, the inventors determined whether the second-generation chimeras could induce apoptosis of treated cells and whether modifications of the siRNA moiety increase their apoptotic activity. 22Rv1 (clone 1.7) cells were treated with 4 nM of the various chimeras in the absence of transfection reagent. Cisplatin was used as a control for apoptosis, which was assessed by measuring production of active caspase 3 (Casp3) by flow cytometry (FIGS. 5C and 5D). As expected, the modifications introduced within the Plk1 siRNA sequence (compare OVH, G-U, SWAP, and Stem Loop chimeras to BLUNT chimera) greatly enhanced cell death from 22% (for BLUNT) to 75-85% (for SWAP and Stem Loop chimeras). When used at a 100-fold lower concentration, the SWAP and Stem Loop chimeras were more effective than the first-generation (A10-Plk1) chimera or BLUNT chimera at inducing cell death (FIG. 5D). Together these data suggest that the modifications made to the second-generation chimeras greatly enhance silencing as well as Plk1-mediated mitotic crisis/apoptosis.

In vivo Efficacy of Optimized PSMA-Plk1 Chimeras

The inventors assessed the efficiency and specificity of the second-generation chimeras for their ability to limit tumor growth in athymic mice bearing tumors derived from either PSMA-positive (22Rv1 clone 1.7) or PSMA-negative (PC-3) PC cells (FIGS. 6A-6B). PSMA expression in tumors was confirmed by immunoblot analysis (FIG. 8). For the in vivo experiment the inventors focused on comparing the cytotoxic effects of the SWAP chimera to those of the BLUNT chimera. Athymic mice (>10 mice per treatment group) were subcutaneously injected in the flanks with either 22Rv1 clone 1.7 cells or PC-3 cells. Both cancer cell lines express luciferase, which allows measurement of tumor growth using bioluminescence imaging (BLI) (FIG. 6B). Tumors were allowed to grow until they reached ~0.75 cm in diameter in the longest dimension (on averaged tumor volumes were ~0.4 cm$^3$ at start of treatment). Intraperitoneal (i.p.) injections of either phosphate buffered saline (PBS) or 1 nmol each of the chimeric RNAs (BLUNT, SWAP, or a non-silencing chimera/A10-3.2-Con) were performed each day for a total of 10 days (starting on Day 0). Tumors were measured with calipers every other day for the course of the experiment. On day 10, animals were injected with luciferin and BLI was performed using the Xenogen system to obtain a more quantitative measurement of tumor volume and viability (FIG. 6B). Tumor volumes were calculated by placing a circular region of interest (ROI) around the tumor and quantified total flux using Living Image® Software v2.50 (Xenogen) with units of photons/sec/cm$^2$/sr (FIG. 8) (Drake et al., Clin Exp Metastasis 22(8):674-84 (2005)). No difference in tumor volume was observed with the PC-3 tumors with either the PBS or the SWAP chimera indicating that the SWAP chimera did not have any nonspecific cell killing effects. In contrast, a pronounced reduction in tumor volume was observed for PSMA-expressing 22Rv1 tumors treated with the SWAP chimera (compare SWAP to PBS, A10-3.2-Con, or BLUNT) (FIG. 6A). Indeed, from day 0 to day 10 the PBS and A10-3.2-Con treated tumors increase by ~4-fold in volume (n=34, n=14 tumors respectively), the BLUNT treated tumors increased by ~2-fold in volume (n=24 tumors), whereas the SWAP treated tumors had a 4-fold reduction in volume (n=48 tumors) (P<0.001). Notably, ~70% of all SWAP treated tumors (corresponding to smaller tumors at start of injection) completely regressed by the end of the treatment. Of the remaining, ~30% (see insert indicated by arrow for BLI of representative tumor-bearing mice), the growth rate of all tumors was significantly slowed (by as much as 2.3-folds) with the exception of one mouse whose tumor rate increased by 1.4-folds from day 0 to day 10 (FIG. 6A). Although regression of PSMA-positive tumors was most evident in SWAP treated mice, tumor growth was significantly slowed in mice treated with the BLUNT chimera (compare PBS with BLUNT) (P<0.001). Notably, no morbidity or mortality was observed following the 10 day treatment with the chimeric RNAs, suggesting that these compounds are not toxic to the animal under the conditions of the experiment. This was performed by gross inspection or histological analysis described below.

Tumors from SWAP (but not PBS) treated mice had liquefactive material that would exude from the tumor mass during gross sectioning. Histologically, this was determined to be consistent with large coalescing lakes of caseous necrosis commonly detected the SWAP mice, but significantly less so in the PBS treated mice (FIG. 6C). Mitotic figures were detected in all groups including some occasional large bizarre mitoses in SWAP treated mice. TUNEL staining was seen throughout the tissues as brown staining of random individual cells and along the interface of necrotic and viable tumor tissue. Notably, no substantial change in tumor histology was noted for PSMA-negative PC-3 tumors treated with the SWAP chimera vs. the PBS control suggesting that no non-specific uptake and subsequent processing of this chimera is occurring following systemic administration. In addition, cellular inflammation was uncommon and mild, detected often along the peripheral border of the tumor and composed of scattered neutrophils with lesser mononuclear cells. Importantly, within each tumor type (22Rv1 or PC-3) there were no detectable differences in cellular inflammation quality, distribution, or severity between treatments (e.g., PBS vs. SWAP). This suggests that tumor regression is not likely to be dependent on an immune response. To confirm that this was indeed the case, serum from treated mice was screened for levels of interferon-α (INT-α) and interleukine-6 (IL-6) using an enzyme-linked immunosorbent assay (ELISA) (FIG. 6D). Importantly, no statistically significant difference was seen in cytokine levels of mice treated with either saline (PBS) or either the A10-3.2-Con or SWAP chimeras. This was in contrast to mice treated with polyinosinic:polycytidylic acid (poly I:C), a potent immune stimulator. These data suggest that the chimeras do not trigger an innate immune response and may be safe for in vivo applications.

To confirm that the siRNAs released from the chimeras were indeed triggering RNAi in vivo, the inventors performed a modified 5'RACE-PCR as previously described (McNamara et al., *Nat. Biotechnol.* 24:1005-1015 (2006)). The cleaved product of mRNA from tumors previously treated with the various PSMA-Plk1 chimeras was ligated to an RNA adaptor and reversed transcribed using a gene-specific primer (FIG. 6E). Gel electrophoresis and sequencing of the 5'RACE-PCR products using a primer specific to the RNA adaptor and a reverse primer specific to Plk1 show that Ago2-mediated cleavage occurs between bases 10 and 11 relative to the 5'-end of the guide Plk1 siRNA strand. This result confirms specific siRNA-mediated cleavage products of Plk1 mRNA in treated tumors in vivo.

It was determined whether the addition of a 20 kDa polyethylene glycol (PEG) group could extend the circulating half-life (FIG. 6F) of the SWAP chimera without affecting binding to PSMA (FIG. 9A) or Plk1 silencing activity (FIG. 13B). A 20 kDa PEG was placed at the 5'-end of the passenger strand of the Plk1 siRNA by chemical synthesis (TriLink, Inc.). In addition, during synthesis 2' fluoro-modified pyrimidines were incorporated into the siRNA strand (TriLink, Inc.). The resulting chimera is fully 2' fluoro-modified on the pyrimidines with a 20 kDa PEG at the 5'-terminus of the passenger strand (bottom strand) (SWAP-2'F-PEG). An analogous fully 2' fluoro-modified chimera (SWAP-2'F) with no terminal PEG was used as a control for these experiments (FIG. 9B). The 2' fluoro modified nucleotides are represented schematically with an asterisk (*) symbol. Initially, the inventors looked at the effect of the PEG modification on chimera binding and internalization into cells expressing PSMA (FIG. 9A). PSMA-positive (22Rv1) and PSMA-negative (PC-3) cells were incubated with fluorescently-labeled SWAP-2'F or SWAP-2'F-PEG. To assess surface binding, cells were washed several times with PBS to remove unbound RNA. To determine whether the PEG-modified chimera could internalize into cells upon binding, a high salt wash was performed to remove surface bound chimera. Notably, both the SWAP-2'F and SWAP-2'F-PEG chimeras were capable of binding to PSMA-expressing cells. No binding was observed with either chimera to PC-3 cells (FIG. 9A). While both chimeras were capable of internalizing in PSMA-positive cells, less internalization was observed with the PEG-modified chimera (69% vs. 45% internalization) suggesting that the PEG modification may be affecting the rate of internalization or promoting excretion once in the cell. While the addition of a terminal PEG seems to negatively affect chimera internalization/retention, no difference was observed in the silencing activities of these chimeras (FIG. 9B).

The in vivo half lives of the SWAP-2'F and SWAP-2'F-PEG chimeras were determined. The RNAs were i.p. injected into 3 mice per group. Blood samples were obtained 10 min, 1 h, 5 h, and 30 h following injection. qRT-PCR was used to quantitate the amount of RNA present in each blood sample. The in vivo circulating half-life of the SWAP-2'F chimera was substantially increased (from <35 min to >30 h) by the addition of the 20 kDa PEG (FIG. 6F, left panel). Next, whether the prolonged in vivo retention time of the SWAP chimera leads to increased in vivo efficacy was addressed. Mice bearing PSMA-positive (22Rv1) tumors, were i.p. injected with a low dose (250 pmols) of the SWAP-TF or SWAP-2'F-PEG chimeras or with PBS. A total of 5 injections were performed over the course of 10 days. Tumor volume was determined as in FIG. 6A above. As anticipated, prolonging the chimera's circulating half-life through a terminal PEG modification results in a reagent that leads to tumor regression at significantly lower doses (compare FIG. 6A to FIG. 6F right panel; 10×1 nmol vs. 5×250 pmols).

The inventors next verified whether tumor regression in treated mice was due to silencing of Plk1 gene expression by the PSMA-Plk1 chimeras (FIG. 6G, left panel). qRT-PCR was used to quantitate the amount of Plk1 mRNA present in treated tumors. A total of nine tumors per treatment group were processed for the experiment. Plk1 mRNA expression was significantly reduced in SWAP (P<0.01) and SWAP-2'F-PEG (P<0.05) treated tumors compared to PBS control or to a non-silencing PSMA chimera (A10-3.2-Con).

Finally, to verify whether prolonged silencing of Plk1 gene expression was responsible for the difference in the in vivo efficacies of the SWAP-2'F-PEG and SWAP-2'F chimeras as seen in FIG. 6F, the inventors carried out a more thorough PK/PD study to assess silencing over time (FIG. 6G; right panel). In this experiment PSMA-positive tumor bearing mice were injected with two consecutive doses (one day apart) of 1 nmol each of either the SWAP-2'F or SWAP-2'F-PEG chimeras. Tumors were collected 48 h and 5d after treatment administration. Quantitative RT-PCR was then performed on mRNA from tumors to determine the amount of Plk1 mRNA in the treated tumors at the given time points. As shown in FIG. 6G (right panel) Plk1 mRNA silencing is observed in both SWAP-2'F and SWAP-2'F-PEG treated tumors at 48 h but only in the SWAP-2'F-PEG treated tumors 5d following the last treatment. These data suggest that the increased stability of the SWAP-2'F chimera in serum is leading to extended silencing.

The PLK-1 siRNA was the only siRNA against Plk1 that was been shown to be effective as an siRNA prior to the present work. The present inventors surprisingly were able to improve upon that molecule by modifying the sequence in the context of the PSMA-Plk1 chimera by adding 2-nt 3' overhang and introducing a G-U wobble at the 3' end of the sense strand of the duplex siRNA.

```
Original Plk1 siRNA sense sequence used in
chimera:
5'GGGCGGCUUUGCCAAGUGCUU3'         (SEQ ID NO: 7)

Optimized Plk1 sense sequence in G-U wobble
chimera:
5'GGGCGGCUUUGCCAAGUGUUU3'         (SEQ ID NO: 6)
```

Discussion

In this study, the inventors describe a targeted one-component (RNA-only) approach for the treatment of prostate cancer that is effective in vivo when delivered systemically and is amenable to chemical synthesis for scale-up production. Specifically, the inventors have developed and characterized PSMA-Plk1 chimeras with enhanced activity, specificity and in vivo kinetics compared to the "first-generation" PSMA-Plk1 chimera (McNamara et al., *Nat Biotechnol.* 24(8):1005-15 (2006)). These "optimized" RNA-only chimeras retain their ability to target specific cell types (PSMA overexpressing prostate cancer cells), while acquiring enhanced silencing activity and specificity when delivered intracellularly.

Chimeras with increased potency and specificity were engineered. These include the addition of 2nt 3'-overhangs and optimization of the thermodynamic profile and structure of the duplex to favor RISC processing of the correct siRNA guide strand.

Figure 9B:
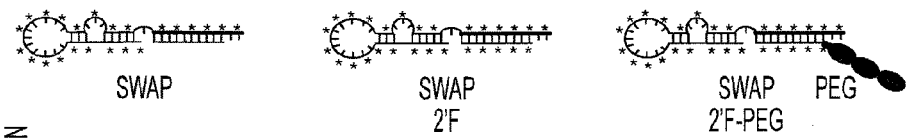
Figure 9B:
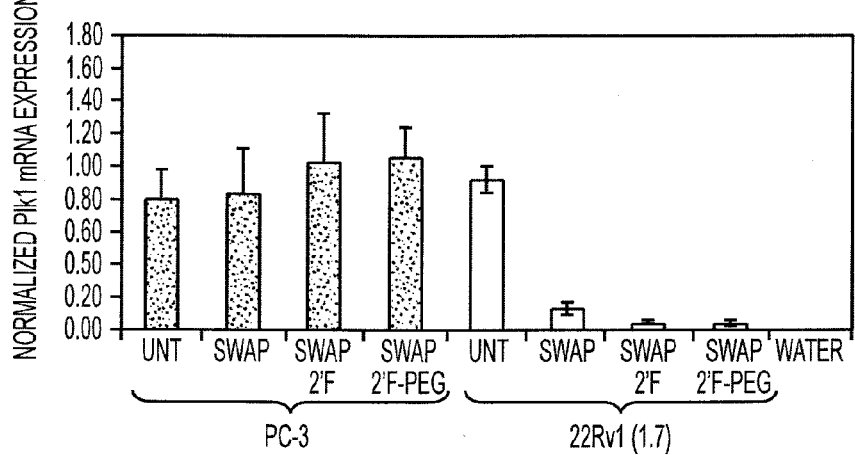

For many potential therapeutic applications of chimeras, including cancer therapy, it is necessary to administer the therapeutic reagent systemically. Thus, in addition to enhancing the potency and specificity of these chimeras, it is necessary to optimize their in vivo kinetics. Terminal modification of RNAs with PEG has been used to increase the half-life and bioavailability of many oligonucleotide-based therapies (including RNA aptamers) to allow clinical translation (Czauderna et al., *Nuc. Acids Res.* 31:2705-2716 (2003); Bozza et al., *Biochemistry* 45:7639-43 (2006); Veronese et al., *BioDrugs* 22:315-329 (2008)). The inventors found that addition of a 20 kDa PEG to the 5'-terminus of the smaller RNA strand, promotes increased retention of the chimera in serum without affecting chimera targeting and silencing (FIG. 9). It was surprising to note that the PEGylated reagent leads to prolonged-silencing in vivo (FIG. 6G, right panel) and to inhibition of tumor growth, at significantly lower doses, in mice bearing PSMA-positive prostate tumors (FIG. 6E, right panel). Consistent with results of previous studies that found PEG to be safe for in vivo applications (Veronese et al., *BioDrugs* 22:315-329 (2008)), no morbidity (following gross inspection of major organs) or mortality was observed in treated mice over the course of the experiment.

As previously described for the first-generation PSMA-Plk1 chimera, cellular targeting of the optimized chimeric RNAs was mediated by the interaction of the aptamer portion of the chimeras with PSMA expressed on the surface of prostate cancer cells (FIG. 2C). Importantly, it was found that the first 39nt of the A10-Plk1 PSMA aptamer are sufficient for targeting the chimeras to PSMA expressed on the surface of prostate cancer cells. This allowed for the truncation of the aptamer portion of the chimeras from 71nt down to 39nt in length without loss of function (FIGS. 2A-2C). Chimeras designed with such short aptamers (<39 bases) have a long strand of <64 bases, a length that can currently be produced with chemical synthesis for scale-up production.

Depletion of Plk1 by the "optimized" chimeras was also specific to PSMA-positive prostate cancer cells (data not shown) and resulted in decreased proliferation and increased apoptosis of the target cells in culture (FIGS. 5A, 5C and 5D). Notably, following modifications to the siRNA portion of the chimera, these effects were observed at concentrations of the reagent 50 to 100-fold lower than for the "first-generation" chimera (FIGS. 5A and 5D). In addition, the inventors now show that upon depletion of Plk1, the prostate cancer cells undergo a mitotic arrest (FIG. 5B) leading to cell death by apoptosis (as measured by induction of active cleaved caspase 3). Coincident with the present finding, depletion of Plk1 expression has been reported to lead to mitotic crisis (due to arrest of cancer cells at the G2/M transition of the cell cycle) and death of prostate cancer cells following Plk1 inhibition (Reagan-Shaw et al., *FASEB J.* 19(6):611-3 (2005)). This effect is specific to cancer cells while normal cells will resume entry in the cell cycle upon restoration of Plk1 expression (Reagan-Shaw et al., *FASEB J.* 19(6):611-3 (2005); Reagan-Shaw et al., *IUBMB Life* 57(10):677-82 (2005); Strebhardt et al., *Nat Rev Cancer.* 6(4):321-30 (2006)).

An additional measure of specificity was achieved by modifying the siRNA portion of the chimera to enhance loading of the guide (silencing) strand into RISC (FIG. 4B). Optimal loading of the guide strand into RISC is thought to reduce off-target effects that result from inappropriate incorporation of both siRNA strands into the silencing complex (Schwarz et al., *Cell* 115(2):199-208 (2003); Khvorova et al., *Cell* 115(2):209-16 (2003); Reynolds et al., *Nat Biotechnol.* 22(3):326-30 (2004)). Notably, loading of the guide strands of the second-generation chimeras was substantially increased over that of the first-generation reagent (FIG. 4B). While potential off-target effects mediated by the guide strand itself cannot be completely ruled out, it is likely that these effects would be largely restricted to the tumor since the siRNAs would be target predominantly to PSMA-expressing prostate cancer cells (FIG. 6A).

A major advantage of the PSMA-Plk1 chimera approach as a therapeutic for advanced prostate cancer lies in its target specificity, which is achieved at two levels: at the level of the aptamer (PSMA-expressing cells are predominantly targeted) and at the level of the siRNA (siRNAs are designed against cancer-specific transcripts). Cancer cell-specific targeting could substantially reduce the amount of siRNA needed for effective therapy while reducing organismal cytotoxicity. Most targeted delivery approaches for siRNAs described to date involve the use of complex formulations of synthetic polymers, proteins (antibodies, protamine), or charged peptides (RVG). While these approaches are proving effective in pre-clinical studies these multicomponent formulations may complicate production and safety assessment. Indeed, additional considerations that must be taken into account when selecting reagents for therapeutic development, beyond in vivo efficacy, involve safety and ease/cost of manufacturing.

The PSMA-Plk1 chimera is an all-RNA approach, where the RNA has been modified with 2' fluoro pyrimidines for increased in vivo stability and decreased non-specific immunostimulation, and a terminal 20 kDa PEG for increase serum retention. Both modifications have been fairly well characterized in humans and are reported to be well tolerated with little-to-no toxicity (Layzer et al., *RNA* 10(5):766-71(2004); Veronese et al., *BioDrugs*. 22(5):315-29 (2008)). Notably, RNA oligonucleotides (aptamers and siRNAs) with similar modifications have already been approved for use in humans, with many more quickly moving through the clinical pipeline (Dyke et al., *Circulation* 114(23):2490-7 (2006); Chan et al., *Circulation* 117(22):2865-74 (2008); Katz et al., *Int Ophthalmol Clin*. 46(4):141-54 (2006); Gilbert et al., *Circulation* 116(23):2678-86 (2007); Girvan et al., *Mol Cancer Ther*. 5(7):1790-9 (2006); Soundararajan et al., *Cancer Res*. 68(7): 2358-65 (2008)).

Furthermore, a simple one-component system, which involves the direct conjugation of the siRNA to the RNA aptamer, significantly reduces the complexity of the final drug product and greatly simplifies manufacturing. To date, the other siRNA-conjugate approaches that has demonstrated in vivo activity are lipophilic-based (Soutschek et al., *Nature* 432(7014):173-8 (2004)) and dynamic polyconjugate approaches that target the asialoglycoprotein receptor on hepatocytes. In the study by Soutschek and coworkers, a siRNA silencing ApoB was directly conjugated to cholesterol. Specific silencing of ApoB in the liver and jejunum of treated mice was achieved after intravenous administration of the cholesterol-siRNA conjugates. Cholesterol conjugation promotes binding to serum lipoparticles leading to improved pharmacokinetics of the siRNA and subsequent internalization by a hepatocyte-specific receptor (Wolfrum et al., *Nat Biotechnol*. 25(10):1149-57(2007)). While this remains a powerful approach for delivery to the liver or other lipophilic tissues (e.g., brain), it is likely to have limited applicability to most other cell types.

Materials and Methods

Unless otherwise noted, all chemicals were purchased from Sigma-Aldrich Co., all restriction enzymes were obtained from New England BioLabs, Inc. (NEB), and all cell culture products were purchased from GIBCO BRL/Life Technologies, a division of Invitrogen™ Corp. Antibodies were purchased from the following manufacturers: Plk1 (cat #33-1700; Zymed®/Invitrogen™, Carlsbad, Calif.); Erk1 K-23 (sc-94; Santa Cruz, Calif.); PSMA (cat#M20454M; Biodesign®, Saco, Me.); β-actin (cat#A5441; Sigma-Aldrich Inc.); HRP-labeled rabbit anti-mouse IgG secondary antibody (cat#61-6420 Zymed®/Invitrogen™, Carlsbad, Calif.).

```
siRNA sequences
con siRNA target sequence:
5'AATTCTCCGAACGTGTCACGT3'      (SEQ ID NO: 13)

Plk1 siRNA target sequence:
5'AAGGGCGGCTTTGCCAAGTGC3'      (SEQ ID NO: 14)
```

Aptamer-siRNA Chimera Sequences (FIG. 1B)

A10-Plk1 Chimera (in Italics are the 2' Fluoro Modified Nucleotides):

A10-Plk1 Sense Strand: (modified with 2' fluoro pyrimidines)

```
                                           (SEQ ID NO: 15)
5'GGGAGGACGAUGCGGAUCAGCCAUGUUUACGUCACUCCUUGUCAAUCC
UCAUCGGCAGACGACUCGCCCGAAAGGGCGGCUUUGCCAAGUGC3'
```

Plk1 Antisense siRNA: (unmodified RNA)

```
5'GCACUUGGCAAAGCCGCCCUU3'     (SEQ ID NO: 10)
```

BLUNT Chimera:
BLUNT RNA Sense Strand:

```
                                           (SEQ ID NO: 16)
5'GGGAGGACGAUGCGGAUCAGCCAUGUUUACGUCACUCCUAAAAGGGCG
GCUUUGCCAAGUGC3'
```

Plk1 Antisense siRNA: (unmodified RNA)

```
5'GCACUUGGCAAAGCCGCCCUU'     (SEQ ID NO: 10)
```

OVH Chimera:
OVH RNA Sense Strand: (modified with 2' fluoro pyrimidines)

```
                                           (SEQ ID NO: 17)
5'GGGAGGACGAUGCGGAUCAGCCAUGUUUACGUCACUCCUAAAAGGGCG
GCUUUGCCAAGUGCUU3'
```

Plk1 Antisense siRNA: (unmodified RNA)

```
5'GCACUUGGCAAAGCCGCCCUU3'     (SEQ ID NO: 10)
```

G-U Chimera:
G-U RNA Sense Strand: (modified with 2' fluoro pyrimidines indicated in italics)

```
                                           (SEQ ID NO: 18)
5'GGGAGGACGAUGCGGAUCAGCCAUGUUUACGUCACUCCUAAAAGGGCG
GCUUUGCCAAGUGUUU3'
```

Plk1 Antisense siRNA: (unmodified RNA)

```
5'GCACUUGGCAAAGCCGCCCUU3'     (SEQ ID NO: 10)
```

SWAP Chimera:
SWAP RNA Sense Strand: (modified with 2' fluoro pyrimidines indicated in italics)

```
                                           (SEQ ID NO: 19)
5'GGGAGGACGAUGCGGAUCAGCCAUGUUUACGUCACUCCUAAAAG
CACUUGGCAAAGCCGCCCUU3'
```

Plk1 Sense siRNA: (unmodified RNA)

```
5'GGGCGGCUUUGCCAAGUGCUU3'     (SEQ ID NO: 7)
```

SWAP-2'F Chimera:
SWAP RNA Sense Strand: (modified with 2' fluoro pyrimidines indicated in italics)

(SEQ ID NO: 19)
5'GGGAGGACGA*U*GCGGA*U*CAGCCA*U*G*UUU*ACG*U*CA*CU*CC*U*AAAAG*CACUU*GG*C*AAAGCCGCCC*UU*3'

Plk1 Sense siRNA: (modified with 2' fluoro pyrimidines indicated in italics)

5'GGGCGGC*UUU*GCCAAG*U*GC*UU*3' (SEQ ID NO: 48)

SWAP-2'F-PEG Chimera:
SWAP RNA Sense Strand: (modified with 2' fluoro pyrimidines indicated in italics)

(SEQ ID NO: 19)
5'GGGAGGACGA*U*GCGGA*U*CAGCCA*U*G*UUU*ACG*U*CA*CU*CC*U*AAAAG*CACUU*GG*C*AAAGCCGCCC*UU*3'

Plk1 Sense siRNA: (modified with 2' fluoro pyrimidines indicated in italics)

(SEQ ID NO: 48)
PEG (20 KDa)-5'GGGCGGC*UUU*GCCAAG*U*GC*UU*3'

G-U/SWAP Chimera:
G-U/SWAP RNA Sense Strand: (modified with 2' fluoro pyrimidines indicated in italics)

(SEQ ID NO: 19)
5'GGGAGGACGA*U*GCGGA*U*CAGCCA*U*G*UUU*ACG*U*CA*CU*CC*U*AAAAG*CACUU*GG*C*AAAGCCGCCC*UU*3'

Plk1 Sense siRNA: (unmodified RNA)

5'GGGCGGCUUUGCCAAGUGUUU3' (SEQ ID NO: 20)

Stem Loop Chimera: (modified with 2' fluoro pyrimidines indicated in italics)

(SEQ ID NO: 21)
5'GGGCGGC*UUU*GCCAAG*U*GC*U*UGGGAGGACGA*U*GCGGA*U*CAGCCA*U*G*UUU*ACG*U*CA*CU*CC*U*AAGCA*CUU*GGCAAAGCCGCCC*UU*3'

A10-3.2-Con Chimera:
A10-3.2-Con RNA Sense Strand: (modified with 2' fluoro pyrimidines indicated in italics)

(SEQ ID NO: 22)
5'GGGAGGACGA*U*GCGGA*U*CAGCCA*U*G*UUU*ACG*U*CA*CU*CC*U*AA*UUC**UCC*GAACG*U*G*U*CACG*UUU*3'

Con siRNA anti-sense: (unmodified RNA)

5'ACGUGACACGUUCGGAGAAUU3' (SEQ ID NO: 23)

Generating Individual Chimeras
Double-stranded DNA templates were generated by PCR as described in McNamara et al., 2006. Briefly, templates and primers for generating the individual chimeras are listed: PSMA template (5'GGGAGGACGATGCGGATCAGCCATGTT-TACGTCACTCCTTGTCAAT CCTCATCGGCAGAC-GACTCGCCCGA3' (SEQ ID NO:24)) was used to generate A10-Plk1, BLUNT, OVH, G-U, SWAP, and G-U SWAP chimeras. The 5' primer (5'pr) was common to all above chimeras (5'pr: 5'TAATACGACTCACTATAGGGAGGACGAT-GCGG3' (SEQ ID NO:25))

The 3'primers used to generate each individual chimera are listed:

A10-Plk1
(SEQ ID NO: 26)
(3'pr:
5'GCACTTGGCAAAGCCGCCCTTTCGGGCGAGTCGTCTG3')

BLUNT
(SEQ ID NO: 27)
(3'pr:
5'GCACTTGGCAAAGCCGCCCTTTTAGGAGTGACGTAAAC3')

OVH
(SEQ ID NO: 28)
(3'pr:
5'AAGCACTTGGCAAAGCCGCCCTTTTAGGAGTGACGTAAAC3')

G-U
(SEQ ID NO: 29)
(3'pr:
5'AAACACTTGGCAAAGCCGCCCTTTTAGGAGTGACGTAAAC3')

SWAP
(SEQ ID NO: 30)
(3'pr:
5'AAGGGCGGCTTTGCCAAGTGCTTTTAGGAGTGACGTAAAC3')

G-U/SWAP
(SEQ ID NO: 31)
(3'pr:
5'AAGGGCGGCTTTGCCAAGTGCTTTTAGGAGTGACGTAAAC3')

A10-3.2-Con
(SEQ ID NO: 42)
(3'pr:
5'AAACGTGACACGTTCGGAGAATTAGGAGTGACGTAAAC3')

The Stem Loop chimera was generated with the stem loop template oligo (SL-oligo) oligo (SEQ ID NO: 32)
(5'AAGTGCTTGGGAGGACGATGCGGATCAGCCATGTTTACGTCACTCCT3')

SL 5' primer:

(SEQ ID NO: 33)
5'TAATACGACTCACTATAGGGCGGCTTTGCCAAGTGCTTGGGAGGA3'

SL 3' primer:

(SEQ ID NO: 34)
5'AAGGGCGGCTTTGCCAAGTGCTTAGGAGTGACGTAAAC3'

DNA templates were purified with Qiagen® DNA purification columns and used in in vitro transcription reactions as described in McNamara et al., 2006 to make individual RNA aptamers. All RNAs generated by in vitro transcription were produced with 2' fluoro modified pyrimidines to render the RNAs resistant to nuclease degradation. With exception of the Stem Loop chimera, the RNAs generated by transcription for all the other chimeras were annealed to the respective sense or antisense Plk1 siRNA oligos (see above). The RNAs were annealed at a ratio of 1:4 (RNAoligo:siRNA oligo) in a final concentration of 1 μM RNA in DPBS including calcium and magnesium. For the annealing step, the RNA/siRNA mixtures were incubated at 65° C. for 10 min and then allowed to cool slowly at room temperature for 30 min. Excess siRNA oligo was removed based on size exclusion with a Y-30 Amicon® column (Millipore@ cat#UFC801024).

Cell Culture

Normal human foreskin fibroblasts cells (obtained from Dr. Al Klingelhutz, U Iowa) were maintained at 37° C. and 5% $CO_2$ in DMEM supplemented with 10% FBS. Prostate carcinoma cell lines LNCaP (ATCC no. CRL-1740) were maintained in Ham's F12-K medium supplemented with 10% FBS. PC-3 and 22Rv1(1.7) luciferase expressing cells (obtained from Dr. Michael Henry, U Iowa) were grown in RPMI 1640 medium (GIBCO®) supplemented with 10% FBS (Hyclone), 1 mM non-essential amino acids (GIBCO®), and 100 μg/mL G-418.

$^{32}P$ Binding Assays

PC-3 PSMA-negative or LNCaP and 22Rv1(1.7) PSMA-positive prostate cancer cell lines were used for these experiments. For experiment in FIG. 2A; 50,000 PC-3 or LNCaP cells (500 cells/μL) in DPBS (including calcium and magnesium) were blocked with 100 μg/mL tRNA and poly (I:C) for 15 min. Blocked cells were then incubated at 37° C. for 30 min with 500,000 cpms of $\gamma$-$^{32}P$ end-labeled A10-Plk1 aptamer or truncated versions of A10-Plk1 (A10-3; A10-3.2) in block solution. Cells were then washed profusely with DPBS (including calcium and magnesium) and bound/internalized RNAs measured by scintillation counter. % Aptamer Bound was calculated based on input counts. This experiment was performed in triplicate. For determining the relative affinity of the PSMA aptamer and truncated PSMA aptamers, LNCaP cells were fixed in 1% formaldehyde in PBS for 20 min at RT. Fixed cells were washed several times after which cells were diluted and blocked as mentioned above. Cells were then incubated with serial dilutions of $\gamma$-$^{32}P$ end-labeled RNAs ranging from 2 nM to 0 nM at 37° C. for 10 min Bound RNAs were determined by filter binding assay as described in McNamara et al., 2008. For assessing binding efficacy and specificity of the individual optimized PSMA chimeras, PC-3, LNCaP, and 22Rv1(1.7) cells were prepped as for the experiment in FIG. 2A above. Cells were then incubated with 500,000 cpms of $\gamma$-$^{32}P$ end-labeled chimeras for 30 min at 37° C. Following several washes with DPBS (plus divalence) bound/internalized RNAs were determined by scintillation counter. % RNA Bound was calculated based on input counts.

Silencing Assay and Quantitative PCR

PSMA-positive 22Rv1 (1.7) cells were transfected with increasing amounts (4, 40, or 400 nM) of the individual optimized chimeras using SuperFect® (Qiagen®) for 6 h (FIG. 3A). Alternatively, cells were treated with increasing amounts (4, 40, or 400 nM) of the individual optimized chimeras in the absence of transfection reagent (FIG. 3B). 24 h following treatment, cells were processed for total RNA using RNAeasy® Kit (Qiagen®). For the in vivo experiments in FIG. 6G, tumors from mice treated with the various chimeras were excised and processed for total RNA followed by mRNA extraction as recommended by the manufacturer (RNeasy® cat#75142 and Oligotext cat#70042; Qiagen® Inc. Valencia, Calif.). Gene silencing was assessed by either quantitative RT-PCR (qRT-PCR) or immunoblotting using antibodies specific to human Plk1 (Zymed) as previously described (McNamara et al., 2006). Real-time PCR was performed on mRNA (50 ng) from 22Rv1(1.7) cells treated with the various siRNAs or chimeras using iScript™ One-Step RT-PCR Kit with SYBR Green (Biorad®) with a Biorad iCycler®. All reactions were done in a 50 μl volume in triplicate. Primers for human GAPDH and PLK1 are: GAPDH forward: 5'-TCGCTCTCTGCTCCTCCTGTTC-3' (SEQ ID NO:35); GAPDH reverse: 5'-CGCCCAATACGAC-CAAATCC-3' (SEQ ID NO:36); PLK1 forward: 5'-GA-CAAGTACGGCCTTGGGTA-3' (SEQ ID NO:37); PLK1 reverse: 5'-GTGCCGTCACGCTCTATGTA-3' (SEQ ID NO:38). PCR parameters were as follows: 50° C. for 30 min, 5 min of Taq activation at 95° C., followed by 45 cycles of PCR at 95° C. ×30 s, 57° C. ×30 s, 72° C. ×30 s. Standard curves were generated and the relative amount of target gene mRNA was normalized to GAPDH mRNA. Specificity was verified by melt curve analysis and agarose gel electrophoresis. %Plk1 mRNA expression in treated cells was determined relative to untransfected/untreated (UNT) control sample which was set to 100%.

In vitro Dicer Assay

The in vitro Dicer assays were performed as described previously (McNamara et al., *Nat. Biotechnol.* 24:1005-1015 (2006)) with minor modifications. Briefly, The Plk1 guide and passenger strands were end labeled with T4 polynucleotide kinase (PNK) and $\gamma$-$^{32}P$-CTP. The corresponding strands of the various PSMA-Plk1 RNA aptamers were then annealed, with equimolar amounts, of the labeled siRNA strands in DPBS (with calcium and magnesium) to form the chimeras. The chimeras (100 pmol) were then incubated with 1U of human recombinant Dicer enzyme at 37° C. for either 1 h or 2 h, following manufacturer's recommendations (Genlantis Cat#T520002, San Diego, Calif.). Reactions were stopped with stop buffer and electrophoresed in a non-denaturing 15% polyacrylamide gel. The gels were dried and exposed to X-ray film.

Small Fragment Northerns

Transfection: 22Rv1(1.7) PSMA positive prostate cancer cells were transfected with 200 pmols each of either siRNA duplex, A10-Plk1, BLUNT, OVH, G-U, SWAP, or Stem Loop chimeras using SuperFect® Reagent (Qiagen®). After 24 h cells were processed and RNAs extracted using Trizol extraction. Untreated (UNT) cells were used as a negative control for this assay.

Probe Synthesis: DNA templates complementary to the sense strand and anti-sense strand of the Plk1 siRNA were ordered from Integrated DNA Technologies® (IDT).

Anti-sense probe 5'GCACTTGGCAAAGCCGCCCTT3' (SEQ ID NO:39)

Sense probe 5'GGGCGGCTTTGCCAAGTGCTT3' (SEQ ID NO:40)

U6 probe (5'ATACAGAGAAGATTTAGCATGGC-CCCTGC3' (SEQ ID NO:41)) was used as an internal loading control.

Five pmols of each probe was 5' terminally modified through addition of [$\gamma$-$^{32}P$] (6000 ci/mmol; 8.3 pmols) catalyzed by T4 polynucleotide kinase (NEB). Reaction was carried out for 30 in at 37° C. Reaction was cleaned through utilization of a G25 spin column (GE®). Labeled probes were quantitated by scintillation counter and equal counts were utilized for probing the northern blot.

Small Fragment Northern Blot: 10 μg of RNA from each sample and 4 μl of Decade™ Marker System (Ambion®) were heated at 95° C. for 5 min and immediately loaded onto a 15% Polyacrylamide-8M Urea denaturing tris buffered saline (TBE) gel. Duplicate gels were loaded. The gels were run at 24 Watts for 3 h after which they were transferred onto a Hybond® Nt Nylon membrane in 1× TBE on ice for 1 h at 20V utilizing a semi-dry transfer apparatus. The nylon membranes were chemically cross-linked as previously described by (Pall et al., Nat. Protoc. 3:1077-1084 (2008)) by incubating in chemical cross-linking solution (methyl-imidazole/EDC [1-ethyl-3-(3-dimethylaminopropyl)carbamide) at 55° C. for 2 h or using a Stratalinker® UV crosslinker The membranes were pre-hybridized by incubating in Church's Buffer containing 1 mg of boiled salmon sperm at 37° C. for 2 h. Following the pre-hybridization step, the sense or anti-sense probes were added directly to the pre-hybridized blots respectively and incubated at 37° C. overnight. The next day blots were washed 1× with 1×SSC/0.1% SDS for 20 min at 37° C. followed by 3 more washes utilizing 0.5×SSC/0.1% SDS for 20 min at 37° C. Blots were exposed overnight at −80° C. Each blot was stripped utilizing boiling 0.5% SDS and re-probed for U6.

Proliferation (DNA Synthesis) Assay

PSMA-positive 22Rv1(1.7) cells were trypsinized and seeded in 12-well plates at ~20,000 cells/well. The next day cells were treated with either 400 nM or 4 nM of the various aptamer-siRNA chimeras for 24 h. Fresh media containing individual PSMA chimeras and $^3$H-thymidine (1 µCi/mL medium) was then added to cells to monitor DNA synthesis. After 24 h incubation in the presence of media containing $^3$H-thymidine, cells were washed twice with PBS, washed once with 5% w/v trichloroacetic acid (TCA) (VWR), collected in 0.5 mL of 0.5N NaOH (VWR) and placed in scintillation vials for measurement of $^3$H-thymidine incorporation.

Cell Cycle Profile (Propidium Iodide Staining)

22Rv1(1.7) cells were seeded on 60 mm plates on Day 1. On Day 2 cells were treated with 4 nM of the various PSMA chimeras. Cells were processed on Day 4 and DNA content measured by propidium iodide (PI) staining. Briefly, cells were trypsinized and washed several times with DPBS. Cells were then resuspended in NIM Buffer (0.5% BSA; 0.1% NP-40 in PBS) supplemented with 0.1 mg/ml RNAse A (DNAse free) and 5 µg/mL PI. Nocodazole (Noc) was used as a positive control to arrest cells in mitosis (G2/M phase of the cell cycle). Cells were treated with 10Ong/mL of Noc for 16 h prior to staining with PI. Stained cells were processed by flow cytometry to measure DNA content.

Cell Viability Assay (Caspase 3)

PSMA-positive 22Rv1(1.7) cells were treated with either 400 nM or 4 nM of the various optimized chimeras as described above. Cells were also treated with medium containing 2 nM cisplatin for 30 h as a positive control for apoptosis. Untreated cells were used as a negative control for the assay. Cells were then fixed and stained for active caspase 3 using a PE-conjugated antibody specific to cleaved caspase 3 as specified in manufacturer's protocol (Pharmingen). Flow cytometric analysis was used to quantify percentage PE positive cells as a measure of apoptosis.

Tumor Implantation and Monitoring Tumor Growth

Athymic nude male mice (nu/nu) 6-10 weeks old were obtained from Harlan Sprague Dawley, Inc. and maintained in a sterile environment according to guidelines established by the US Department of Agriculture and the American Association for Accreditation of Laboratory Animal Care (AAALAC). This project was approved by the Institutional Animal Care and Utilization Committee (IAUCUC) of the University of Iowa. Athymic mice were inoculated with either 1×10$^6$ (in 100 µl of 50% Matrigel™ matrix) in vitro propagated PC-3 or 22Rv1(1.7) cells subcutaneously injected into each flank. Approximately 80 non-necrotic 22Rv1(1.7) tumors and 40 non-necrotic PC-3 tumors, which exceeded 0.7 cm in diameter, were randomly divided into four groups or two groups respectively of 10 mice per treatment group as follows: group 1, no treatment (DPBS); group 2, treated with BLUNT (1 nmol/injection×10); group 3, treated with SWAP (1 nmol/injection×10); group 4, treated with A10-3.2-CON (1 nmol/injection×10). Compounds were injected intraperitoneally (i.p.) in 100 µl volumes every day for a total of 10 injections. Day 0 marks the first day of injection. Tumors were measured (in two dimensions) every other day with calipers. The following formula was used to calculate tumor volume: $V_T$=L× W$^2$/2 (W, the shortest dimension; L, the longest dimension). The growth curves are plotted as the means tumor volume±s.e.m. The animals were sacrificed three days after the last treatment and the tumors were excised and formalin fixed for immunohistochemistry. Slides of serial sections were stained with hematoxylin and eosin (H&E) and processed for TUNEL using the ApopTag® Kit (Millipore™) as a measure of apoptosis.

For the PSMA-positive tumors treated with PEGylated SWAP chimera, athymic nude male mice (nu/nu) 6-10 weeks old were injected with 22Rv1(1.7) cells as indicated above. A total of 7 mice per treatment group were injected. After approximately 3 weeks when tumors had reached 0.7 cm in diameter in the longest dimension, mice were divided into 3 groups: group 1 (DPBS), group 2 (250 pmols/injection SWAP), and group 3 (250 pmols/injection SWAP-PEG). Compounds were injected intraperitoneally (i.p.) in 100 µl volumes every other day for a total of 5 injections. Tumors were measured every other day on the day prior to the compound injection.

Bioluminescence Imaging (BLI)

To examine tumor size following treatment, we injected luciferin intraperitoneally (50 µl of 15 mg/ml luciferin/10 g mouse body weight) using a 26-gauge needle. Following a 5 min incubation, we performed bioluminescence imaging (BLI) in a Xenogen IVIS®100 imaging system (Xenogen) using a 5 s exposure. Mice were imaged in a dorsal (5 min post-luciferin injection) presentation to monitor tumor growth/status following treatment. A mouse was euthanatized when it reached clinical endpoints such as >15% body weight loss or tumors of >2 cm in the longest diameter. We measured whole body tumor growth rates as follows: We placed a circular region of interest (ROI) around the tumor sites of each mouse and quantified total flux using Living Image® Software v2.50 (Xenogen) with the units of photons/sec/cm2/sr.

Enzyme-linked Immunosorbent Assays (ELISAs)

Athymic nude male mice (nu/nu) (a total of six per treatment group) were injected with 1 nmol of either A10-3.2-Con or SWAP chimeras in 250 µL of saline (DPBS). As a positive control for immunostimulation, mice were injected with 200 ng of polyinosinic:polycytidylic acid (poly I:C) in 100 µL saline. Mice injected with saline alone (250 µL) were used as a negative control for immune stimulation. 18 h after injection ~300 µL of blood was drawn from each mouse. The blood was allowed to coagulate at room temperature before centrifuging the blood samples at 13,000 rpm for 10 min to remove erythrocytes and collect serum. Levels of the cytokines interleukin-6 (IL-6) and interferon-α (INT-α) in the serum of treated mice were determined by ELISA following manufacturer's recommendations (IL-6: R&D Systems® Inc. cat #DY406; INT-α: PBL Biomedical Laboratories cat #42100-1).

5'-Rapid amplification of cDNA ends (5'-RACE) PCR analysis mRNA (10 ng) from tumors treated with different chimeras was ligated to a GeneRacer® adaptor (cat #: L1502-01; Invitrogen®, Carlsbad, Calif.) without prior treatment. Ligated RNA was reverse transcribed using a gene-specific primer 1 (GSP1: 5'-GAATCCTACGACGTGCTGGT-3'

(SEQ ID NO:43)). In order to detect cleavage products, PCR was performed using primers complementary to the RNA adaptor (GR5'pr: 5'-CGACTGGAGCACGAGGACACTGA-3' (SEQ ID NO:44)) and gene-specific primer 2 (GSP2: 5'-GCTGCGGTGAATGGATATTT-3' (SEQ ID NO:45)) as previously described (McNamara et al., Nat. Biotechnol. 24:1005-1015 (2006)). The amplification products were resolved by agarose gel electrophoresis and visualized by ethidium bromide staining. The identity of the specific PCR products was confirmed by sequencing of the excised bands.

Pharmacokinetics (PK Measurements)

C57/BL6 mice (n=3 per treatment group) were inject intraperitoneally (i.p.) with either DPBS or 1 nmol of either SWAP chimera or SWAP chimera modified with a 20 KDa polyethylene glycol group (PEG) (SWAP-PEG). Approximately 100 µL of blood volume was retrieved from each mouse at 10 min, 1 h, 5 h, 30 h post injection with compound. The RNA chimeras in blood serum samples were extracted with phenol:chloroform and chloroform. Total RNA in samples was digested with RNAse A to remove endogenous RNA and recover nuclease resistant chimeras. Excess RNAse A was removed with a subsequent phenol:chloroform extraction and the RNA chimeras were ethanol precipitated for 2 h at $-80°$ C. by addition of 1/10 volume of sodium acetate, 5 µL of linear acrylamide and 2 volumes of 100% ethanol. RNA chimera pellets were resuspended in 50 µL of TE and 5 µL of the recovered RNA used for quantitative PCR analysis.

Pharmacodynamic (PD)

Athymic nude male mice (nu/nu) 6-10 weeks old were inoculated with $1\times10^6$ (in 100 µl of 50% Matrigel™ matrix) in vitro propagated 22Rv1(1.7) cells subcutaneously injected into each flank. Non-necrotic 22Rv1(1.7) tumors, which exceeded 0.7 cm in diameter (~0.4 cm$^3$ in volume), were randomly divided into three groups as follows: group 1, no treatment (DPBS; n=4); group 2, treated with SWAP-2'F (1 nmol/injection) (n=4); group 3, treated with SWAP2'F-PEG (1 nmol/injection) (n=4). Mice were injected on Day 1 and then again on Day 2 with either DPBS, or 1 nmol each of either the SWAP-2'F or SWAP-2'F-PEG chimeras. Tumors from these mice were excised on Day 3 (48 h) or on Day 5 (5d). The tumors were processed for total RNA followed by mRNA extraction as recommended by the manufacturer (RNeasy® cat#75142 and Oligotext® cat#70042; Qiagen® Inc. Valencia, Calif.). Silencing of Plk1 gene expression was determined by qRT-PCR as described above.

Statistical Analysis

Statistical analysis was conducted using a one-way ANOVA. A P-value of 0.05 or less was considered to indicate a significant difference. In addition to a one-way ANOVA, two-tailed unpaired t tests were conducted to compare each treatment group to every other group. For tumors expressing PSMA, Group 3 (SWAP) was significantly different from group 1 (DPBS), group 2 (BLUNT), and group 4 (A10-3.2-Con), P<0.01, on Days 8, 10, 12. Group 2 (BLUNT) was significantly different from group 1 (DPBS), P<0.05. In contrast, group 4 (A10-3.2-Con) was not significantly different from the DPBS control group, P>0.05, at any point during the treatment. For PSMA negative PC-3 tumors, there was no significant difference between the groups. For PSMA expressing tumors treated with the SWAP chimera modified with a 20 KDa polyethylene glycol group (PEG) (SWAP-PEG), group 3 (SWAP-PEG) was significantly different from group 1 (DPBS) and group 2 (SWAP), P<0.01.

PSMA Cell-Surface Expression

PSMA cell-surface expression was determined by Flow cytometry and/or immunoblotting using antibodies specific to human PSMA. Flow cytometry: HeLa, PC-3, and LNCaP cells were trypsinized, washed three times in phosphate buffered saline (PBS), and counted using a hemocytometer. 200,000 cells ($1\times10^6$ cells/mL) were resuspended in 500 µl of PBS+4% fetal bovine serum (FBS) and incubated at room temperature (RT) for 20 min. Cells were then pelleted and resuspended in 100 µL of PBS+4% FBS containing 20 µg/mL of primary antibody against PSMA (anti-PSMA 3C6: Northwest Biotherapeutics) or 20 µg/mL of isotype-specific control antibody. After a 40 min incubation at RT cells were washed three times with 500 µL of PBS+4% FBS and incubated with a 1:500 dilution of secondary antibody (anti-mouse IgG-APC) in PBS+4% FBS for 30 min at RT. Cells were washed as detailed above, fixed with 400 µL of PBS+1% formaldehyde, and analyzed by Flow cytometry. Immunoblots: HeLa, PC-3, and LNCaP cells were collected as described above. Cell pellets were resuspended in 1× RIPA buffer (150 mM NaCl, 50 mM Tris-HCl pH 8.0, 1 mM EDTA, 1% NP-40) containing lx protease and phosphatase inhibitor cocktails (Sigma) and incubated on ice for 20 min. Cells were then pelleted and 25 µg of total protein from the supernatants were resolved on a 7.5% SDS-PAGE gel. PSMA was detected using an antibody specific to human PSMA (anti-PSMA 3C6; Northwest Biotherapeutics).

Cell-Surface Binding of Aptamer-siRNA Chimeras

PC-3 or LNCaP cells were trypsinized, washed twice with 500 gL PBS, and fixed in 400 µL of FIX solution (PBS+1% formaldehyde) for 20 min at RT. After washing cells to remove any residual trace of formaldehyde, cell pellets were resuspended in 1× Binding Buffer (IXBB) (20 mM HEPES pH 7.4, 150 mM NaCl, 2 mM $CaCl_2$, 0.01% BSA) and incubated at 37° C. for 20 min. Cells were then pelleted and resuspended in 50 µL of 1× BB (pre-warmed at 37° C.) containing either 400 nM FAM-G labeled A10 aptamer or 400vnM FAM-G labeled aptamer-siRNA chimeras. Due to the low incorporation efficiency of FAM-G during the transcription reaction, for comparison of A10-Plk1 and mutA10-Plk1 cell surface binding up to 10 µM of FAM-G labeled aptamer chimeras were used. Concentrations of FAM-G labeled aptamer and aptamer-siRNA chimeras for the relative affinity measurements varied from 0 to 4 µM. Cells were incubated with the RNA for 40 min at 37° C., washed three times with 500 µL of 1× BB pre-warmed at 37° C., and finally resuspended in 400 µL of FIX solution pre-warmed at 37° C. Cells were then assayed using Flow cytometry as detailed above and the relative cell surface binding affinities of the A10 aptamer and A10 aptamer-siRNA chimera derivatives were determined.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A nucleic acid molecule consisting of the nucleic acid sequence aptamer A10-3.2 (5'-GGGAGGACGAUGCG-GAUCAGCCAUGUUUACGUCACUCCU-3' (SEQ ID NO:5)).

2. A conjugate comprising the nucleic acid molecule of claim 1 linked to a therapeutic or diagnostic molecule.

3. The conjugate of claim 2, wherein the therapeutic molecule is a siRNA molecule having a guide strand and a passenger strand that form a duplex, wherein the guide strand is linked to the nucleic acid molecule, and wherein the guide strand or passenger strand comprises the nucleic acid sequence 5'-GGGCGGCUUUGCCAAGUGUUU-3' (SEQ ID NO:6) or 5'-GGGCGGCUUUGCCAAGUGCUU-3' (Plk1, SEQ ID NO:7) or 5'-GGGCGGCUUUGC-CAAGUGU-3' (SEQ ID NO:8) or 5'-GCACUUG-GCAAAGCCGCCCUU-3' (SEQ ID NO:10).

4. A conjugate comprising the nucleic acid molecule of Stem Loop Chimera SEQ ID NO:21.

5. The conjugate of claim 2, which further comprises a PEG molecule, wherein the PEG molecule has an average molecular weight of about 10 to 100 kDa in size.

6. A method for delivering a therapeutic or diagnostic molecule to a cell having a PMSA receptor, comprising contacting the cell with the conjugate of claim 2.

7. A pharmaceutical composition comprising the conjugate of claim 2 and a pharmaceutically acceptable carrier.

8. A method for treating a patient having prostate cancer comprising administering a conjugate of claim 2 to the patient.

9. A conjugate comprising a nucleic acid molecule not more than 45 nucleotides in length comprising the nucleic acid sequence 5'-$n_1n_2n_3$CGGAUCAGC$n_4n_5n_6$GUUUA-3' (SEQ ID NO:1), wherein each $n_x$ can be present or absent, wherein when present each $n_x$ represents any nucleotide linked to a therapeutic molecule, wherein the therapeutic molecule is an siRNA.

10. The conjugate of claim 9, wherein the therapeutic molecule is a siRNA molecule having a guide strand and a passenger strand that form a duplex, wherein the guide strand is linked to the nucleic acid molecule, and wherein the guide strand or passenger strand comprises the nucleic acid sequence 5'-GGGCGGCUUUGCCAAGUGUUU-3' (SEQ ID NO:6) or 5'-GGGCGGCUUUGCCAAGUGCUU-3' (Plk1, SEQ ID NO:7) or 5'-GGGCGGCUUUGC-CAAGUGU-3' (SEQ ID NO:8) or 5'-GCACUUG-GCAAAGCCGCCCUU-3' (SEQ ID NO:10).

11. The conjugate of claim 9, which further comprises a PEG molecule covalently bound to the conjugate, wherein the PEG molecule has an average molecular weight of about 10 to 100 kDa in size.

12. A method for delivering a therapeutic or diagnostic molecule to a cell having a PMSA receptor, comprising contacting the cell with the conjugate of claim 9.

13. A pharmaceutical composition comprising the conjugate of claim 9 and a pharmaceutically acceptable carrier.

14. A method for treating a patient having prostate cancer comprising administering a conjugate of claim 9 to the patient.

15. The conjugate of claim 4, which further comprises a PEG molecule covalently bound to the conjugate, wherein the PEG molecule has an average molecular weight of about 10 to 100 kDa in size.

* * * * *

UNITED STATES PATENT AND TRADEMARK OFFICE
CERTIFICATE OF CORRECTION

PATENT NO.       : 8,685,937 B2
APPLICATION NO.  : 13/057443
DATED            : April 1, 2014
INVENTOR(S)      : Giangrande et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 344 days.

Signed and Sealed this
Twenty-ninth Day of September, 2015

Michelle K. Lee
*Director of the United States Patent and Trademark Office*

```
                              SEQUENCE LISTING

<160> NUMBER OF SEQ ID NOS: 48

<210> SEQ ID NO 1
<211> LENGTH: 20
<212> TYPE: DNA
<213> ORGANISM: Artificial sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<223> OTHER INFORMATION: see specification as filed for detailed
      description of substitutions and preferred embodiments
<220> FEATURE:
<221> NAME/KEY: modified_base
<222> LOCATION: (1)..(3)
<223> OTHER INFORMATION: a, c, g, u, t, unknown, other or absent
<220> FEATURE:
<221> NAME/KEY: modified_base
<222> LOCATION: (13)..(15)
<223> OTHER INFORMATION: a, c, g, u, t, unknown, other or absent

<400> SEQUENCE: 1
nnncggauca gcnnnguuua                                                    20

<210> SEQ ID NO 2
<211> LENGTH: 20
<212> TYPE: RNA
<213> ORGANISM: Artificial sequence
<220> FEATURE:
<223> OTHER INFORMATION: Description of Artificial Sequence: Synthetic
      oligonucleotide

<400> SEQUENCE: 2
augcggauca gccauguuua                                                    20

<210> SEQ ID NO 3
<211> LENGTH: 28
<212> TYPE: DNA
<213> ORGANISM: Artificial sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<223> OTHER INFORMATION: see specification as filed for detailed
      description of substitutions and preferred embodiments
<220> FEATURE:
<221> NAME/KEY: modified_base
<222> LOCATION: (1)..(7)
<223> OTHER INFORMATION: a, c, g, u, t, unknown, other or absent
```

```
<220> FEATURE:
<221> NAME/KEY: modified_base
<222> LOCATION: (17)..(19)
<223> OTHER INFORMATION: a, c, g, u, t, unknown, other or absent
<220> FEATURE:
<221> NAME/KEY: modified_base
<222> LOCATION: (25)..(28)
<223> OTHER INFORMATION: a, c, g, u, t, unknown, other or absent

<400> SEQUENCE: 3
nnnnnnncgg aucagcnnng uuuannnn                                      28

<210> SEQ ID NO 4
<211> LENGTH: 28
<212> TYPE: RNA
<213> ORGANISM: Artificial sequence
<220> FEATURE:
<223> OTHER INFORMATION: Description of Artificial Sequence: Synthetic
      oligonucleotide

<400> SEQUENCE: 4
gacgaugcgg aucagccaug uuuacguc                                      28

<210> SEQ ID NO 5
<211> LENGTH: 39
<212> TYPE: RNA
<213> ORGANISM: Artificial sequence
<220> FEATURE:
<223> OTHER INFORMATION: Description of Artificial Sequence: Synthetic
      oligonucleotide

<400> SEQUENCE: 5
gggaggacga ugcggaucag ccauguuuac gucacuccu                          39

<210> SEQ ID NO 6
<211> LENGTH: 21
<212> TYPE: RNA
<213> ORGANISM: Artificial sequence
<220> FEATURE:
<223> OTHER INFORMATION: Description of Artificial Sequence: Synthetic
      oligonucleotide

<400> SEQUENCE: 6
gggcggcuuu gccaaguguu u                                             21

<210> SEQ ID NO 7
<211> LENGTH: 21
<212> TYPE: RNA
<213> ORGANISM: Artificial sequence
<220> FEATURE:
<223> OTHER INFORMATION: Description of Artificial Sequence: Synthetic
      oligonucleotide

<400> SEQUENCE: 7
gggcggcuuu gccaagugcu u                                             21

<210> SEQ ID NO 8
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotide

<400> SEQUENCE: 8
gggcggcuuu gccaagugu                                                19

<210> SEQ ID NO 9
```

```
<211> LENGTH: 19
<212> TYPE: RNA
<213> ORGANISM: Artificial sequence
<220> FEATURE:
<223> OTHER INFORMATION: Description of Artificial Sequence: Synthetic
      oligonucleotide

<400> SEQUENCE: 9
gcacuuggca aagccgccc                                                      19

<210> SEQ ID NO 10
<211> LENGTH: 21
<212> TYPE: RNA
<213> ORGANISM: Artificial sequence
<220> FEATURE:
<223> OTHER INFORMATION: Description of Artificial Sequence: Synthetic
      oligonucleotide

<400> SEQUENCE: 10
gcacuuggca aagccgcccu u                                                   21

<210> SEQ ID NO 11
<211> LENGTH: 40
<212> TYPE: DNA
<213> ORGANISM: Artificial sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<223> OTHER INFORMATION: see specification as filed for detailed
      description of substitutions and preferred embodiments
<220> FEATURE:
<221> NAME/KEY: modified_base
<222> LOCATION: (1)..(12)
<223> OTHER INFORMATION: a, c, g, u, t, unknown, other or absent
<220> FEATURE:
<221> NAME/KEY: modified_base
<222> LOCATION: (22)..(24)
<223> OTHER INFORMATION: a, c, g, u, t, unknown, other or absent
<220> FEATURE:
<221> NAME/KEY: modified_base
<222> LOCATION: (30)..(39)
<223> OTHER INFORMATION: a, c, g, u, t, unknown, other or absent
<220> FEATURE:
<221> NAME/KEY: modified_base
<222> LOCATION: (40)..(40)
<223> OTHER INFORMATION: u or absent

<400> SEQUENCE: 11
nnnnnnnnnn nncggaucag cnnnguuuan nnnnnnnnnn                               40

<210> SEQ ID NO 12
<211> LENGTH: 71
<212> TYPE: RNA
<213> ORGANISM: Artificial sequence
<220> FEATURE:
<223> OTHER INFORMATION: Description of Artificial Sequence: Synthetic
      oligonucleotide

<400> SEQUENCE: 12
gggaggacga ugcggaucag ccauguuuac gucacuccuu gucaauccuc aucggcagac         60
gacucgcccg a                                                              71

<210> SEQ ID NO 13
<211> LENGTH: 21
<212> TYPE: DNA
<213> ORGANISM: Artificial sequence
<220> FEATURE:
```

<223> OTHER INFORMATION: Description of Artificial Sequence: Synthetic
      oligonucleotide

<400> SEQUENCE: 13
aattctccga acgtgtcacg t                                              21

<210> SEQ ID NO 14
<211> LENGTH: 21
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 14
aagggcggct ttgccaagtg c                                              21

<210> SEQ ID NO 15
<211> LENGTH: 92
<212> TYPE: RNA
<213> ORGANISM: Artificial sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 2'fluoro cytidine
<220> FEATURE:
<221> NAME/KEY: modified_base
<222> LOCATION: (11)..(11)
<223> OTHER INFORMATION: 2'fluoro uridine
<220> FEATURE:
<221> NAME/KEY: modified_base
<222> LOCATION: (13)..(13)
<223> OTHER INFORMATION: 2'fluoro cytidine
<220> FEATURE:
<221> NAME/KEY: modified_base
<222> LOCATION: (17)..(17)
<223> OTHER INFORMATION: 2'fluoro uridine
<220> FEATURE:
<221> NAME/KEY: modified_base
<222> LOCATION: (21)..(22)
<223> OTHER INFORMATION: 2'fluoro cytidine
<220> FEATURE:
<221> NAME/KEY: modified_base
<222> LOCATION: (24)..(24)
<223> OTHER INFORMATION: 2'fluoro uridine
<220> FEATURE:
<221> NAME/KEY: modified_base
<222> LOCATION: (26)..(28)
<223> OTHER INFORMATION: 2'fluoro uridine
<220> FEATURE:
<221> NAME/KEY: modified_base
<222> LOCATION: (30)..(30)
<223> OTHER INFORMATION: 2'fluoro cytidine
<220> FEATURE:
<221> NAME/KEY: modified_base
<222> LOCATION: (32)..(32)
<223> OTHER INFORMATION: 2'fluoro uridine
<220> FEATURE:
<221> NAME/KEY: modified_base
<222> LOCATION: (33)..(33)
<223> OTHER INFORMATION: 2'fluoro cytidine
<220> FEATURE:
<221> NAME/KEY: modified_base
<222> LOCATION: (35)..(35)
<223> OTHER INFORMATION: 2'fluoro cytidine
<220> FEATURE:
<221> NAME/KEY: modified_base
<222> LOCATION: (36)..(36)
<223> OTHER INFORMATION: 2'fluoro uridine
<220> FEATURE:
<221> NAME/KEY: modified_base
<222> LOCATION: (37)..(38)
<223> OTHER INFORMATION: 2'fluoro cytidine

```
<220> FEATURE:
<221> NAME/KEY: modified_base
<222> LOCATION: (39)..(40)
<223> OTHER INFORMATION: 2'fluoro uridine
<220> FEATURE:
<221> NAME/KEY: modified_base
<222> LOCATION: (42)..(42)
<223> OTHER INFORMATION: 2'fluoro uridine
<220> FEATURE:
<221> NAME/KEY: modified_base
<222> LOCATION: (43)..(43)
<223> OTHER INFORMATION: 2'fluoro cytidine
<220> FEATURE:
<221> NAME/KEY: modified_base
<222> LOCATION: (46)..(46)
<223> OTHER INFORMATION: 2'fluoro uridine
<220> FEATURE:
<221> NAME/KEY: modified_base
<222> LOCATION: (47)..(48)
<223> OTHER INFORMATION: 2'fluoro cytidine
<220> FEATURE:
<221> NAME/KEY: modified_base
<222> LOCATION: (49)..(49)
<223> OTHER INFORMATION: 2'fluoro uridine
<220> FEATURE:
<221> NAME/KEY: modified_base
<222> LOCATION: (50)..(50)
<223> OTHER INFORMATION: 2'fluoro cytidine
<220> FEATURE:
<221> NAME/KEY: modified_base
<222> LOCATION: (52)..(52)
<223> OTHER INFORMATION: 2'fluoro uridine
<220> FEATURE:
<221> NAME/KEY: modified_base
<222> LOCATION: (53)..(53)
<223> OTHER INFORMATION: 2'fluoro cytidine
<220> FEATURE:
<221> NAME/KEY: modified_base
<222> LOCATION: (56)..(56)
<223> OTHER INFORMATION: 2'fluoro cytidine
<220> FEATURE:
<221> NAME/KEY: modified_base
<222> LOCATION: (60)..(60)
<223> OTHER INFORMATION: 2'fluoro cytidine
<220> FEATURE:
<221> NAME/KEY: modified_base
<222> LOCATION: (63)..(63)
<223> OTHER INFORMATION: 2'fluoro cytidine
<220> FEATURE:
<221> NAME/KEY: modified_base
<222> LOCATION: (64)..(64)
<223> OTHER INFORMATION: 2'fluoro uridine
<220> FEATURE:
<221> NAME/KEY: modified_base
<222> LOCATION: (65)..(65)
<223> OTHER INFORMATION: 2'fluoro cytidine
<220> FEATURE:
<221> NAME/KEY: modified_base
<222> LOCATION: (67)..(69)
<223> OTHER INFORMATION: 2'fluoro cytidine
<220> FEATURE:
<221> NAME/KEY: modified_base
<222> LOCATION: (77)..(77)
<223> OTHER INFORMATION: 2'fluoro cytidine
<220> FEATURE:
<221> NAME/KEY: modified_base
<222> LOCATION: (80)..(80)
<223> OTHER INFORMATION: 2'fluoro cytidine
<220> FEATURE:
<221> NAME/KEY: modified_base
<222> LOCATION: (81)..(83)
<223> OTHER INFORMATION: 2'fluoro uridine
<220> FEATURE:
<221> NAME/KEY: modified_base
<222> LOCATION: (85)..(86)
<223> OTHER INFORMATION: 2'fluoro cytidine
<220> FEATURE:
<221> NAME/KEY: modified_base
<222> LOCATION: (90)..(90)
<223> OTHER INFORMATION: 2'fluoro uridine
```

```
<220> FEATURE:
<221> NAME/KEY: modified_base
<222> LOCATION: (92)..(92)
<223> OTHER INFORMATION: 2'fluoro cytidine

<400> SEQUENCE: 15
gggaggacga ugcggaucag ccauguuuac gucacuccuu gucaauccuc aucggcagac      60
gacucgcccg aaagggcggc uuugccaagu gc                                    92

<210> SEQ ID NO 16
<211> LENGTH: 62
<212> TYPE: RNA
<213> ORGANISM: Artificial sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 2'fluoro cytidine
<220> FEATURE:
<221> NAME/KEY: modified_base
<222> LOCATION: (11)..(11)
<223> OTHER INFORMATION: 2'fluoro uridine
<220> FEATURE:
<221> NAME/KEY: modified_base
<222> LOCATION: (13)..(13)
<223> OTHER INFORMATION: 2'fluoro cytidine
<220> FEATURE:
<221> NAME/KEY: modified_base
<222> LOCATION: (17)..(17)
<223> OTHER INFORMATION: 2'fluoro uridine
<220> FEATURE:
<221> NAME/KEY: modified_base
<222> LOCATION: (18)..(18)
<223> OTHER INFORMATION: 2'fluoro cytidine
<220> FEATURE:
<221> NAME/KEY: modified_base
<222> LOCATION: (21)..(22)
<223> OTHER INFORMATION: 2'fluoro cytidine
<220> FEATURE:
<221> NAME/KEY: modified_base
<222> LOCATION: (24)..(24)
<223> OTHER INFORMATION: 2'fluoro uridine
<220> FEATURE:
<221> NAME/KEY: modified_base
<222> LOCATION: (26)..(28)
<223> OTHER INFORMATION: 2'fluoro uridine
<220> FEATURE:
<221> NAME/KEY: modified_base
<222> LOCATION: (30)..(30)
<223> OTHER INFORMATION: 2'fluoro cytidine
<220> FEATURE:
<221> NAME/KEY: modified_base
<222> LOCATION: (32)..(32)
<223> OTHER INFORMATION: 2'fluoro uridine
<220> FEATURE:
<221> NAME/KEY: modified_base
<222> LOCATION: (33)..(33)
<223> OTHER INFORMATION: 2'fluoro cytidine
<220> FEATURE:
<221> NAME/KEY: modified_base
<222> LOCATION: (35)..(35)
<223> OTHER INFORMATION: 2'fluoro cytidine
<220> FEATURE:
<221> NAME/KEY: modified_base
<222> LOCATION: (36)..(36)
<223> OTHER INFORMATION: 2'fluoro uridine
<220> FEATURE:
<221> NAME/KEY: modified_base
<222> LOCATION: (37)..(38)
<223> OTHER INFORMATION: 2'fluoro cytidine
<220> FEATURE:
<221> NAME/KEY: modified_base
<222> LOCATION: (39)..(39)
<223> OTHER INFORMATION: 2'fluoro uridine
<220> FEATURE:
```

```
<221> NAME/KEY: modified_base
<222> LOCATION: (47)..(47)
<223> OTHER INFORMATION: 2'fluoro cytidine
<220> FEATURE:
<221> NAME/KEY: modified_base
<222> LOCATION: (50)..(50)
<223> OTHER INFORMATION: 2'fluoro cytidine
<220> FEATURE:
<221> NAME/KEY: modified_base
<222> LOCATION: (51)..(53)
<223> OTHER INFORMATION: 2'fluoro uridine
<220> FEATURE:
<221> NAME/KEY: modified_base
<222> LOCATION: (55)..(56)
<223> OTHER INFORMATION: 2'fluoro cytidine
<220> FEATURE:
<221> NAME/KEY: modified_base
<222> LOCATION: (60)..(60)
<223> OTHER INFORMATION: 2'fluoro uridine
<220> FEATURE:
<221> NAME/KEY: modified_base
<222> LOCATION: (62)..(62)
<223> OTHER INFORMATION: 2'fluoro cytidine

<400> SEQUENCE: 16
gggaggacga ugcggaucag ccauguuuac gucacuccua aaagggcggc uuugccaagu    60
gc                                                                  62

<210> SEQ ID NO 17
<211> LENGTH: 64
<212> TYPE: RNA
<213> ORGANISM: Artificial sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 2'fluoro cytidine
<220> FEATURE:
<221> NAME/KEY: modified_base
<222> LOCATION: (11)..(11)
<223> OTHER INFORMATION: 2'fluoro uridine
<220> FEATURE:
<221> NAME/KEY: modified_base
<222> LOCATION: (13)..(13)
<223> OTHER INFORMATION: 2'fluoro cytidine
<220> FEATURE:
<221> NAME/KEY: modified_base
<222> LOCATION: (17)..(17)
<223> OTHER INFORMATION: 2'fluoro uridine
<220> FEATURE:
<221> NAME/KEY: modified_base
<222> LOCATION: (18)..(18)
<223> OTHER INFORMATION: 2'fluoro cytidine
<220> FEATURE:
<221> NAME/KEY: modified_base
<222> LOCATION: (21)..(22)
<223> OTHER INFORMATION: 2'fluoro cytidine
<220> FEATURE:
<221> NAME/KEY: modified_base
<222> LOCATION: (24)..(24)
<223> OTHER INFORMATION: 2'fluoro uridine
<220> FEATURE:
<221> NAME/KEY: modified_base
<222> LOCATION: (26)..(28)
<223> OTHER INFORMATION: 2'fluoro uridine
<220> FEATURE:
<221> NAME/KEY: modified_base
<222> LOCATION: (30)..(30)
<223> OTHER INFORMATION: 2'fluoro cytidine
<220> FEATURE:
<221> NAME/KEY: modified_base
<222> LOCATION: (32)..(32)
<223> OTHER INFORMATION: 2'fluoro uridine
<220> FEATURE:
<221> NAME/KEY: modified_base
```

```
<222> LOCATION: (33)..(33)
<223> OTHER INFORMATION: 2'fluoro cytidine
<220> FEATURE:
<221> NAME/KEY: modified_base
<222> LOCATION: (35)..(35)
<223> OTHER INFORMATION: 2'fluoro cytidine
<220> FEATURE:
<221> NAME/KEY: modified_base
<222> LOCATION: (36)..(36)
<223> OTHER INFORMATION: 2'fluoro uridine
<220> FEATURE:
<221> NAME/KEY: modified_base
<222> LOCATION: (37)..(38)
<223> OTHER INFORMATION: 2'fluoro cytidine
<220> FEATURE:
<221> NAME/KEY: modified_base
<222> LOCATION: (39)..(39)
<223> OTHER INFORMATION: 2'fluoro uridine
<220> FEATURE:
<221> NAME/KEY: modified_base
<222> LOCATION: (47)..(47)
<223> OTHER INFORMATION: 2'fluoro cytidine
<220> FEATURE:
<221> NAME/KEY: modified_base
<222> LOCATION: (50)..(50)
<223> OTHER INFORMATION: 2'fluoro cytidine
<220> FEATURE:
<221> NAME/KEY: modified_base
<222> LOCATION: (51)..(53)
<223> OTHER INFORMATION: 2'fluoro uridine
<220> FEATURE:
<221> NAME/KEY: modified_base
<222> LOCATION: (55)..(56)
<223> OTHER INFORMATION: 2'fluoro cytidine
<220> FEATURE:
<221> NAME/KEY: modified_base
<222> LOCATION: (60)..(60)
<223> OTHER INFORMATION: 2'fluoro uridine
<220> FEATURE:
<221> NAME/KEY: modified_base
<222> LOCATION: (62)..(62)
<223> OTHER INFORMATION: 2'fluoro cytidine
<220> FEATURE:
<221> NAME/KEY: modified_base
<222> LOCATION: (63)..(64)
<223> OTHER INFORMATION: 2'fluoro uridine

<400> SEQUENCE: 17
gggaggacga ugcggaucag ccauguuuac gucacuccua aaagggcggc uuugccaagu      60
gcuu                                                                  64

<210> SEQ ID NO 18
<211> LENGTH: 64
<212> TYPE: RNA
<213> ORGANISM: Artificial sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 2'fluoro cytidine
<220> FEATURE:
<221> NAME/KEY: modified_base
<222> LOCATION: (11)..(11)
<223> OTHER INFORMATION: 2'fluoro uridine
<220> FEATURE:
<221> NAME/KEY: modified_base
<222> LOCATION: (13)..(13)
<223> OTHER INFORMATION: 2'fluoro cytidine
<220> FEATURE:
<221> NAME/KEY: modified_base
<222> LOCATION: (17)..(17)
<223> OTHER INFORMATION: 2'fluoro uridine
<220> FEATURE:
<221> NAME/KEY: modified_base
<222> LOCATION: (18)..(18)
```

```
<223> OTHER INFORMATION: 2'fluoro cytidine
<220> FEATURE:
<221> NAME/KEY: modified_base
<222> LOCATION: (21)..(22)
<223> OTHER INFORMATION: 2'fluoro cytidine
<220> FEATURE:
<221> NAME/KEY: modified_base
<222> LOCATION: (24)..(24)
<223> OTHER INFORMATION: 2'fluoro uridine
<220> FEATURE:
<221> NAME/KEY: modified_base
<222> LOCATION: (26)..(28)
<223> OTHER INFORMATION: 2'fluoro uridine
<220> FEATURE:
<221> NAME/KEY: modified_base
<222> LOCATION: (30)..(30)
<223> OTHER INFORMATION: 2'fluoro cytidine
<220> FEATURE:
<221> NAME/KEY: modified_base
<222> LOCATION: (32)..(32)
<223> OTHER INFORMATION: 2'fluoro uridine
<220> FEATURE:
<221> NAME/KEY: modified_base
<222> LOCATION: (33)..(33)
<223> OTHER INFORMATION: 2'fluoro cytidine
<220> FEATURE:
<221> NAME/KEY: modified_base
<222> LOCATION: (35)..(35)
<223> OTHER INFORMATION: 2'fluoro cytidine
<220> FEATURE:
<221> NAME/KEY: modified_base
<222> LOCATION: (36)..(36)
<223> OTHER INFORMATION: 2'fluoro uridine
<220> FEATURE:
<221> NAME/KEY: modified_base
<222> LOCATION: (37)..(38)
<223> OTHER INFORMATION: 2'fluoro cytidine
<220> FEATURE:
<221> NAME/KEY: modified_base
<222> LOCATION: (39)..(39)
<223> OTHER INFORMATION: 2'fluoro uridine
<220> FEATURE:
<221> NAME/KEY: modified_base
<222> LOCATION: (47)..(47)
<223> OTHER INFORMATION: 2'fluoro cytidine
<220> FEATURE:
<221> NAME/KEY: modified_base
<222> LOCATION: (50)..(50)
<223> OTHER INFORMATION: 2'fluoro cytidine
<220> FEATURE:
<221> NAME/KEY: modified_base
<222> LOCATION: (51)..(53)
<223> OTHER INFORMATION: 2'fluoro uridine
<220> FEATURE:
<221> NAME/KEY: modified_base
<222> LOCATION: (55)..(56)
<223> OTHER INFORMATION: 2'fluoro cytidine
<220> FEATURE:
<221> NAME/KEY: modified_base
<222> LOCATION: (60)..(60)
<223> OTHER INFORMATION: 2'fluoro uridine
<220> FEATURE:
<221> NAME/KEY: modified_base
<222> LOCATION: (62)..(64)
<223> OTHER INFORMATION: 2'fluoro uridine

<400> SEQUENCE: 18
gggaggacga ugcggaucag ccauguuuac gucacuccua aaagggcggc uuugccaagu      60
guuu                                                                  64

<210> SEQ ID NO 19
<211> LENGTH: 64
<212> TYPE: RNA
<213> ORGANISM: Artificial sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (8)..(8)
<223> OTHER INFORMATION: 2'fluoro cytidine
<220> FEATURE:
<221> NAME/KEY: modified_base
<222> LOCATION: (11)..(11)
<223> OTHER INFORMATION: 2'fluoro uridine
<220> FEATURE:
<221> NAME/KEY: modified_base
<222> LOCATION: (13)..(13)
<223> OTHER INFORMATION: 2'fluoro cytidine
<220> FEATURE:
<221> NAME/KEY: modified_base
<222> LOCATION: (17)..(17)
<223> OTHER INFORMATION: 2'fluoro uridine
<220> FEATURE:
<221> NAME/KEY: modified_base
<222> LOCATION: (18)..(18)
<223> OTHER INFORMATION: 2'fluoro cytidine
<220> FEATURE:
<221> NAME/KEY: modified_base
<222> LOCATION: (21)..(22)
<223> OTHER INFORMATION: 2'fluoro cytidine
<220> FEATURE:
<221> NAME/KEY: modified_base
<222> LOCATION: (24)..(24)
<223> OTHER INFORMATION: 2'fluoro uridine
<220> FEATURE:
<221> NAME/KEY: modified_base
<222> LOCATION: (26)..(28)
<223> OTHER INFORMATION: 2'fluoro uridine
<220> FEATURE:
<221> NAME/KEY: modified_base
<222> LOCATION: (30)..(30)
<223> OTHER INFORMATION: 2'fluoro cytidine
<220> FEATURE:
<221> NAME/KEY: modified_base
<222> LOCATION: (32)..(32)
<223> OTHER INFORMATION: 2'fluoro uridine
<220> FEATURE:
<221> NAME/KEY: modified_base
<222> LOCATION: (33)..(33)
<223> OTHER INFORMATION: 2'fluoro cytidine
<220> FEATURE:
<221> NAME/KEY: modified_base
<222> LOCATION: (35)..(35)
<223> OTHER INFORMATION: 2'fluoro cytidine
<220> FEATURE:
<221> NAME/KEY: modified_base
<222> LOCATION: (36)..(36)
<223> OTHER INFORMATION: 2'fluoro uridine
<220> FEATURE:
<221> NAME/KEY: modified_base
<222> LOCATION: (37)..(38)
<223> OTHER INFORMATION: 2'fluoro cytidine
<220> FEATURE:
<221> NAME/KEY: modified_base
<222> LOCATION: (39)..(39)
<223> OTHER INFORMATION: 2'fluoro uridine
<220> FEATURE:
<221> NAME/KEY: modified_base
<222> LOCATION: (45)..(45)
<223> OTHER INFORMATION: 2'fluoro cytidine
<220> FEATURE:
<221> NAME/KEY: modified_base
<222> LOCATION: (47)..(47)
<223> OTHER INFORMATION: 2'fluoro cytidine
<220> FEATURE:
<221> NAME/KEY: modified_base
<222> LOCATION: (48)..(49)
<223> OTHER INFORMATION: 2'fluoro uridine
<220> FEATURE:
<221> NAME/KEY: modified_base
<222> LOCATION: (52)..(52)
<223> OTHER INFORMATION: 2'fluoro cytidine
<220> FEATURE:
<221> NAME/KEY: modified_base
<222> LOCATION: (57)..(58)
<223> OTHER INFORMATION: 2'fluoro cytidine
```

-continued

```
<220> FEATURE:
<221> NAME/KEY: modified_base
<222> LOCATION: (60)..(62)
<223> OTHER INFORMATION: 2'fluoro cytidine
<220> FEATURE:
<221> NAME/KEY: modified_base
<222> LOCATION: (63)..(64)
<223> OTHER INFORMATION: 2'fluoro uridine

<400> SEQUENCE: 19
gggaggacga ugcggaucag ccauguuuac gucacuccua aaagcacuug gcaaagccgc      60
ccuu                                                                  64

<210> SEQ ID NO 20
<211> LENGTH: 21
<212> TYPE: RNA
<213> ORGANISM: Artificial sequence
<220> FEATURE:
<223> OTHER INFORMATION: Description of Artificial Sequence: Synthetic
      oligonucleotide

<400> SEQUENCE: 20
gggcggcuuu gccaaguguu u                                               21

<210> SEQ ID NO 21
<211> LENGTH: 83
<212> TYPE: RNA
<213> ORGANISM: Artificial sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: 2'fluoro cytidine
<220> FEATURE:
<221> NAME/KEY: modified_base
<222> LOCATION: (7)..(7)
<223> OTHER INFORMATION: 2'fluoro cytidine
<220> FEATURE:
<221> NAME/KEY: modified_base
<222> LOCATION: (8)..(10)
<223> OTHER INFORMATION: 2'fluoro uridine
<220> FEATURE:
<221> NAME/KEY: modified_base
<222> LOCATION: (12)..(13)
<223> OTHER INFORMATION: 2'fluoro cytidine
<220> FEATURE:
<221> NAME/KEY: modified_base
<222> LOCATION: (17)..(17)
<223> OTHER INFORMATION: 2'fluoro uridine
<220> FEATURE:
<221> NAME/KEY: modified_base
<222> LOCATION: (19)..(19)
<223> OTHER INFORMATION: 2'fluoro cytidine
<220> FEATURE:
<221> NAME/KEY: modified_base
<222> LOCATION: (20)..(21)
<223> OTHER INFORMATION: 2'fluoro uridine
<220> FEATURE:
<221> NAME/KEY: modified_base
<222> LOCATION: (29)..(29)
<223> OTHER INFORMATION: 2'fluoro cytidine
<220> FEATURE:
<221> NAME/KEY: modified_base
<222> LOCATION: (32)..(32)
<223> OTHER INFORMATION: 2'fluoro uridine
<220> FEATURE:
<221> NAME/KEY: modified_base
<222> LOCATION: (34)..(34)
<223> OTHER INFORMATION: 2'fluoro cytidine
<220> FEATURE:
<221> NAME/KEY: modified_base
<222> LOCATION: (38)..(38)
<223> OTHER INFORMATION: 2'fluoro uridine
```

```
<220> FEATURE:
<221> NAME/KEY: modified_base
<222> LOCATION: (39)..(39)
<223> OTHER INFORMATION: 2'fluoro cytidine
<220> FEATURE:
<221> NAME/KEY: modified_base
<222> LOCATION: (42)..(43)
<223> OTHER INFORMATION: 2'fluoro cytidine
<220> FEATURE:
<221> NAME/KEY: modified_base
<222> LOCATION: (45)..(45)
<223> OTHER INFORMATION: 2'fluoro uridine
<220> FEATURE:
<221> NAME/KEY: modified_base
<222> LOCATION: (47)..(49)
<223> OTHER INFORMATION: 2'fluoro uridine
<220> FEATURE:
<221> NAME/KEY: modified_base
<222> LOCATION: (51)..(51)
<223> OTHER INFORMATION: 2'fluoro cytidine
<220> FEATURE:
<221> NAME/KEY: modified_base
<222> LOCATION: (53)..(53)
<223> OTHER INFORMATION: 2'fluoro uridine
<220> FEATURE:
<221> NAME/KEY: modified_base
<222> LOCATION: (54)..(54)
<223> OTHER INFORMATION: 2'fluoro cytidine
<220> FEATURE:
<221> NAME/KEY: modified_base
<222> LOCATION: (56)..(56)
<223> OTHER INFORMATION: 2'fluoro cytidine
<220> FEATURE:
<221> NAME/KEY: modified_base
<222> LOCATION: (57)..(57)
<223> OTHER INFORMATION: 2'fluoro uridine
<220> FEATURE:
<221> NAME/KEY: modified_base
<222> LOCATION: (58)..(59)
<223> OTHER INFORMATION: 2'fluoro cytidine
<220> FEATURE:
<221> NAME/KEY: modified_base
<222> LOCATION: (60)..(60)
<223> OTHER INFORMATION: 2'fluoro uridine
<220> FEATURE:
<221> NAME/KEY: modified_base
<222> LOCATION: (64)..(64)
<223> OTHER INFORMATION: 2'fluoro cytidine
<220> FEATURE:
<221> NAME/KEY: modified_base
<222> LOCATION: (66)..(66)
<223> OTHER INFORMATION: 2'fluoro cytidine
<220> FEATURE:
<221> NAME/KEY: modified_base
<222> LOCATION: (67)..(68)
<223> OTHER INFORMATION: 2'fluoro uridine
<220> FEATURE:
<221> NAME/KEY: modified_base
<222> LOCATION: (71)..(71)
<223> OTHER INFORMATION: 2'fluoro cytidine
<220> FEATURE:
<221> NAME/KEY: modified_base
<222> LOCATION: (76)..(77)
<223> OTHER INFORMATION: 2'fluoro cytidine
<220> FEATURE:
<221> NAME/KEY: modified_base
<222> LOCATION: (79)..(81)
<223> OTHER INFORMATION: 2'fluoro cytidine
<220> FEATURE:
<221> NAME/KEY: modified_base
<222> LOCATION: (82)..(83)
<223> OTHER INFORMATION: 2'fluoro uridine

<400> SEQUENCE: 21
gggcggcuuu gccaagugcu ugggaggacg augcggauca gccauguuua cgucacuccu    60
aagcacuugg caaagccgcc cuu                                            83
```

```
<210> SEQ ID NO 22
<211> LENGTH: 62
<212> TYPE: RNA
<213> ORGANISM: Artificial sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 2'fluoro cytidine
<220> FEATURE:
<221> NAME/KEY: modified_base
<222> LOCATION: (11)..(11)
<223> OTHER INFORMATION: 2'fluoro uridine
<220> FEATURE:
<221> NAME/KEY: modified_base
<222> LOCATION: (17)..(17)
<223> OTHER INFORMATION: 2'fluoro uridine
<220> FEATURE:
<221> NAME/KEY: modified_base
<222> LOCATION: (18)..(18)
<223> OTHER INFORMATION: 2'fluoro cytidine
<220> FEATURE:
<221> NAME/KEY: modified_base
<222> LOCATION: (21)..(22)
<223> OTHER INFORMATION: 2'fluoro cytidine
<220> FEATURE:
<221> NAME/KEY: modified_base
<222> LOCATION: (24)..(24)
<223> OTHER INFORMATION: 2'fluoro uridine
<220> FEATURE:
<221> NAME/KEY: modified_base
<222> LOCATION: (26)..(28)
<223> OTHER INFORMATION: 2'fluoro uridine
<220> FEATURE:
<221> NAME/KEY: modified_base
<222> LOCATION: (30)..(30)
<223> OTHER INFORMATION: 2'fluoro cytidine
<220> FEATURE:
<221> NAME/KEY: modified_base
<222> LOCATION: (32)..(32)
<223> OTHER INFORMATION: 2'fluoro uridine
<220> FEATURE:
<221> NAME/KEY: modified_base
<222> LOCATION: (33)..(33)
<223> OTHER INFORMATION: 2'fluoro cytidine
<220> FEATURE:
<221> NAME/KEY: modified_base
<222> LOCATION: (35)..(35)
<223> OTHER INFORMATION: 2'fluoro cytidine
<220> FEATURE:
<221> NAME/KEY: modified_base
<222> LOCATION: (36)..(36)
<223> OTHER INFORMATION: 2'fluoro uridine
<220> FEATURE:
<221> NAME/KEY: modified_base
<222> LOCATION: (37)..(38)
<223> OTHER INFORMATION: 2'fluoro cytidine
<220> FEATURE:
<221> NAME/KEY: modified_base
<222> LOCATION: (39)..(39)
<223> OTHER INFORMATION: 2'fluoro uridine
<220> FEATURE:
<221> NAME/KEY: modified_base
<222> LOCATION: (42)..(43)
<223> OTHER INFORMATION: 2'fluoro uridine
<220> FEATURE:
<221> NAME/KEY: modified_base
<222> LOCATION: (44)..(44)
<223> OTHER INFORMATION: 2'fluoro cytidine
<220> FEATURE:
<221> NAME/KEY: modified_base
<222> LOCATION: (45)..(45)
<223> OTHER INFORMATION: 2'fluoro uridine
<220> FEATURE:
<221> NAME/KEY: modified_base
<222> LOCATION: (46)..(47)
<223> OTHER INFORMATION: 2'fluoro cytidine
<220> FEATURE:
```

```
<221> NAME/KEY: modified_base
<222> LOCATION: (51)..(51)
<223> OTHER INFORMATION: 2'fluoro cytidine
<220> FEATURE:
<221> NAME/KEY: modified_base
<222> LOCATION: (53)..(53)
<223> OTHER INFORMATION: 2'fluoro uridine
<220> FEATURE:
<221> NAME/KEY: modified_base
<222> LOCATION: (55)..(55)
<223> OTHER INFORMATION: 2'fluoro uridine
<220> FEATURE:
<221> NAME/KEY: modified_base
<222> LOCATION: (56)..(56)
<223> OTHER INFORMATION: 2'fluoro cytidine
<220> FEATURE:
<221> NAME/KEY: modified_base
<222> LOCATION: (58)..(58)
<223> OTHER INFORMATION: 2'fluoro cytidine
<220> FEATURE:
<221> NAME/KEY: modified_base
<222> LOCATION: (60)..(62)
<223> OTHER INFORMATION: 2'fluoro uridine

<400> SEQUENCE: 22
gggaggacga ugcggaucag ccauguuuac gucacuccua auucuccgaa cgugucacgu      60
uu                                                                    62

<210> SEQ ID NO 23
<211> LENGTH: 21
<212> TYPE: RNA
<213> ORGANISM: Artificial sequence
<220> FEATURE:
<223> OTHER INFORMATION: Description of Artificial Sequence: Synthetic
      oligonucleotide

<400> SEQUENCE: 23
acgugacacg uucggagaau u                                               21

<210> SEQ ID NO 24
<211> LENGTH: 71
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 24
gggaggacga tgcggatcag ccatgtttac gtcactcctt gtcaatcctc atcggcagac      60
gactcgcccg a                                                          71

<210> SEQ ID NO 25
<211> LENGTH: 32
<212> TYPE: DNA
<213> ORGANISM: Artificial sequence
<220> FEATURE:
<223> OTHER INFORMATION: Description of Artificial Sequence: Synthetic
      primer

<400> SEQUENCE: 25
taatacgact cactataggg aggacgatgc gg                                   32

<210> SEQ ID NO 26
<211> LENGTH: 37
<212> TYPE: DNA
<213> ORGANISM: Artificial sequence
```

```
<220> FEATURE:
<223> OTHER INFORMATION: Description of Artificial Sequence: Synthetic
      primer

<400> SEQUENCE: 26
gcacttggca aagccgccct ttcgggcgag tcgtctg                             37

<210> SEQ ID NO 27
<211> LENGTH: 38
<212> TYPE: DNA
<213> ORGANISM: Artificial sequence
<220> FEATURE:
<223> OTHER INFORMATION: Description of Artificial Sequence: Synthetic
      primer

<400> SEQUENCE: 27
gcacttggca aagccgccct tttaggagtg acgtaaac                            38

<210> SEQ ID NO 28
<211> LENGTH: 40
<212> TYPE: DNA
<213> ORGANISM: Artificial sequence
<220> FEATURE:
<223> OTHER INFORMATION: Description of Artificial Sequence: Synthetic
      primer

<400> SEQUENCE: 28
aagcacttgg caaagccgcc cttttaggag tgacgtaaac                          40

<210> SEQ ID NO 29
<211> LENGTH: 40
<212> TYPE: DNA
<213> ORGANISM: Artificial sequence
<220> FEATURE:
<223> OTHER INFORMATION: Description of Artificial Sequence: Synthetic
      primer

<400> SEQUENCE: 29
aaacacttgg caaagccgcc cttttaggag tgacgtaaac                          40

<210> SEQ ID NO 30
<211> LENGTH: 40
<212> TYPE: DNA
<213> ORGANISM: Artificial sequence
<220> FEATURE:
<223> OTHER INFORMATION: Description of Artificial Sequence: Synthetic
      primer

<400> SEQUENCE: 30
aagggcggct tgccaagtg cttttaggag tgacgtaaac                           40

<210> SEQ ID NO 31
<211> LENGTH: 40
<212> TYPE: DNA
<213> ORGANISM: Artificial sequence
<220> FEATURE:
<223> OTHER INFORMATION: Description of Artificial Sequence: Synthetic
      primer

<400> SEQUENCE: 31
aagggcggct tgccaagtg cttttaggag tgacgtaaac                           40

<210> SEQ ID NO 32
<211> LENGTH: 47
<212> TYPE: DNA
<213> ORGANISM: Artificial sequence
<220> FEATURE:
<223> OTHER INFORMATION: Description of Artificial Sequence: Synthetic
``` oligonucleotide

<400> SEQUENCE: 32
aagtgcttgg gaggacgatg cggatcagcc atgtttacgt cactcct      47

<210> SEQ ID NO 33
<211> LENGTH: 45
<212> TYPE: DNA
<213> ORGANISM: Artificial sequence
<220> FEATURE:
<223> OTHER INFORMATION: Description of Artificial Sequence: Synthetic
      primer

<400> SEQUENCE: 33
taatacgact cactataggg cggctttgcc aagtgcttgg gagga      45

<210> SEQ ID NO 34
<211> LENGTH: 38
<212> TYPE: DNA
<213> ORGANISM: Artificial sequence
<220> FEATURE:
<223> OTHER INFORMATION: Description of Artificial Sequence: Synthetic
      primer

<400> SEQUENCE: 34
aagggcggct tgccaagtg cttaggagtg acgtaaac      38

<210> SEQ ID NO 35
<211> LENGTH: 22
<212> TYPE: DNA
<213> ORGANISM: Artificial sequence
<220> FEATURE:
<223> OTHER INFORMATION: Description of Artificial Sequence: Synthetic
      primer

<400> SEQUENCE: 35
tcgctctctg ctcctcctgt tc      22

<210> SEQ ID NO 36
<211> LENGTH: 20
<212> TYPE: DNA
<213> ORGANISM: Artificial sequence
<220> FEATURE:
<223> OTHER INFORMATION: Description of Artificial Sequence: Synthetic
      primer

<400> SEQUENCE: 36
cgcccaatac gaccaaatcc      20

<210> SEQ ID NO 37
<211> LENGTH: 20
<212> TYPE: DNA
<213> ORGANISM: Artificial sequence
<220> FEATURE:
<223> OTHER INFORMATION: Description of Artificial Sequence: Synthetic
      primer

<400> SEQUENCE: 37
gacaagtacg gccttgggta      20

<210> SEQ ID NO 38
<211> LENGTH: 20
<212> TYPE: DNA
<213> ORGANISM: Artificial sequence

```
<220> FEATURE:
<223> OTHER INFORMATION: Description of Artificial Sequence: Synthetic
      primer

<400> SEQUENCE: 38
gtgccgtcac gctctatgta                                                  20

<210> SEQ ID NO 39
<211> LENGTH: 21
<212> TYPE: DNA
<213> ORGANISM: Artificial sequence
<220> FEATURE:
<223> OTHER INFORMATION: Description of Artificial Sequence: Synthetic
      probe

<400> SEQUENCE: 39
gcacttggca aagccgccct t                                                21

<210> SEQ ID NO 40
<211> LENGTH: 21
<212> TYPE: DNA
<213> ORGANISM: Artificial sequence
<220> FEATURE:
<223> OTHER INFORMATION: Description of Artificial Sequence: Synthetic
      probe

<400> SEQUENCE: 40
gggcggcttt gccaagtgct t                                                21

<210> SEQ ID NO 41
<211> LENGTH: 29
<212> TYPE: DNA
<213> ORGANISM: Artificial sequence
<220> FEATURE:
<223> OTHER INFORMATION: Description of Artificial Sequence: Synthetic
      probe

<400> SEQUENCE: 41
atacagagaa gatttagcat ggcccctgc                                        29

<210> SEQ ID NO 42
<211> LENGTH: 38
<212> TYPE: DNA
<213> ORGANISM: Artificial sequence
<220> FEATURE:
<223> OTHER INFORMATION: Description of Artificial Sequence: Synthetic
      primer

<400> SEQUENCE: 42
aaacgtgaca cgttcggaga attaggagtg acgtaaac                              38

<210> SEQ ID NO 43
<211> LENGTH: 20
<212> TYPE: DNA
<213> ORGANISM: Artificial sequence
<220> FEATURE:
<223> OTHER INFORMATION: Description of Artificial Sequence: Synthetic
      primer

<400> SEQUENCE: 43
gaatcctacg acgtgctggt                                                  20

<210> SEQ ID NO 44
<211> LENGTH: 23
<212> TYPE: DNA
<213> ORGANISM: Artificial sequence
<220> FEATURE:
<223> OTHER INFORMATION: Description of Artificial Sequence: Synthetic
```

-continued primer

<400> SEQUENCE: 44
cgactggagc acgaggacac tga                                              23

<210> SEQ ID NO 45
<211> LENGTH: 20
<212> TYPE: DNA
<213> ORGANISM: Artificial sequence
<220> FEATURE:
<223> OTHER INFORMATION: Description of Artificial Sequence: Synthetic
      primer

<400> SEQUENCE: 45
gctgcggtga atggatattt                                                  20

<210> SEQ ID NO 46
<211> LENGTH: 23
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 46
ggagtagaaa tgccaagtgc ttc                                              23

<210> SEQ ID NO 47
<211> LENGTH: 22
<212> TYPE: RNA
<213> ORGANISM: Artificial sequence
<220> FEATURE:
<223> OTHER INFORMATION: Description of Artificial Sequence: Synthetic
      oligonucleotide

<400> SEQUENCE: 47
gggcggcuuu gccaagugcu uc                                               22

<210> SEQ ID NO 48
<211> LENGTH: 21
<212> TYPE: RNA
<213> ORGANISM: Artificial sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: 2'fluoro cytidine
<220> FEATURE:
<221> NAME/KEY: modified_base
<222> LOCATION: (7)..(7)
<223> OTHER INFORMATION: 2'fluoro cytidine
<220> FEATURE:
<221> NAME/KEY: modified_base
<222> LOCATION: (8)..(10)
<223> OTHER INFORMATION: 2'fluoro uridine
<220> FEATURE:
<221> NAME/KEY: modified_base
<222> LOCATION: (12)..(13)
<223> OTHER INFORMATION: 2'fluoro cytidine
<220> FEATURE:
<221> NAME/KEY: modified_base
<222> LOCATION: (17)..(17)
<223> OTHER INFORMATION: 2'fluoro uridine
<220> FEATURE:
<221> NAME/KEY: modified_base
<222> LOCATION: (19)..(19)
<223> OTHER INFORMATION: 2'fluoro cytidine
<220> FEATURE:
<221> NAME/KEY: modified_base
<222> LOCATION: (20)..(21)

-continued

```
<223> OTHER INFORMATION: 2'fluoro uridine

<400> SEQUENCE: 48
gggcggcuuu gccaagugcu u                                          21
```